United States Patent [19]
Clark et al.

[11] Patent Number: 5,358,691
[45] Date of Patent: Oct. 25, 1994

[54] AUTOMATED CONTINUOUS AND RANDOM ACCESS ANALYTICAL SYSTEM

[75] Inventors: Frederic L. Clark, Plano; Gilbert Clift, Mesquite; Kendall B. Hendrick, Southlake; William J. Kanewske, III, Dallas, all of Tex.; Peter A. Lagocki, Park Ridge, Ill.; Richard R. Martin, Irving, Tex.; James E. Mitchell, Lake Barrington, Ill.; Larry W. Moore, Plano, Tex.; Charles D. Pennington, Lake Zurich; Edna S. Walker, Chicago; B. Jane Smith, Vernon Hills; Apparao Tayi, Grayslake, Ill.; James A. Vaught, Euless, Tex.; David A. Yost, Poolesville, Md.

[73] Assignee: Abbott Laboratories, Abbott Park, Ill.

[21] Appl. No.: 126,447

[22] Filed: Sep. 24, 1993

Related U.S. Application Data

[63] Continuation of Ser. No. 859,218, Mar. 27, 1992, abandoned.

[51] Int. Cl.⁵ ............................................. G01N 35/06
[52] U.S. Cl. .......................................... 422/64; 422/63; 422/67; 422/52.05; 422/52.08; 436/43; 436/47; 436/48; 436/49; 436/54; 436/165; 436/172; 436/180; 435/509
[58] Field of Search .............. 422/63, 64, 65, 66, 422/67, 82.05, 82.08100; 435/809; 436/43, 47, 48, 49, 50, 54, 164, 165, 180, 172, 805

[56] References Cited

U.S. PATENT DOCUMENTS

| | | | |
|---|---|---|---|
| 2,958,439 | 11/1960 | Yochem | 220/38.5 |
| 3,814,582 | 6/1974 | Rohrbaugh et al. | 23/230 R |
| 3,915,651 | 10/1975 | Nishi | 23/259 |
| 3,917,455 | 11/1975 | Bak et al. | 23/253 R |
| 3,951,608 | 4/1976 | Trod | 23/259 |
| 4,000,974 | 1/1977 | Acord | 23/230 R |
| 4,038,555 | 7/1977 | Freeman | 250/573 |
| 4,070,156 | 1/1978 | Moran et al. | 23/253 R |
| 4,082,121 | 4/1978 | Sturm et al. | 141/27 |
| 4,111,754 | 9/1978 | Park | 195/127 |
| 4,113,436 | 9/1978 | Werder et al. | 422/65 |
| 4,130,796 | 12/1978 | Shum | 324/61 R |
| 4,141,687 | 2/1979 | Forrest et al. | 23/230 R |
| 4,148,607 | 4/1979 | Bernoco et al. | 23/230 B |
| 4,169,543 | 10/1979 | Hall | 22/56 |

(List continued on next page.)

FOREIGN PATENT DOCUMENTS 02468909 10/1979 European Pat. Off. .
02473723 1/1980 European Pat. Off. .

(List continued on next page.)

Primary Examiner—James C. Housel
Assistant Examiner—Long V. Le
Attorney, Agent, or Firm—Daniel W. Collins; James L. Wilcox

[57] ABSTRACT

An automated, continuous and random access analytical system, having apparatus and methodology capable of simultaneously performing multiple assays of liquid samples using different assay methodologies, and providing continuous and random access while performing a plurality of different assays on the same or different samples during the same time period, is disclosed. A method is also disclosed of operating an automated continuous and random access analytical system capable of simultaneously effecting multiple assays of a plurality of liquid samples wherein scheduling of various assays of the plurality of liquid samples is followed by creating a unit dose disposable and separately transferring a first liquid sample and reagents to a reaction vessel without initiation of an assay reaction sequence, followed by physical transfer of the unit dose disposable to a processing workstation, whereby a mixture of the unit dose disposable reagents and sample are achieved during incubation. The system is capable of performing more than one scheduled assay in any order, and assays where more than such scheduled assays are presented. The automated, continuous and random access analytical system is also capable of analyzing the incubated reaction mixtures independently and individually by at least two assay procedures.

17 Claims, 28 Drawing Sheets

U.S. PATENT DOCUMENTS

| | | | |
|---|---|---|---|
| 4,234,538 | 11/1980 | Ginsberg et al. | 422/64 |
| 4,234,539 | 11/1980 | Ginsberg et al. | 422/64 |
| 4,234,540 | 11/1980 | Ginsberg et al. | 422/64 |
| 4,256,725 | 3/1981 | Rutner et al. | 424/1 |
| 4,268,477 | 5/1981 | Herzstark | 422/64 |
| 4,276,051 | 6/1981 | Ginsberg et al. | 23/230 R |
| 4,276,260 | 6/1981 | Drbal et al. | 422/100 |
| 4,278,437 | 7/1981 | Haggar | 23/230 B |
| 4,298,571 | 11/1981 | Difulvio et al. | 422/65 |
| 4,302,421 | 11/1981 | Baker | 422/64 |
| 4,311,394 | 1/1982 | Manabe | 356/440 |
| 4,311,959 | 1/1982 | Riessland et al. | 324/61 P |
| 4,313,735 | 2/1982 | Yamashita et al. | 23/230 R |
| 4,314,968 | 2/1982 | Guigan | 422/64 |
| 4,315,891 | 2/1982 | Sakurada | 422/64 |
| 4,325,910 | 4/1982 | Jordan | 422/64 |
| 4,326,851 | 4/1982 | Bello et al. | 23/230 R |
| 4,336,000 | 6/1982 | Jorgensen et al. | 417/53 |
| 4,338,279 | 7/1982 | Orimo et al. | 422/64 |
| 4,346,056 | 8/1982 | Sakurada | 422/64 |
| 4,346,742 | 8/1982 | Chase et al. | 141/1 |
| 4,406,547 | 9/1983 | Aihara | 356/414 |
| 4,412,973 | 11/1983 | Guigan | 422/72 |
| 4,429,583 | 2/1984 | Watanabe et al. | 73/864 |
| 4,430,299 | 2/1984 | Horne | 422/64 |
| 4,448,752 | 5/1984 | Banno et al. | 422/81 |
| 4,449,405 | 5/1984 | Franz et al. | 73/304 C |
| 4,451,433 | 5/1984 | Yamashita et al. | 422/63 |
| 4,456,037 | 6/1984 | Gocho | 141/1 |
| 4,457,893 | 7/1984 | Takekawa | 422/64 |
| 4,459,265 | 7/1984 | Berglund | 422/64 |
| 4,470,008 | 9/1984 | Kato | 324/61 R |
| 4,471,295 | 9/1984 | Vermeiren | 324/61 R |
| 4,472,505 | 9/1984 | Manabe et al. | 436/47 |
| 4,483,927 | 11/1984 | Takekawa | 436/43 |
| 4,495,149 | 1/1985 | Iwata et al. | 422/65 |
| 4,499,766 | 2/1985 | Fathauer et al. | 73/304 C |
| 4,502,126 | 2/1985 | Mizoguchi | 364/509 |
| 4,515,889 | 5/1985 | Klose et al. | 435/4 |
| 4,517,160 | 5/1985 | Galle et al. | 422/65 |
| 4,526,046 | 7/1985 | Oberli | 73/864.16 |
| 4,536,369 | 8/1985 | Sakurada et al. | 422/65 |
| 4,540,549 | 9/1985 | Manabe | 422/64 |
| 4,554,134 | 11/1985 | Tervamaki et al. | 422/100 |
| 4,555,941 | 12/1985 | Fathauer et al. | 73/304 |
| 4,558,946 | 12/1985 | Galle et al. | 356/73 |
| 4,568,873 | 2/1986 | Oyanagi et al. | 324/61 P |
| 4,575,492 | 3/1986 | David et al. | 436/164 |
| 4,584,885 | 4/1986 | Cadwell | 73/862.61 |
| 4,586,546 | 5/1986 | Mezei et al. | 141/2 |
| 4,595,562 | 6/1986 | Liston et al. | 422/65 |
| 4,612,289 | 9/1986 | Furuta et al. | 436/34 |
| 4,629,703 | 12/1986 | Uffenheimer | 436/45 |
| 4,634,576 | 1/1987 | Galle et al. | 422/102 |
| 4,644,807 | 2/1987 | Mar | 73/864.62 |
| 4,647,432 | 3/1987 | Wakatake | 422/64 |
| 4,676,100 | 6/1987 | Eichberger | 73/304 |
| 4,678,752 | 7/1987 | Thorne et al. | 435/291 |
| 4,679,446 | 7/1987 | Sheehan et al. | 73/864.13 |
| 4,687,638 | 8/1987 | Benajam | 422/73 |
| 4,695,430 | 9/1987 | Coville et al. | 422/65 |
| 4,699,766 | 10/1987 | Yamashita | 422/64 |
| 4,699,767 | 10/1987 | Aihara | 422/65 |
| 4,731,225 | 3/1988 | Wakatake | 422/65 |
| 4,736,638 | 4/1988 | Okawa et al. | 73/864.24 |
| 4,737,342 | 4/1988 | Herrmann et al. | 422/64 |
| 4,738,825 | 4/1988 | Kelln et al. | 422/72 |
| 4,764,342 | 8/1988 | Kelln et al. | 422/72 |
| 4,766,078 | 8/1988 | Gang | 435/291 |
| 4,774,055 | 9/1988 | Wakatake et al. | 422/64 |
| 4,781,891 | 11/1988 | Galle et al. | 422/64 |
| 4,788,150 | 11/1988 | Nelson et al. | 436/45 |
| 4,794,085 | 12/1988 | Jessop et al. | 436/54 |
| 4,805,469 | 2/1989 | Commarmot | 73/864.81 |
| 4,808,380 | 2/1989 | Minekane | 422/64 |
| 4,815,632 | 3/1989 | Ball et al. | 222/23 |
| 4,818,492 | 4/1989 | Shimizo | 422/100 |
| 4,821,080 | 4/1989 | Hayashi | 356/318 |
| 4,826,319 | 5/1989 | Namba et al. | 356/339 |
| 4,826,660 | 5/1989 | Smith et al. | 422/68 |
| 4,834,944 | 5/1989 | Wakatake | 422/64 |
| 4,836,037 | 6/1989 | Nohl et al. | 73/864.16 |
| 4,836,038 | 6/1989 | Baldwyn | 73/864.21 |
| 4,837,159 | 6/1989 | Yamada | 436/45 |
| 4,844,887 | 7/1989 | Galle et al. | 422/65 |
| 4,863,695 | 9/1989 | Fullemann | 422/100 |
| 4,864,169 | 9/1989 | Rioux et al. | 310/12 |
| 4,876,204 | 10/1989 | Inoue et al. | 436/46 |
| 4,900,513 | 2/1990 | Barker et al. | 422/64 |
| 4,906,433 | 3/1990 | Minekane | 422/64 |
| 4,908,186 | 3/1990 | Sakamaki | 422/64 |
| 4,908,320 | 3/1990 | Zakowski et al. | 436/45 |
| 4,914,377 | 4/1990 | Russell | 324/690 |
| 4,919,887 | 4/1990 | Wakatake | 422/67 |
| 4,924,702 | 5/1990 | Park | 73/304 C |
| 4,926,150 | 5/1990 | Buchschmid et al. | 335/196 |
| 4,926,701 | 5/1990 | Tompkins | 73/864.15 |
| 4,927,765 | 5/1990 | Saxon et al. | 436/43 |
| 4,961,906 | 10/1990 | Anderson et al. | 422/102 |
| 4,965,049 | 10/1990 | Lillig et al. | 422/68 |
| 4,970,053 | 11/1990 | Fechtner | 422/102 |
| 4,970,468 | 11/1990 | Ishizawa et al. | 324/662 |

(List continued on next page.)

U.S. PATENT DOCUMENTS

| Patent # | Date | Inventor | Class |
|---|---|---|---|
| 4,971,913 | 11/1990 | Manabe et al. | 436/55 |
| 4,977,786 | 12/1990 | Davis | 73/864.24 |
| 4,984,475 | 1/1991 | Uffenheimer | 73/864.22 |
| 5,005,409 | 4/1991 | Hochstein | 73/304 |
| 5,012,683 | 5/1991 | Davis | 73/864.24 |
| 5,027,075 | 6/1991 | Harding, Jr. | 324/662 |
| 5,035,150 | 7/1991 | Tompkins | 73/864.15 |
| 5,043,143 | 8/1991 | Shaw et al. | 422/65 |
| 5,045,286 | 9/1991 | Kitajima et al. | 422/100 |
| 5,049,359 | 9/1991 | Azuma et al. | 422/67 |
| 5,049,824 | 9/1991 | Suzuki et al. | 324/660 |
| 5,049,826 | 9/1991 | Sasao | 324/662 |
| 5,051,238 | 9/1991 | Umetsu et al. | 422/64 |
| 5,053,715 | 10/1991 | Andermo | 324/662 |
| 5,057,823 | 10/1991 | Dyer et al. | 340/620 |
| 5,063,790 | 11/1991 | Freeman et al. | 73/864.14 |
| 5,083,283 | 1/1992 | Imai et al. | 364/497 |
| 5,084,242 | 1/1992 | Sakuma et al. | 422/100 |
| 5,087,423 | 2/1992 | Ishibashi | 422/67 |
| 5,096,670 | 3/1992 | Harris et al. | 422/65 |
| 5,101,673 | 4/1992 | Uffenheimer | 73/864.22 |
| 5,104,621 | 4/1992 | Pfost et al. | 422/67 |
| 5,104,624 | 4/1992 | Labriola | 422/100 |
| 5,104,808 | 4/1992 | Laska et al. | 436/48 |
| 5,108,703 | 4/1992 | Pfost et al. | 422/65 |
| 5,114,679 | 5/1992 | Reifler et al. | 422/100 |
| 5,116,578 | 5/1992 | Baxter | 422/63 |
| 5,136,250 | 8/1992 | Abdelli | 324/661 |
| 5,137,693 | 8/1992 | Mawhirt | 422/104 |
| 5,141,871 | 8/1992 | Kureshy et al. | 436/47 |
| 5,149,654 | 9/1992 | Gross et al. | 435/287 |
| 5,158,748 | 10/1992 | Obi et al. | 422/100 |
| 5,158,895 | 10/1992 | Ashihara et al. | 436/526 |
| 5,164,318 | 11/1992 | Sato et al. | 435/288 |
| 5,167,922 | 12/1992 | Long | 422/58 |
| 5,167,926 | 12/1992 | Kimura et al. | 422/67 |
| 5,175,086 | 12/1992 | Takekawa et al. | 435/7.92 |
| 5,178,834 | 1/1993 | Kagayama et al. | 422/65 |
| 5,187,990 | 2/1993 | Magnussen et al. | 73/864.18 |
| 5,192,505 | 3/1993 | Sakagami | 422/64 |
| 5,204,264 | 4/1993 | Kaminer | 436/8 |
| 5,204,269 | 4/1993 | Barker et al. | 436/47 |
| 5,213,761 | 5/1993 | Sakagami | 422/63 |

FOREIGN PATENT DOCUMENTS

| Document # | Date | Country |
|---|---|---|
| 00013452 | 7/1980 | European Pat. Off. |
| 02446480 | 8/1980 | European Pat. Off. |
| 02049179 | 12/1980 | European Pat. Off. |
| 02065298 | 6/1981 | European Pat. Off. |
| 02068542 | 8/1981 | European Pat. Off. |
| 00035320 | 9/1981 | European Pat. Off. |
| 03016294 | 10/1981 | European Pat. Off. |
| 00041378 | 12/1981 | European Pat. Off. |
| 00043079 | 1/1982 | European Pat. Off. |
| 03029440 | 2/1982 | European Pat. Off. |
| 03134005 | 4/1982 | European Pat. Off. |
| 00051541 | 5/1982 | European Pat. Off. |
| 00052006 | 5/1982 | European Pat. Off. |
| 00054262 | 6/1982 | European Pat. Off. |
| 00061317 | 9/1982 | European Pat. Off. |
| 02095403 | 9/1982 | European Pat. Off. |
| 00062251 | 10/1982 | European Pat. Off. |
| 00074102 | 3/1983 | European Pat. Off. |
| 00078948 | 5/1983 | European Pat. Off. |
| 00083474 | 7/1983 | European Pat. Off. |
| 00083651 | 7/1983 | European Pat. Off. |
| 00089346 | 9/1983 | European Pat. Off. |
| 0100663 | 2/1984 | European Pat. Off. |
| 00101192 | 2/1984 | European Pat. Off. |
| 00103622 | 3/1984 | European Pat. Off. |
| 02125962 | 3/1984 | European Pat. Off. |
| 00107580 | 5/1984 | European Pat. Off. |
| 0109613 | 5/1984 | European Pat. Off. |
| 03242459 | 5/1984 | European Pat. Off. |
| 03242460 | 5/1984 | European Pat. Off. |
| 02131168 | 6/1984 | European Pat. Off. |
| 02131946 | 6/1984 | European Pat. Off. |
| 03448121 | 7/1984 | European Pat. Off. |
| 02136953 | 9/1984 | European Pat. Off. |
| 00129450 | 12/1984 | European Pat. Off. |
| 03500639 | 7/1985 | European Pat. Off. |
| 00185330 | 6/1986 | European Pat. Off. |
| 00192968 | 9/1986 | European Pat. Off. |
| 00193016 | 9/1986 | European Pat. Off. |
| 03605695 | 9/1986 | European Pat. Off. |
| 0212455 | 3/1987 | European Pat. Off. |
| 0216026 | 4/1987 | European Pat. Off. |
| 0216177 | 4/1987 | European Pat. Off. |
| 00222466 | 5/1987 | European Pat. Off. |
| 02591344 | 6/1987 | European Pat. Off. |
| 00231430 | 8/1987 | European Pat. Off. |
| 00236928 | 9/1987 | European Pat. Off. |

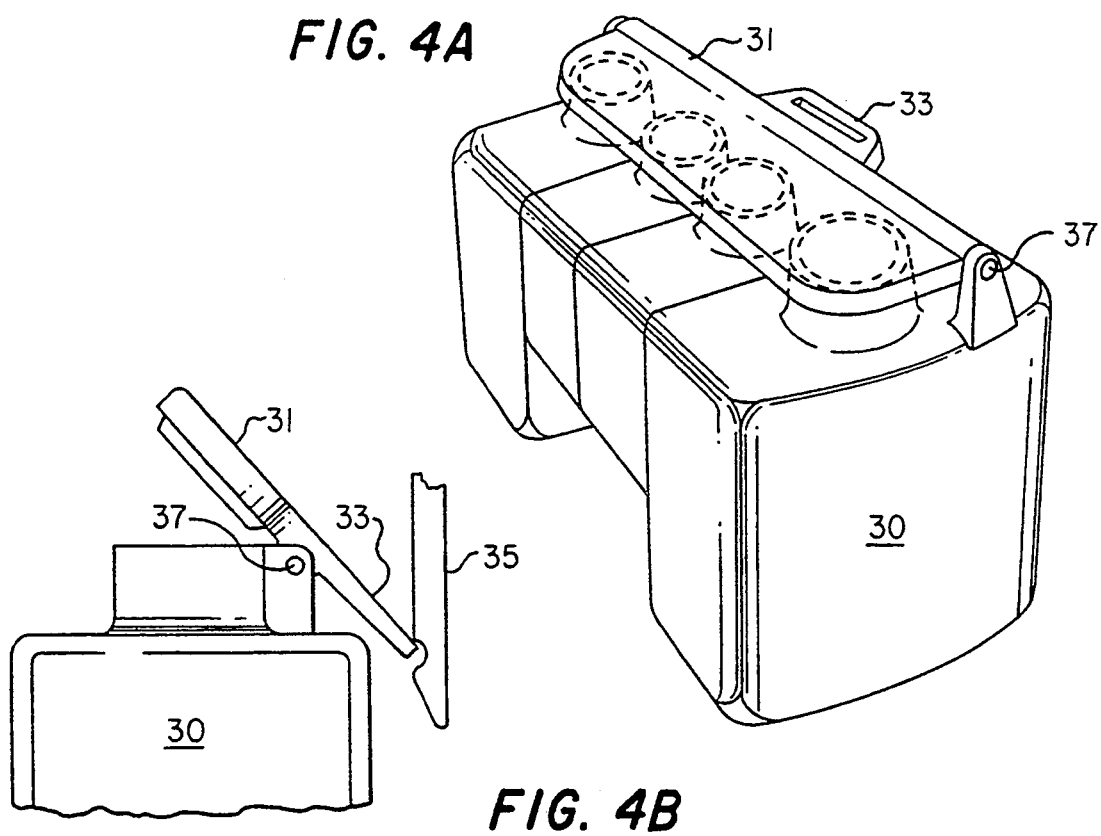
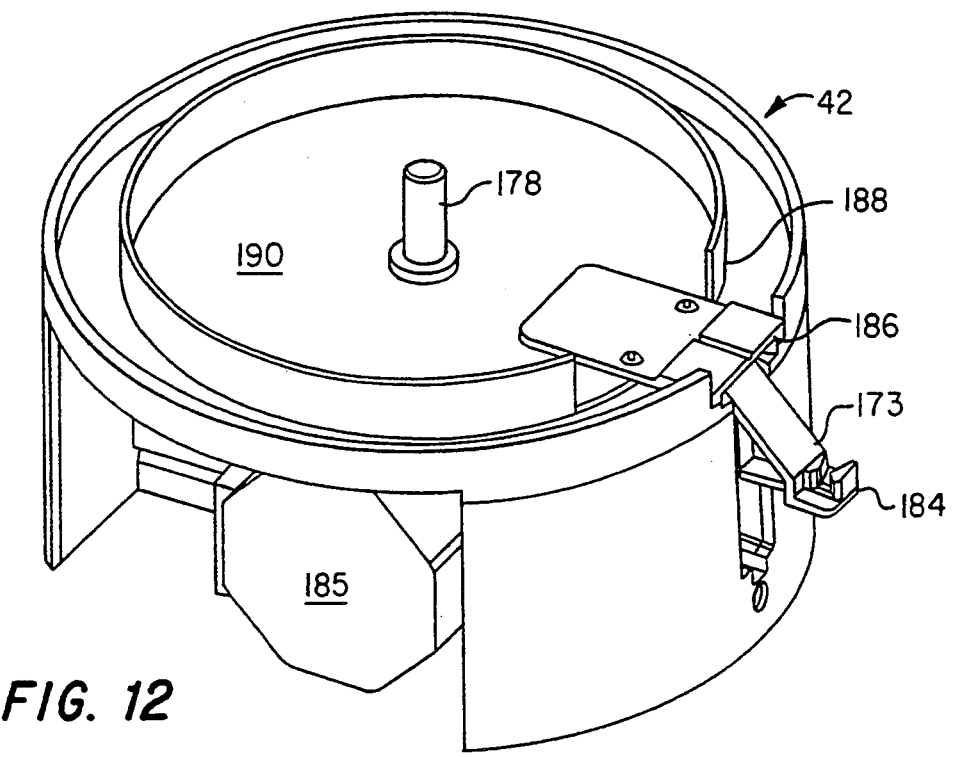

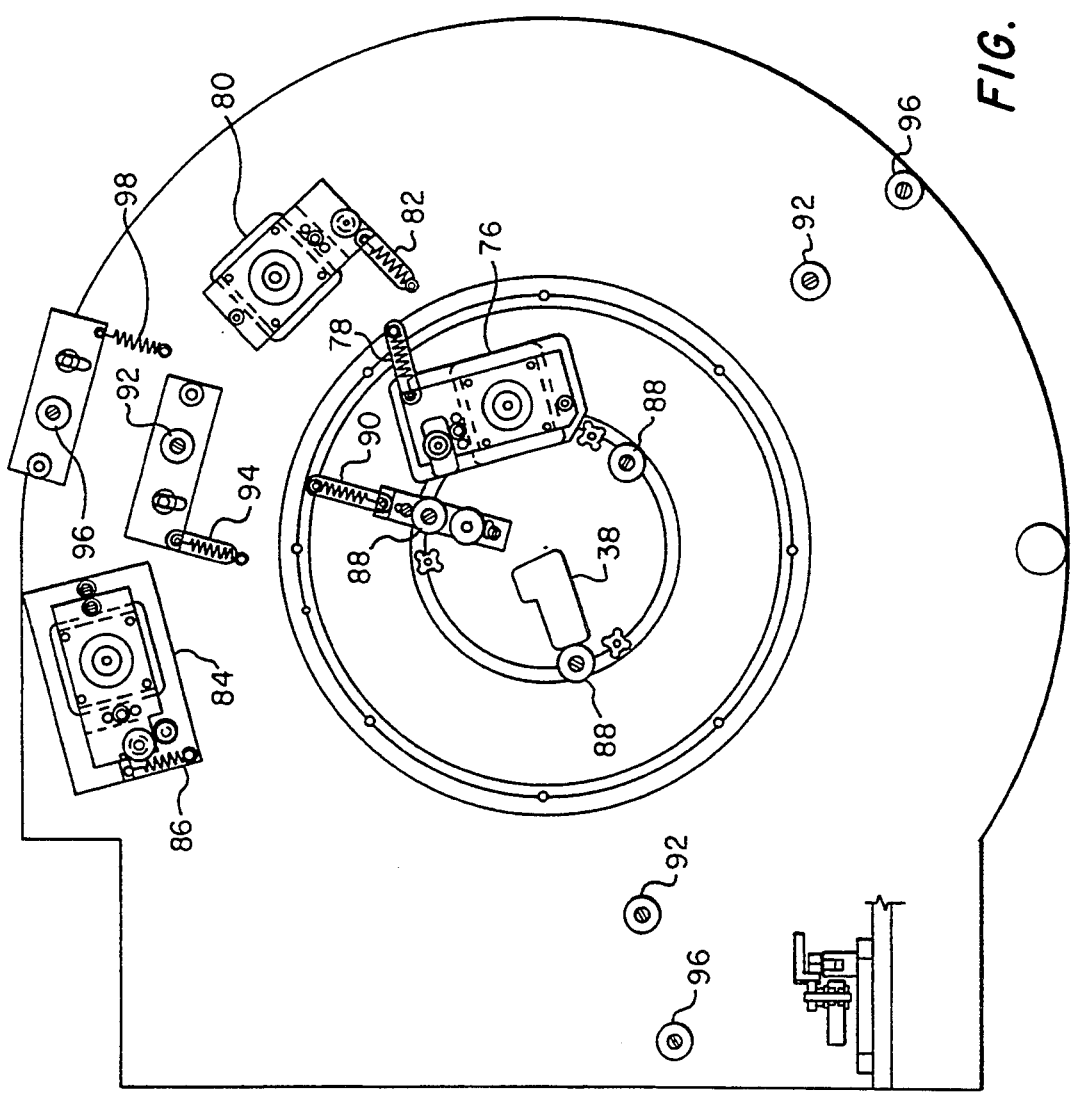

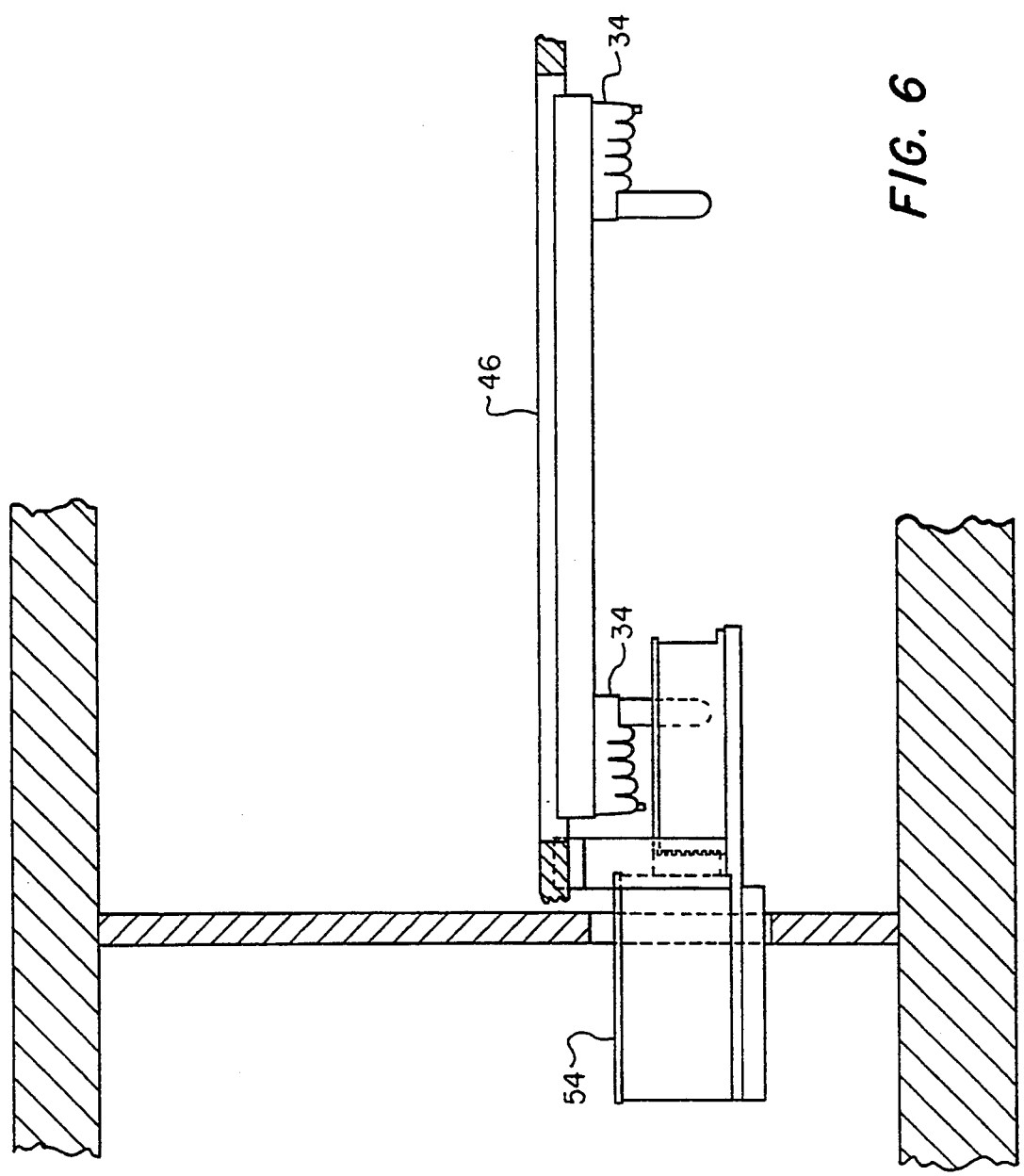

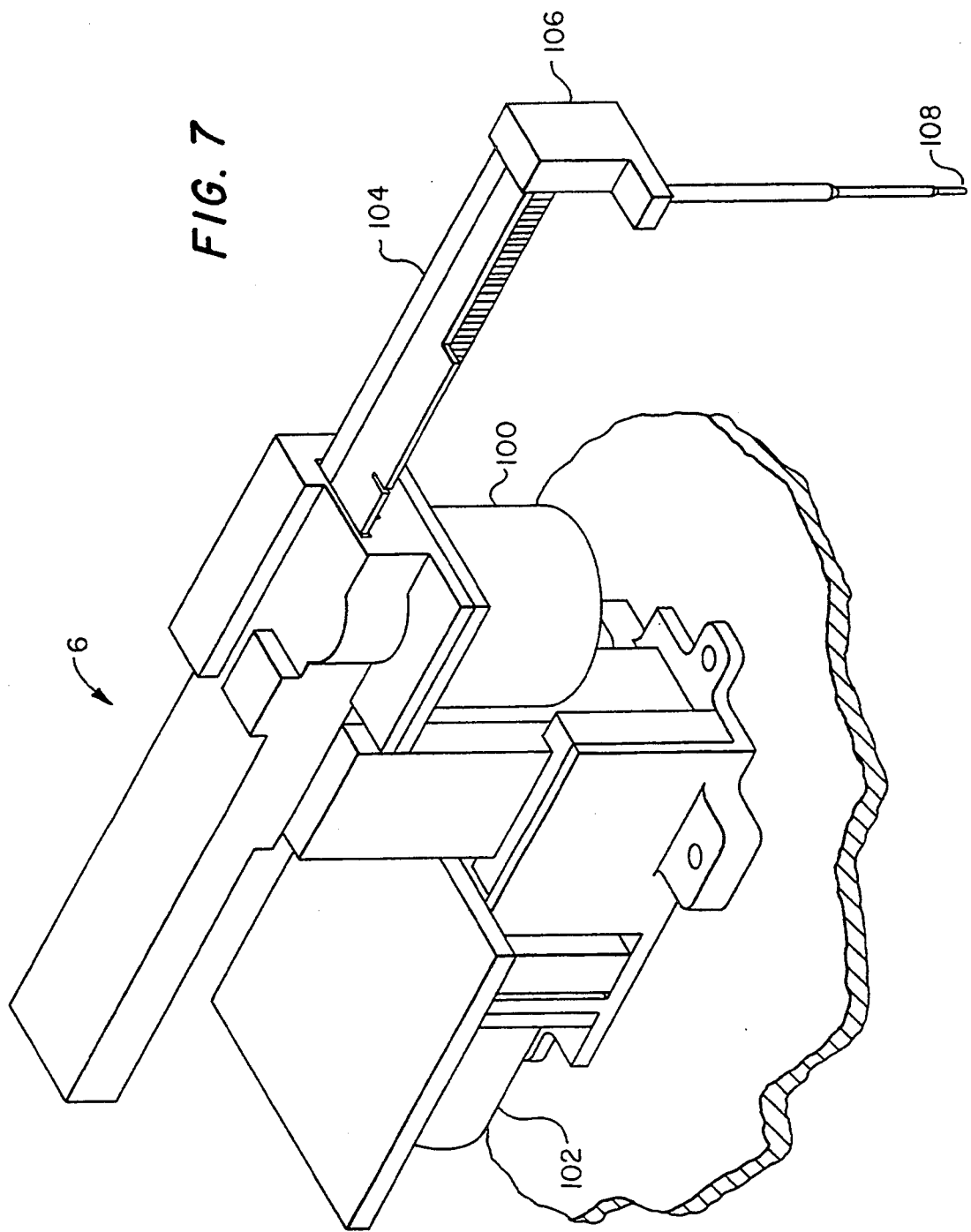

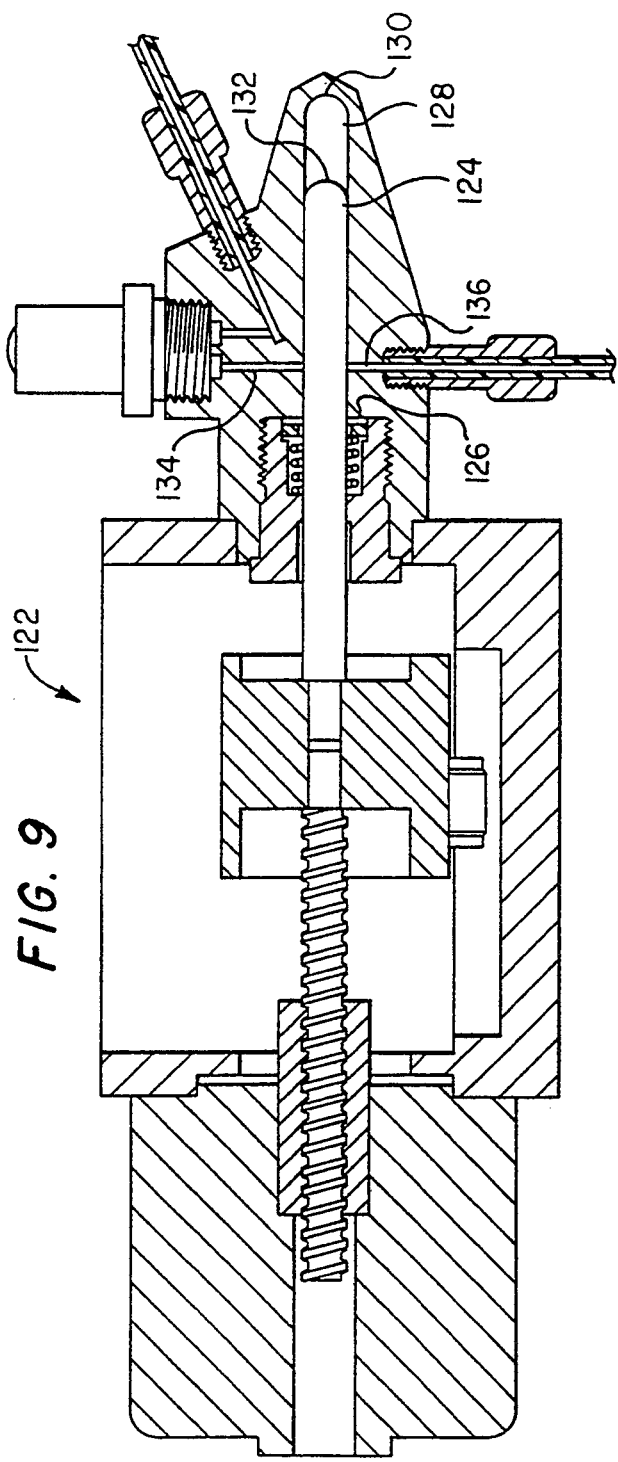
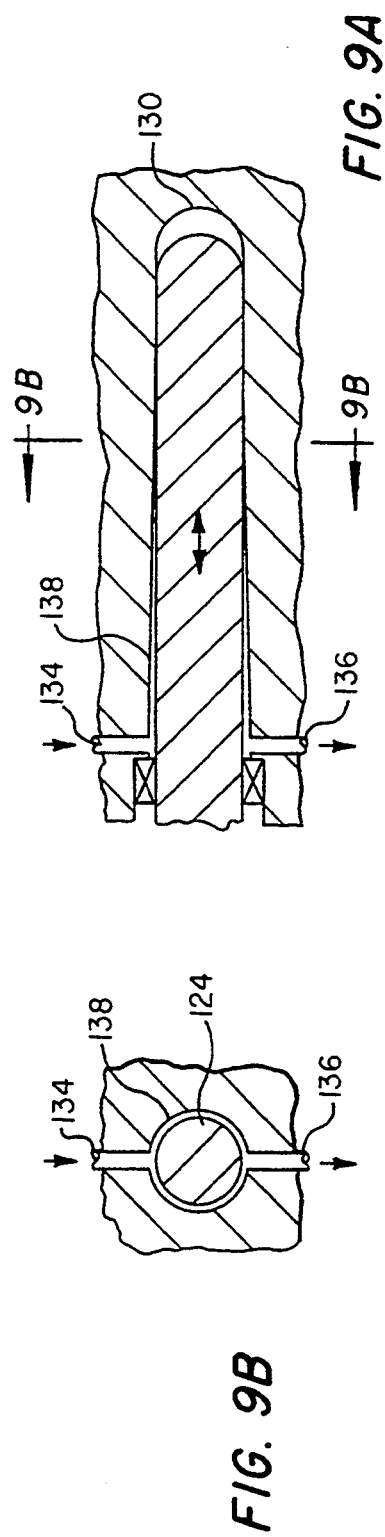
FIG. 9
FIG. 9A
FIG. 9B

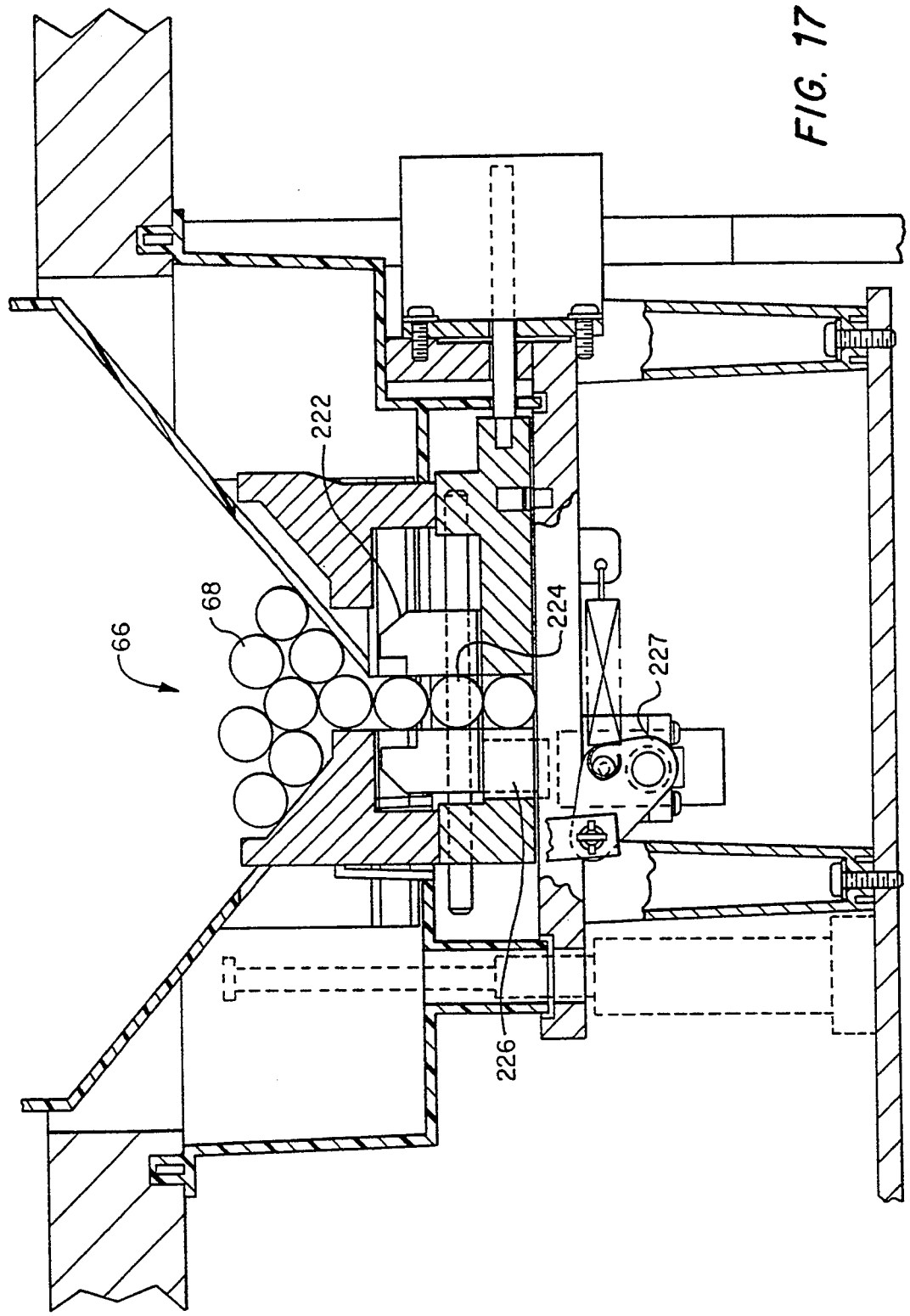

FIG. 26
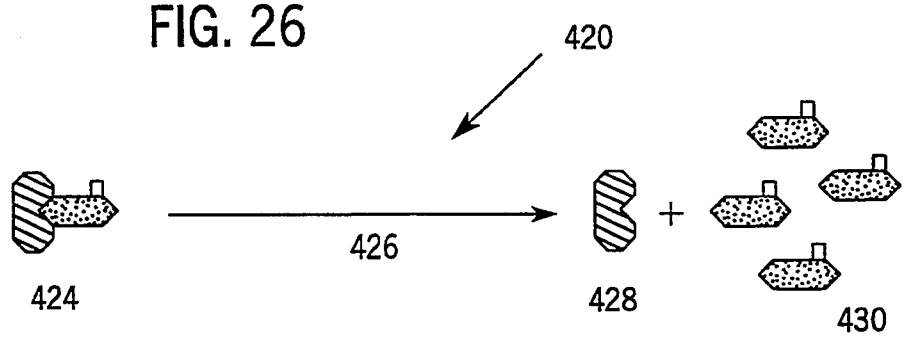
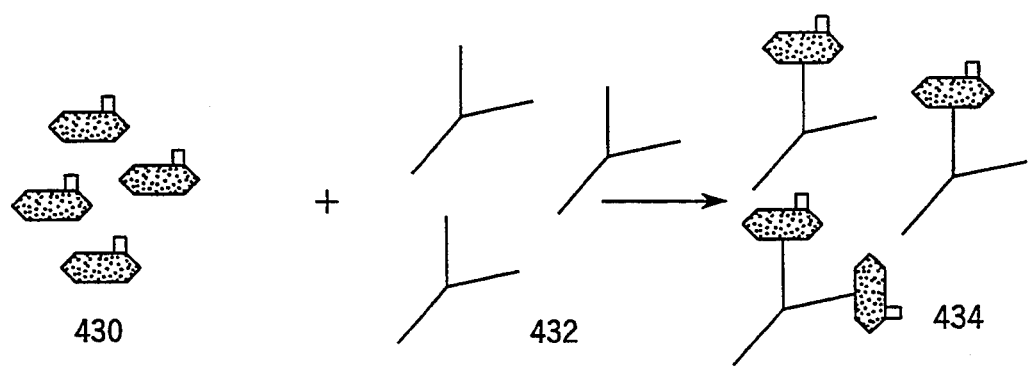
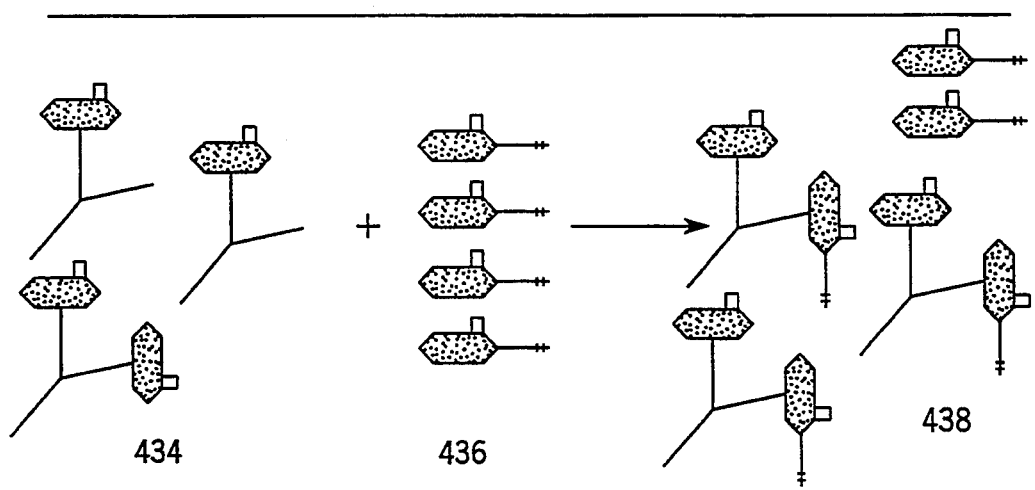

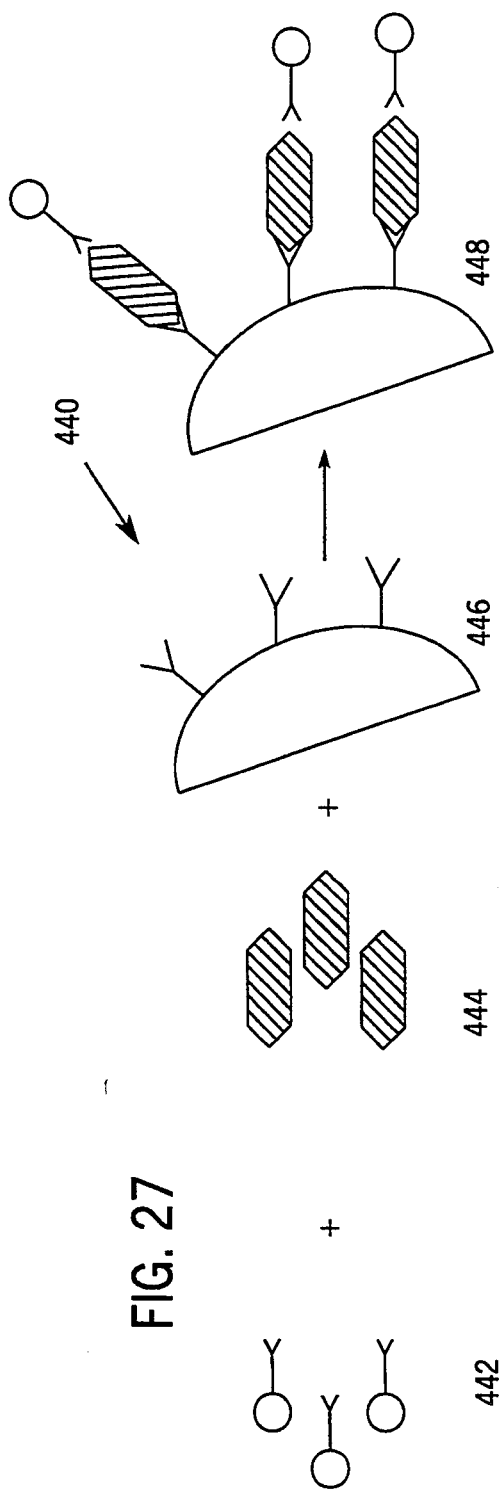
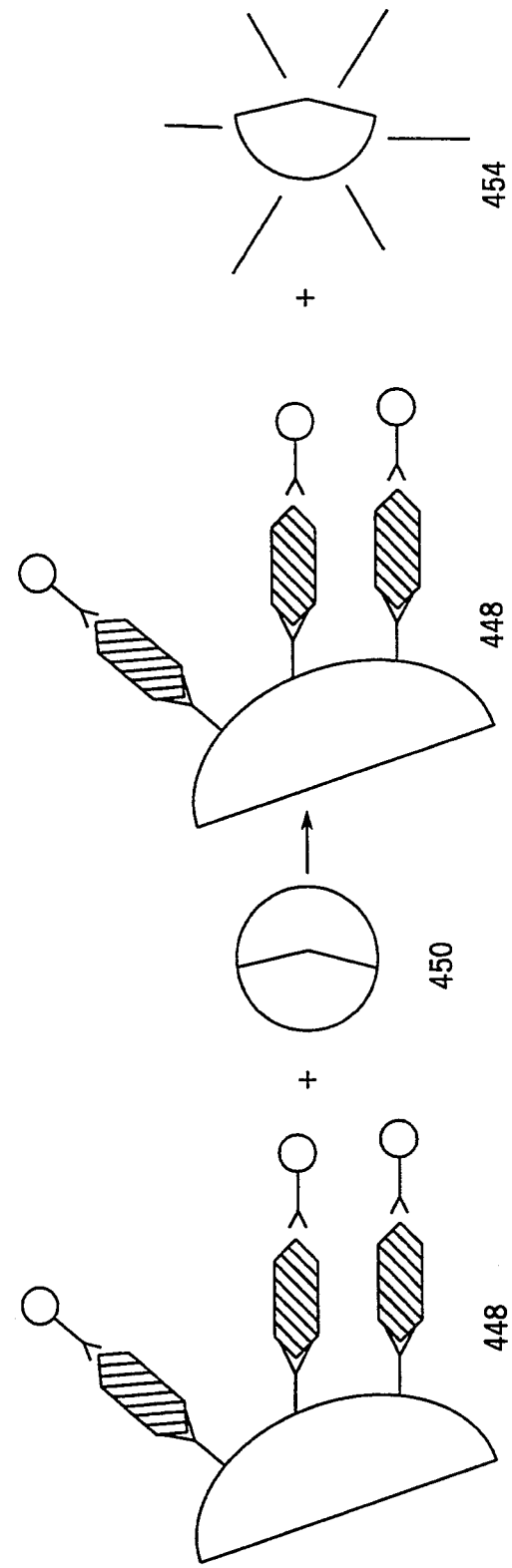
FIG. 27

FIG. 28
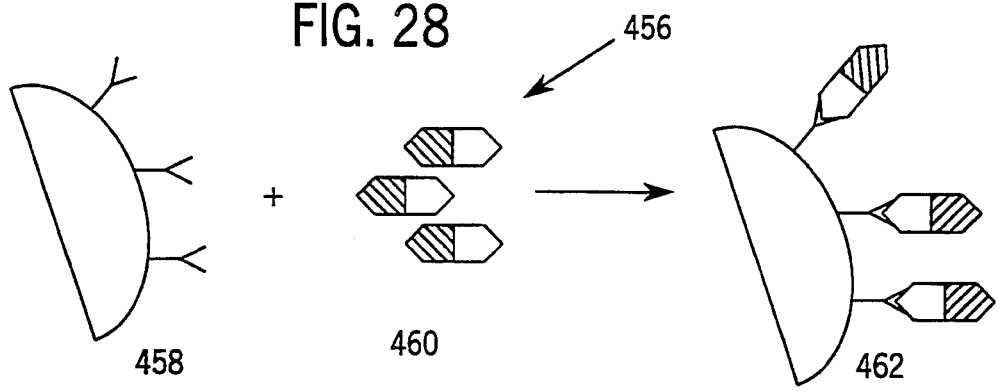
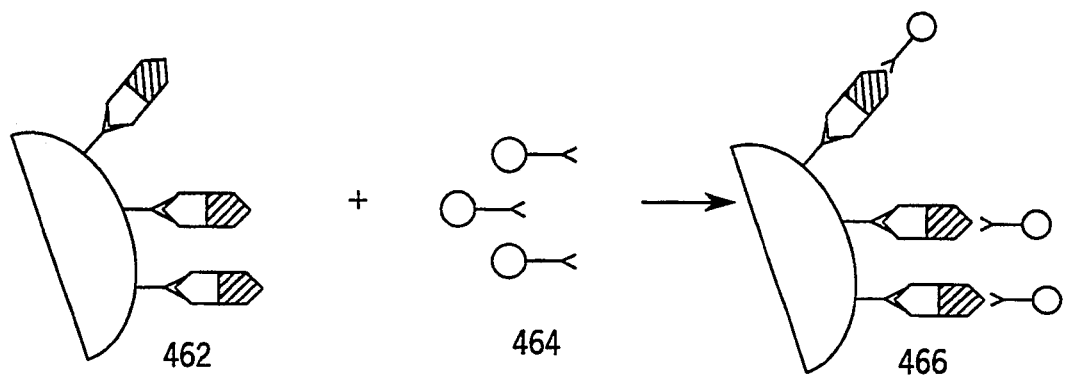
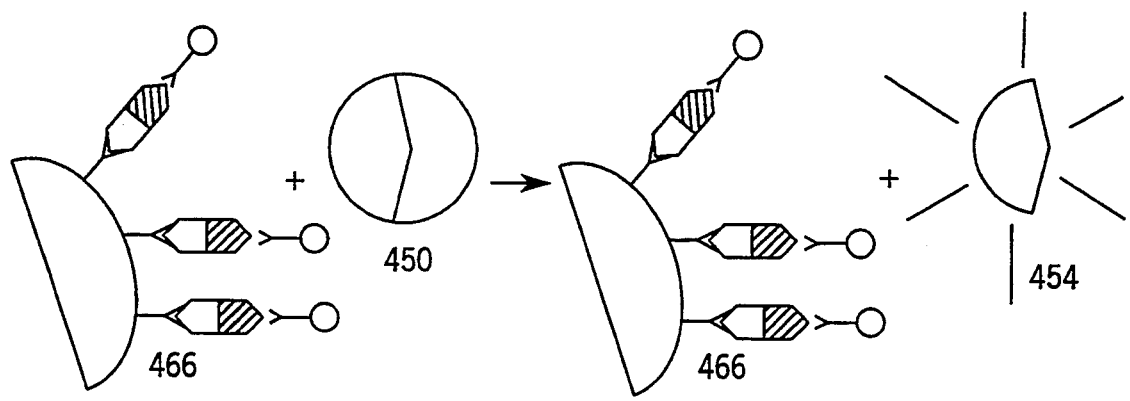

AUTOMATED CONTINUOUS AND RANDOM ACCESS ANALYTICAL SYSTEM

This patent application is a continuation of U.S. patent application Ser. No. 07/859,218, filed on Mar. 27, 1992, now abandoned.

FIELD OF THE INVENTION

The present invention relates to an automated analytical system and methods for the analysis of liquid test samples. In another aspect, the invention is related to a continuous and random access system which is capable of simultaneously performing a plurality of assays, particularly heterogeneous and/or homogeneous immunoassays.

BACKGROUND OF THE INVENTION

Although various known clinical analyzers for chemical, immunochemical and biological testing of samples are available, clinical technology is rapidly changing due to increasing demands in the clinical laboratory to provide new levels of service. These new levels of service must be more cost effective to decrease the operating expenditures such as labor cost and the like, and must provide shorter turnaround time of test results to reduce the patient's length of stay in the hospital as well as improve efficiency of outpatient treatment. Modernization of analytical apparatus and procedures demands consolidation of work stations to meet the growing challenge placed on clinical laboratories.

Generally, analysis of a test sample involves the reaction of test samples with one or more reagents with respect to one or more analytes wherein it is frequently desired that the analysis be performed on a selective basis with respect to each test sample. However, due to the high demands placed on clinical laboratories regarding not only volume throughput but also the number and frequency of various analyses, there is a need to provide an automated analysis system which is capable of combining accurate analytical results, high throughput, multiple test menu versatility as well as low reagent consumption.

Typically, analysis of a test sample involves forming a reaction mixture comprising the test sample and one or more reagents, and the reaction mixture is then analyzed by an apparatus for one or more characteristics of the test sample. Reliance on automated clinical analyzers improves the efficiency of the laboratory procedures inasmuch as the technician has fewer tasks to perform. Automated clinical analyzers provide results much more rapidly while frequently avoiding operator or technician error, thus placing emphasis on accuracy and repeatability of a variety of tests. Automated clinical analyzers presently available for routine laboratory tests include a transport or conveyor system designed to transport containers of sample liquids between various operating stations. For example, a reaction tube or cuvette containing a test sample may pass through a reagent filling station, mixing station, reaction forming station, detection stations, analysis stations, and the like. However, such transport systems are not flexible in that transport is in one direction and the reaction tubes or cuvettes, once inserted into the apparatus, must pass through without access before analysis occurs.

Automated immunoassay analyzers have been provided such as the Abbott IMx ® analyzer and the Abbott TDx ® analyzer (Abbott Laboratories, Abbott Park, Illinois, USA) which utilize procedures involving a variety of different assay steps but typically rely on detection and measurement of optical changes in a reaction mixture during the assay process. For example, a number of well-known techniques using single or multi-wavelength fluorescence include fluorescent polarization immunoassays (FPIA) employing homogeneous immunoassay techniques, microparticle enzyme immunoassays (MEIA) employing heterogeneous immunoassay techniques, and the like. The MEIA technology, such as that used on the Abbott IMx analyzer, is used for high and low molecular weight analytes requiring greater sensitivity, and FPIA technology, such as that used on the Abbott TDx analyzer, is used primarily for lower molecular weight analytes. A front surface fluorometer is used to quantify a fluorescent product generated in the MEIA assays, while a fluorescence polarization optical system is used to quantify the degree of tracer binding to antibody in the FPIA assays. The test samples are automatically processed in the Abbott IMx analyzer and Abbott TDx analyzer by a robotic arm with a pipetting probe and a rotating carousel which positions the samples for processing. These instruments are compact table-top analyzers which offer fully automated, walk-away immunoassay testing capabilities for both routine and specialized immunoassays. These nonisotopic methods eliminate radioactivity disposal problems and increase reagent shelf life while meeting the diverse requirements of a multitude of different assays.

Instead of loading the test sample into a container and obtaining sequential testing, such as one direction only systems as described above, the Abbott IMx analyzer and the Abbott TDx analyzer, often referred to as batch analyzers, permit the analysis of multiple samples and provide for access to the test samples for the formation of subsequent reaction mixtures. However, such batch analyzers permit only one type of analysis at a time. In a random access analyzer, not only can multiple test samples be analyzed, but multiple analytes may be analyzed from each test sample. Another common feature of presently available sequential and random access analyzers is the inclusion of various reagents within the apparatus itself or placed near the apparatus for pipetting purposes. Liquid reagents, in bulk form, are selected for the various types of tests which are to be performed on the test sample, and are stored in or near the apparatus. The reagent delivery units, such as pumps and the like, along with valves, control and pipette mechanisms, are included in these automated analyzers so that different reagents can be mixed according to the type of test to be performed. The Abbott IMx analyzer automatically performs all the steps required for analysis of test samples and includes numerous checks of the subsystems to insure that the assay can be run to completion and that results are valid. Quantification of the fluorescence intensity in the MEIA method and polarization in the FPIA method, as well as the final data reduction, are also fully automated on the analyzer. Results are printed by the analyzer and can be accessed through suitable means for automatic data collection by a laboratory computer.

Automated analytical apparatus for performing homogeneous assays, the detection of precipitate formed by reaction between antigens and antibodies in a test sample cell to form light scattering centers, and methods and apparatus for detecting immunological agglutination reactions are also known in the art. Such apparatus and methods include, for example, the steps of measuring light absorption of the liquid medium with antibody before and after the antigen-antibody reaction by using light which is absorbable by the antibody, and calculating the difference of the absorptions. In this way, the presence or absence of agglutination can be detected based on the fact that the agglutination reaction reduces the concentration of antibody, which affects the light absorption of the liquid medium. As is typical of methods and apparatus for performing homogeneous assays, these procedures do not require separation of a solid phase from the reaction mixture for further analysis.

Heterogeneous assays are also known through the use of a sample analyzer for quantitating relatively small amounts of clinically significant compounds in a liquid test sample by focusing a light source onto the sample so that, for example, fluorescent particles in the sample cause fluorescent conditions, the intensity of which is the function of the intensity of the light beam and the concentration of fluorescent particles in the sample. A detector senses photons forming the fluorescent emissions of the particles when excited by the light beam. The introduction of a solid phase material into the sample requires subsequent separation of the solid phase from the reaction mixture for further analysis and before the fluorescent emissions can be detected and measured.

Recently, apparatus and methods have been proposed for performing, selectively on the same sample, various homogeneous and heterogeneous assays concurrently in a random access fashion. Such apparatus and methods provide for the analysis of a plurality of liquid samples wherein each sample is analyzed with respect to at least one analyte utilizing both homogeneous and heterogeneous assay techniques.

Accordingly, since such previously described automated analyzers do not contemplate an automated analytical system for simultaneously performing both homogeneous and heterogeneous assays in a continuous and random access fashion utilizing a commonality of various process work stations and transfer means, there is a need to provide an automated analytical system having these features and sufficient flexibility to meet the growing needs of the modern clinical laboratory.

SUMMARY OF THE INVENTION

The automated analytical system of the present invention is capable of simultaneously performing two or more assays on a plurality of test samples in a continuous and random access fashion. In particular, the automated immunoassay analytical system apparatus of the invention can be viewed as a microprocessor-based system of integrated subassemblies with different groups of assays being run through separate and changeable software modules. The microprocessor based system uses robotic arm pipetters with two degrees of freedom and bidrectional rotating carousels to process samples. Critical assay steps such as incubations, washes and specimen dilution are performed automatically by the instrument as scheduled.

According to the invention, automated, continuous and random access analytical system capable of simultaneously effecting multiple assays of a plurality of liquid samples is provided, and enables performing a method wherein various assays are scheduled for a plurality of liquid samples. Through kitting means the present system is capable of creating a unit dose disposable by separately transferring liquid sample and reagents to a reaction vessel without initiation of an assay reaction sequence. From the kitting means multiple, kitted unit dose disposables are transferred to a process area, wherein an aliquot is mixed for each independent sample with one or more liquid reagents at different times in a reaction vessel to form independent reaction mixtures. Independent scheduling of such kitting and mixing is achieved during incubation of the multiple reaction mixtures, simultaneously and independently.

The system of the present invention is capable of performing more than one scheduled assay in any order in which plurality of scheduled assays are presented. The incubated reaction mixtures are analyzed independently and individually by at least two assay procedures which are previously scheduled.

The automated, continuous and random access analytical system apparatus of this invention is comprised of a front end carousel assembly inclusive of a sample cup carousel, a reagent pack carousel and a reaction vessel carousel mounted concentrically and serviced by a transfer piperting means suitable for kitting and/or mixing reagents with a sample. The kitted and pipetted reaction vessels are transferred through a transfer station which provides means for transferring the kitted and pipetted reaction vessels to a processing work station, which includes a controlled environment for maintaining temperature and provides timing for mixing of reagents and incubation. At least two assay procedural apparatus are provided which are scheduled for the various samples and kitted reagents in a unit dose disposable means for analyzing the incubated reaction mixtures. The unit dose disposable reaction vessels are removed from the process carousel by operation of the transfer station, which includes means for removing the disposable reaction vessel from the system.

Additional advantages and novel features of the invention will be set forth in part in the description which follows, and will become apparent to those skilled in the art upon examination of the following or may be learned by practice of the invention. The objects and advantages of the invention may be obtained by means of the exemplary combinations more particularly pointed out in the following specification and appended claims, including all equivalents thereof.

DETAILED DESCRIPTION OF THE INVENTION

Definitions

The following definitions are applicable to the present invention:

The term "test sample" as used herein, refers to a material suspected of containing the analyte. The test sample can be used directly as obtained from the source or following a pretreatment to modify the character of the sample. The test sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid or the like. The test sample can be pretreated prior to use, such as preparing plasma from blood, diluting viscous fluids, or the like; methods of treatment can involve filtration, distillation, concentration, inactivation of interfering components, and the addition of reagents. Besides physiological fluids, other liquid samples can be used such as water, food products and the like for the performance of environmental or food production assays. In addition, a solid material suspected of containing the analyte can be used as the test sample. In some instances it may be beneficial to modify a solid test sample to form a liquid medium or to release the analyte.

The term "analyte" or "analyte of interest" as used herein, refers to the compound or composition to be detected or measured and which has at least one epitope or binding site. The analyte can be any substance for which there exists a naturally occurring binding member or for which a binding member can be prepared. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), virus particles and metabolites of or antibodies to any of the above substances. The term "analyte" also includes any antigenic substances, haptens, antibodies, macromolecules and combinations thereof.

The term "analyte-analog" as used herein refers to a substance which cross-reacts with an analyte-specific binding member, although it may do so to a greater or lesser extent than does the analyte itself. The analyte-analog can include a modified analyte as well as a fragmented or synthetic portion of the analyte molecule, so long as the analyte-analog has at least one epitopic site in common with the analyte of interest. An example of an analyte-analog is a synthetic peptide sequence which duplicates at least one epitope of the whole-molecule analyte so that the analyte-analog can bind to an analyte-specific binding member.

The term "binding member" as used herein refers to a member of a binding pair, i.e., two different molecules wherein one of the molecules specifically binds to the second molecule through chemical or physical means. In addition to antigen and antibody binding pair members, other binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, binding pairs can include members that are analogs of the original binding member, for example, an analyte-analog or a binding member made by recombinant techniques or molecular engineering. If the binding member is an immunoreactant it can be, for example, a monoclonal or polyclonal antibody, a recombinant protein or recombinant antibody, a chimeric antibody, a mixture(s) or fragment(s) of the foregoing, as well as a preparation of such antibodies, peptides and nucleotides for which suitability for use as binding members is well known to those skilled in the art.

The term "detectable moiety" as used herein refers to any compound or conventional detectable chemical group having a detectable physical or chemical property and which can be used to label a binding member to form a conjugate therewith. Such detectable chemical group can be, but is not intended to be limited to, enzymatically active groups such as enzymes, enzyme substrates, prosthetic groups or coenzymes; spin labels; fluorescers and fluorogens; chromophores and chromogens; luminescers such as chemiluminescers and bioluminescers; specifically bindable ligands such as biotin and avidin; electroactive species; radioisotopes; toxins; drugs; haptens; DNA; RNA; polysaccharides; polypepetides; liposomes; colored particles and colored microparticles; and the like.

The term "continuous access" as used herein, refers to the ability to add additional test samples or reagents to the automated analytical system of the present invention without the interruption of assays which are being performed by the automated analytical system of the present invention at the time of such addition.

The term "random access" as used herein, refers to the ability of the automated analytical system of the present invention to simultaneously perform more than one scheduled assay in any order in which such plurality of scheduled assays are presented into the automated analytical system of the present invention.

The term "simultaneous" as used herein, refers to the ability of the automated analytical system of the present invention to independently perform two or more scheduled assays at the same time.

The term "kitting" as used herein refers to the ability of the automated analytical system of the present invention to create a unit dose disposable by separately transferring test samples and reagents to a reaction vessel of the present invention without initiation of an assay reaction sequence.

The term "quat" refers to a polycationic material solution for assays which use these materials which are not an antibody or antigen to capture the analyte from the sample on the matrix of, for example, MEIA cartridge. In the present inventive system, quat is dispensed to the matrix during test processing, prior to the transfer of the reaction mixture from the reaction vessel.

The term "flexible protocols" refers to the variety of different assay protocols capable of being processed in accordance with the inventive system. Examples include MEIAs configured in 1- and 2-step sandwich and competitive assay formats; order of activity processing, including the ability to initiate sample processing for both MEIAs and FPIAs on the front-end carousel prior to transfer onto the process carousel; variable incubation periods; optical read formats and wash sequences. This contrasts to some prior art, known random access systems which force all assay protocols to adhere to a strict "lock-step" format, in which assay configuration (i.e. 1- versus 2-step formats), activity order, incubation timing, and other similar protocols are fixed by the instrument.

DESCRIPTION OF PREFERRED EMBODIMENTS

The following provides a description of the automated analytical system of the invention in operation, and a description of the use of such system in the method for the analysis of test samples as provided by the instant invention.

Scheduler

In the present invention, a system scheduler generates and optimizes the workload for the system's mechanical resources from all the tests ordered to run on the system. The main goal of the scheduler is to keep the system's resources from sitting idle while there are tests remaining to be processed by the system. Keeping each of the resources busy also minimizes the time required by the instrument to perform the tests.

A high-level view of the scheduling process can be broken into two steps: 1) proper scheduling of each of the activities in a test is ensured before the test is kitted, and 2) an attempt to perform each test activity prior to its original scheduled execution time, to minimize resource idle time and increase test throughput in the system.

To enable scheduling a test in advance of its performance in the system, each test's assay protocol contains several timing parameters used in the scheduling process. Each activity of the test contains time values which the scheduler uses to determine which resources the activity requires and the time period that these resources are needed. Also, each activity in the test can be tied to other activities by incubation periods. These incubation periods, which are dictated by the chemistry of the assay, help the scheduler determine the amount of time that must elapse between the execution of two activities. Each incubation period in the assay protocol provides for the minimum and maximum time that may elapse between the execution of each activity. These limits are referred to in the scheduling process as the incubation window for the activities.

In the inventive system, the operator chooses the order that tests are prepared to run on the instrument by selecting the placement of samples on the instrument. The sample placed closest to the pipette station is the first sample prepared to run on the instrument. To guard against evaporation, a test will not be prepared until the scheduler ensures that all resources used by the test's activities will be available at the required times set forth in the test's assay protocol. Preparation of a particular test will be postponed whenever an activity of another test already in the instrument has a resource scheduled at the time it is needed by an activity on that test. The sample preparation area of the instrument will remain idle until the test can be scheduled without conflicting with tests already in the instrument. When proper scheduling of the test can be achieved, the test will be prepared and transferred into the process area.

The second step in the scheduling process is to optimize the workload for each system resource to minimize both the resource's idle time and the time required to perform the resource's workload. Once tests are transferred into the process area, the scheduler optimizes the existing schedule for each resource. At predetermined intervals, the scheduler examines the next interval of work for each resource. If there is any idle time in this interval, the scheduler attempts to minimize the idle time by rearranging the resource's workload to eliminate idle time, providing the activities remain within their allowed incubation windows. When optimization of this interval is complete, this section of the workload is performed by the resource at the designated times.

The scheduler continues to prepare samples as long as there are samples on the instrument that have tests ordered to be run. Optimization of the resources' workloads will continue until all tests transferred into the system have finished processing.

Stat Procedure

The inventive system allows special priority handling of specific samples identified by the user as being star samples. A star sample, as defined by the inventive system, is a sample that must be processed by the instrument in the shortest amount of time possible. Special handling of star samples occurs both in the front sample entry area and in the processing area of the instrument.

In the inventive system, the operator chooses the order that tests are prepared to run on the instrument by selecting the placement of samples on the instrument. The sample placed closest to the pipette station is the first sample prepared to run on the instrument. This pattern of sample preparation is interrupted whenever the user places a stat test on the instrument. Whenever a stat test is ordered, the system will finish preparing the test on the current sample, and then move directly to the stat sample to prepare all its tests. To guard against evaporation, sample preparation will not begin for a test before proper scheduling of the test's activities in the processing area is ensured.

The system scheduling algorithm is also modified for star processing. The scheduling algorithm used for normal tests attempts to maximize the number of tests processed in the instrument each hour. This occurs by allowing sufficient time between test activities to enable other tests' activities to be performed in these gaps. The scheduling approach used for stat tests attempts to process this one test in the shortest amount of time possible. Each activity of a star test is scheduled at the earliest possible time of execution as defined in the test's assay definition. When all activities of a test are guaranteed proper scheduling in the instrument, sample preparation of the test will begin. After all tests on the stat sample are prepared, the system will return to the sample it was working on before it serviced the stat.

Stat tests receive special consideration in the processing area when there is idle time in a resource's workload. At predetermined intervals, the scheduler examines the next interval of work allocated to each resource in the processing area of the system. If there is any idle time during this interval, the scheduler attempts to minimize it by rearranging the resource's workload. Test activities scheduled for this resource that can be performed earlier than they are currently scheduled, as defined by their assay protocols, are moved forward to fill the idle time. Star test activities are the first candidates to be pulled forward in the workload, thus further decreasing the amount of time needed to process the star test in the instrument.

The system star test handling algorithms have been shown to allow star tests to be processed in the minimum amounts of time possible, without having a negative effect on the instrument's overall throughput of tests per hour.

The automated analytical system of the present invention is capable of performing various assays employing various detection systems known in the art and include, but are not intended to be limited to, spectrophotometric absorbance assay such as end-point reaction analysis and rate of reaction analysis, turbidimetric assays, nephelometric assays, radiative energy attenuation assays (such as those described in U.S. Pat. No. 4,496,293 and U.S. Pat. No. 4,743,561 and incorporated herein by reference), ion capture assays, colorimetric assays, fluorometric assays, electrochemical detection systems, potentiometric detection systems, amperometric detection system and immunoassays. Immunoassays include, but are not intended to be limited to, heterogeneous immunoassays such as competitive immunoassays, sandwich immunoassays, immunometric immunoassays, and the like, where the amount of a detectable moiety employed therein can be measured and correlated to the amount of analyte present in a test sample.

Generally, in a spectrophotometric assay, such as those performed on the Abbott Spectrum ® clinical analyzer and the Abbott Spectrum Series II ® clinical analyzer (Abbott Laboratories, Abbott Park, Ill., USA) the interaction in an assay solution between the analyte to be determined and a reagent system specific for the analyte produces a detectable change in the transmittive properties of the assay solution. The change in the transmittive properties refers to the amount of light absorbed or scattered by an assay solution within a particular wavelength band when a beam of light of known intensity is passed through the assay solution. The change in the transmittive properties of an assay solution is measured by passing monochromic light having a known intensity though the assay solution and determining the ratio of the intensity of the transmitted or scattered light to the intensity of the incident light. Nearly all analytes either absorb energy of a specific wavelength or interact in an assay solution with a particular reagent system to produce a detectable change in the transmittive properties of the assay solution, characteristics which have resulted in the development of numerous specific spectrophotometric assays. Spectrophotometric assays which rely upon the measurement of the change in the transmittive properties of an assay solution as a measure of an analyte in the assay solution include, for example, assays wherein there is a change in the color of the assay when there is a change in the turbidity of the assay solution, that is, turbidimetric or nephelometric assays.

In a colorimetric assay, the change in the transmittive properties of an assay solution is generally referred to as the absorbance of the assay solution and is dependent upon the change in the color of the assay solution due to the interaction of the analyte to be determined and reagent system specific for the analyte. The absorbance of the assay solution is related to the concentration of the analyte in the assay solution. A colorimetric assay utilizes a chromogenic reagent system capable of interacting in an assay solution with the particular analyte of interest, to produce a detectable change in the transmittive properties, specifically the color, of the assay solution. Numerous chromogenic reagent systems useful in the determination of specific analytes have been developed and are commercially available.

The principle of turbidimetric assays is to determine the amount of light scattered or blocked by particulate matter as light passes though an assay solution. In a turbidimetric assay, the analyte of interest interacts with a reagent system specific for the analyte to form a suspension of particles in the assay solution. As a beam of light having a known intensity is passed through an assay solution, the suspension of particles formed by the interaction of the analyte reagent system blocks or scatters the incident light, thereby reducing the intensity of the light transmitted through the assay solution. The change of the transmittive properties in a turbidimetric assay refers to the decrease in the intensity of the light transmitted through an assay solution, is related to the amount of incident light that is scattered or blocked by the suspension of particles, and depends upon the number of particles present and the cross-sectional area of such particles.

A nephelometric assay is similar to a turbidimetric assay in that the analyte of interest interacts with a reagent system specific for the ligand to form a suspension of particles in the assay solution. In a nephelometric assay, the change in the transmittive properties of the assay solution is also related to the amount of incident light scattered or blocked by the suspension of particles, but unlike a turbidimetric assay wherein the intensity of the light transmitted through the assay solution is measured, the scattered or blocked light is measured at an angle to the light incident to the assay solution. Therefore, in a nephelometric assay the change in the transmittive properties refers to the difference in intensities of light incident to the assay solution and light scattered at an angle to the incident light. Turbidimetric and nephelometric assays are utilized in the analysis of blood, urine, spinal fluid, and the like, for the determination of analytes such as proteins wherein there is no comparable colorimetric assay due to the lack of an effective chromogenic reagent system. Yoe and Klimman in *Photoelectric Chemical Analysis*, Vol. II: *Nephelometry*, Wiley & Sons, Inc., New York, 1929, describe various nephelometric assays.

Various reagents and reagent systems which can be employed for performing spectrophotometric assays on the automated analytical systems of the present invention include, but are not intended to be limited to, those for the simultaneous determination of glucose and urea, such as described in U.S. Pat. No. 5,037,738 and incorporated herein by reference. The simultaneous determination of calcium and phosphorous; the simultaneous determination of cholesterol and triglycerides; determining isoenzymes; determining blood ammonia levels, and the like, can be performed on the apparatus and by the methods of the present invention.

Typically in a fluorometric assay, an analyte in an assay solution is chemically or immunologically transformed into a fluorescent complex or conjugate thereby producing a detectable change in the fluorescent properties of the assay solution. The change in the fluorescent properties of the assay solution is measured by exciting the fluorescent complex or conjugate properties produced with monochromatic light of a wavelength within the excitation wavelength band of the fluorescer, and measuring the intensity of the emitted light at a wavelength within the emission wavelength band of the fluorescer. The fluorescent intensity of the emitted light is related to the concentration of the analyte. However, the intensity of the fluorescence emitted by the assay solution may be inhibited when the ligand to be determined complexes with nonfluorescent interferences such as protein or phosphates present in the sample, or when the sample containing the ligand to be determined has sufficient color so as to act as a filter and thereby reduce the intensity of the emitted fluorescence. It is well recognized that in order to maximize the sensitivity and specificity of a fluorometric assay, these inhibiting factors, if present, must be overcome either by removal of the nonfluorescent interferences or color producing material prior to the analysis, or by compensating for the presence of such factors using an internal standard added to a second aliquot of sample and carrying out the entire assay procedure using the aliquot containing the internal standard.

Generally, homogeneous and heterogeneous immunoassays depend upon the ability of a first binding member of a binding member pair to specifically bind to a second binding member of a binding member pair wherein a conjugate, comprising one of such binding members labeled with a detectable moiety, is employed to determine the extent of such binding. For example, where such binding pair members are an analyte and an antibody to such analyte, the extent of binding is determined by the amount of the detectable moiety present in the conjugate, which either has or has not participated in a binding reaction with the analyte, wherein the amount of the detectable moiety detected and measured can be correlated to the amount of analyte present in the test sample.

Homogeneous immunoassays typically are performed in a competitive immunoassay format involving a competition between an analyte from a test sample and a tracer for a limited number of receptor binding sites on an antibody to the analyte. The tracer comprises the analyte or analog thereof labeled with a detectable moiety wherein the concentration of analyte in the test sample determines the amount of the tracer that will specifically bind to the antibody. The amount of the tracer-antibody conjugate produced by such binding may be quantitatively measured and is inversely proportional to the amount of analyte present in the test sample. For example, fluorescent polarization techniques for making such determination, such as in fluorescent polarization immunoassays as described herein, are based on the principle that a fluorescently labeled compound when excited by linearly polarized light will emit fluorescence having a degree of polarization inversely related to its rate of rotation. When a molecule such as a tracer-antibody conjugate having a fluorescent label is excited with a linearly polarized fluorescent molecule it is constrained from rotating between the time light is absorbed and emitted. When a "free" tracer molecule (i.e., unbound to an antibody) is excited by linearly polarized light, its rotation is much faster than the corresponding tracer-antibody conjugate and the molecules are more randomly orientated, therefore, the emitted light is polarized. Accordingly, when plane polarized light is passed through a solution containing the aforementioned reagents, a fluorescent polarization response is detected and correlated to the amount of analyte present in the test sample.

Various fluorescent compounds which can be employed for performing fluorescent polarization assays on the automated analytical system of the present invention include, but are not intended to be limited to, aminofluoresceins, such as described in U.S. Pat. No. 4,510,251 and U.S. Pat. No. 4,614,823, incorporated herein by reference; triazinylaminofluoresceins, such as described in U.S. Pat. No. 4,420,568 and U.S. Pat. No. 4,593,089, incorporated herein by reference; carboxyfluoresceins, such as described in U.S. Pat. No. 4,668,640, incorporated herein by reference; and the like.

Heterogeneous immunoassays typically involve a labeled reagent or tracer comprising an analyte, an analog of the analyte, or an antibody thereto, labeled with a detectable form, a free species and a bound species. In order to correlate the amount of tracer in one of such species to the amount of analyte present in the test sample, the free species must first be separated from the bound species, which can be accomplished according to methods known in the art employing solid phase materials for the direct immobilization of one of the binding participants in the binding reaction, such as the antibody, analyte or analog of the analyte, wherein one of the binding participants is immobilized on a solid phase material, such as a test tube, beads, particles, microparticles or the matrix of a fibrous material, and the like, according to methods known in the art.

Heterogeneous immunoassays can be performed in a competitive immunoassay format as described above wherein, for example, the antibody can be immobilized to a solid phase material whereby upon separations the amount of the tracer which is bound to such solid phase material can be detected and correlated to the amount of analyte present in the test sample. Another form of a heterogeneous immunoassay employing a solid phase material is referred to as a sandwich immunoassay, which involves contacting a test sample containing, for example, an antigen with a protein such as an antibody or another substance capable of binding the antigen, and which is immobilized on a solid phase material. The solid phase material typically is treated with a second antigen or antibody which has been labeled with a detectable moiety. The second antigen or antibody then becomes bound to the corresponding antigen or antibody on the solid phase material and, following one or more washing steps to remove any unbound material, an indicator material such as a chromogenic substance which reacts with the detectable moiety (e.g., where the detectable moiety is an enzyme, a substrate for such enzyme is added) to produce a color change. The color change is then detected and correlated to the amount of antigen or antibody present in the test sample.

For example, a heterogeneous immunoassay which can be performed by the automated analytical system of the present invention, in either a competitive or sandwich immunoassay format, is a microparticle capture enzyme immunoassay, such as that described in *Clinical Chemistry*, Volume 34, No. 9, pages 1726–1732 (1988), employing microparticles as the solid phase material.

In addition, the use of sucrose in microparticle diluent has been found to achieve neutral density of the microparticles. The methodology entails the determination of the optimum sucrose concentration which will eliminate the settling of microparticles. The sucrose concentration required to achieve neutral density is assay specific and microparticle lot specific. The principal involves dissolving sucrose in solution to increase the density of the diluent. When the density of the diluent and microparticles are equivalent, the microparticles will be in a suspended state. Density neutralization can also be achieved by using other materials such as metrizamide and/or metrizoic acid.

Separation of the bound and free species is accomplished by capture of the microparticles on a glass fiber matrix of an MEIA cartridge, a process that relies on the high affinity of glass fibers for the microparticles, wherein the microparticles adhere to the surface of the fibers irreversibly, and nonspecifically bound material can be effectively removed by washing the matrix. The matrix also provides a precisely located mechanical support for the microparticles during the optical quantification phase of the assay protocol as described herein.

When performing a sandwich immunoassay, microparticles coated with antibody to the analyte in the test sample are incubated with the test sample containing the analyte of interest to form a capture complex with the analyte from the test sample. A conjugate comprising antibody to the analyte labeled with a detectable moiety, preferably an enzyme, is then incubated with the capture complex to form the second of a sandwich complex. When performing a competitive immunoassay, microparticles coated with antibody to the analyte in the test sample are incubated with the test sample containing the analyte of interest and a conjugate comprising the analyte or analog thereof labeled with a detectable moiety, preferably an enzyme. Removal of unbound conjugate is accomplished with the glass fiber matrix of the MEIA cartridge and, where the detectable moiety is an enzyme, a substrate for the enzyme capable of providing a detectable signal is added and the signal provided thereby is measured and correlated to the amount of analyte present in the test sample. Preferably, the enzyme-substrate system employed by the competitive and sandwich MEIA formats is alkaline phosphatase and 4-methylumbelliferyl phosphate (MUP), although other enzyme-substrate systems known in the art can be employed as well.

The MEIA cartridge which is employed by the automated analytical system of the present invention comprises a reaction well for retaining and immobilizing microparticle-analyte complexes. The reaction well has an entrance port and means for holding a quantity of sample and assay reaction mixtures positioned over a fibrous matrix which retains and immobilizes microparticle-analyte complexes as described above. The fibrous matrix is composed of fibers having an average spatial separation greater than the average diameter of the microparticles. Preferably, the average fiber spatial separation is greater than 10 microns.

The reaction well further comprises an absorbant material positioned below the fibrous matrix to enhance the flow of sample and assay reaction mixtures through the fibrous matrix. Preferably, the absorbant material is a fibrous material whose fibers predominately lie in a plane perpendicular to the lower surface of the fibrous matrix. The absorbant material is in fluid communication with the fibrous matrix. Generally, the absorbant material is in physical contact with the lower surface of the fibrous matrix. The interior of the reaction well, therefore, is generally sized or contains positioning means to maintain the fluid communication between the absorbant material and the fibrous matrix. Preferably, a spike located at the bottom of the reaction well can be used to force the absorbant material into contact with the lower surface of the fibrous matrix. Additionally, it is preferable to vent to the atmosphere the gases displaced in the absorbant material by the liquids absorbed therein during the performance of an immunoassay.

According to the immunoassay methodologies described above, standard solutions of the analyte of known concentrations covering the clinical concentration range are typically prepared and assayed as is the test sample to be assayed. This blank assay provides a series of signal measurements corresponding to the known concentrations from which a standard curve is drawn. The optical signal corresponding to the unknown sample is correlated in a concentration value through interpretation from the blank or standard curve.

Automated analytical methodology for effecting analysis of a plurality of test samples according to the present invention is achieved by introducing reagent packs, test sample container and reaction vessels onto concentric carousels of a main carousel. The test sample container can be a test tube, cuvette, vacutainer tube, and the like, for holding a test sample. The reagent packs and test sample containers are identified and aligned respectively with a reaction vessel for transfer and kitting of the reaction vessel by transfer of test sample and specific reagents from the reagent pack for preparation of a predetermined test. The reaction vessel containing the test sample and one or more reagents is transferred to a process carousel wherein controlled environment conditions exist for incubation once the sample has been appropriately mixed with various reagents to form a reaction mixture. When all assay processing steps have been completed, the reaction mixture is identified and transferred to at least, for example, one of a fluorescent polarization immunoassay reader or a microparticle enzyme immunoassay cartridge positioned on a separate cartridge wheel or carousel for further preparation before reading. The processed test samples are read and the readings are calculated with the resulting data being recorded and/or printed.

The methodology of the automated immunoassay analytical system is achieved through the use of a self-contained, fully automated, continuous and random access instrument comprising a main carousel assembly consisting of the reagent pack carousel, a reaction vessel carousel and a test sample container carousel concentrically and independently rotatable. The main carousel assembly is provided with a transfer pipette operated by a boom arm for transferring and kitting test sample and reagents into the reaction vessel automatically following a predetermined test schedule. The main carousel assembly is provided with bar code readers for reagent packs and test sample containers and has the capability of aligning the reagent pack carousel and test sample container carousel and a reaction vessel for pipette transfer operations. Once the assay to be performed is scheduled, the reaction vessel carousel, the reagent pack carousel and the test sample container carousel are rotated until the reaction vessel, a reagent pack and a test sample container, respectively, are determined to be in the transfer pipette access position. The transfer pipette then transfers the test sample from the test sample container and, depending upon the assay to be performed, the reagents from the reagent pack are transferred to the reaction vessel. The reaction vessel carousel is then rotated to a transfer station position which contacts the reaction vessel with a transfer mechanism and pulls the reaction vessel into the transfer station. The reaction vessel is then loaded onto the process carousel by the transfer mechanism.

When performing a fluorescent polarization immunoassay (FPIA) with the automated analytical system of the present invention, various piperting activities are performed by a second transfer pipette apparatus which is in service for the process carousel, and the process carousel is rotated so that the reaction vessel, when properly pipetted with, for example, FPIA reagents, is at the read station of the FPIA processing stations and the FPIA determination on reading, is made on the reaction vessel. The process carousel is then rotated so that the read reaction vessel is at the transfer station. The reaction vessel is again contacted and transferred by the transfer station. The transfer station is rotated and pushes the reaction vessel into a release container opening.

For a microparticle enzyme immunoassay (MEIA) performed with the automated analytical system of the present invention, after the various pipetting activities for the MEIA, which can be completed at the main carousel assembly, the reaction vessel is transferred to the process carousel as described in the FPIA process. Piperting can also be accomplished in the process carousel or jointly between the two carousels. To complete the MEIA, the reaction mixture is transferred from the reaction vessel to a matrix of an MEIA cartridge on a cartridge carousel with the second transfer pipette. The matrix is washed with a buffer and a substrate, such as MUP (defined earlier), or other suitable substrate known in the art. The cartridge carousel is then rotated so that the MEIA cartridge is positioned at an MEIA processing assembly and the MEIA determination is made. The MEIA reaction vessel is ejected into the waste container as described for the FPIA reaction vessel. The MEIA cartridge is independently ejected from the cartridge wheel by an ejector at an appropriate ejector station into a waste container.

Preferably, two distinct analytical technologies as described above, FPIA and MEIA, are incorporated into the automated analytical system of the present invention; however, more than two distinct analytical technologies can be incorporated into the inventive system. These methods are complimentary and share a commonality of apparatus and procedural steps, with the FPIA generally being the method of choice for analytes of low molecular weight and MEIA for molecules such as protein hormones, antibodies or analytes of low molecular weight requiring higher sensitivity. The two technologies share system components including the operator control panel, pipetting boom assemblies, fluidic systems, air and liquid reagent heaters, printers, bar code reader and stepper motors. Such commonality of use of system components allows for a compact instrument despite the dual FPIA and MEIA capability.

The FPIA optic systems (such as described in U.S. Pat. No. 4,269,511 and incorporated herein by reference) can utilize a polarizing filter which is an electrically switched liquid crystal, maintaining a compact size and avoiding complex and potentially unreliable moving parts. When performing FPIA assays utilizing the automated analytical system of the present invention, the FPIA reagent packs will typically include a tracer comprising the analyte or analog thereof, coupled to a detectable moiety, an antibody specific to that analyte, and a specimen pretreatment reagent. In a preferred FPIA format, the analyte being determined competes with the tracer for a limited number of binding sites on the antibodies specific to the portion or portions of the analyte and tracer. The detectable moiety component of the tracer is preferably a fluorescent moiety selected from the group consisting of fluoresceins, aminofluoresceins, carboxyfluoresceins, fluoresceinamines, and the like, more preferably carboxymethyl-aminomethyl-fluorescein, carboxyethyl-aminomethyl-carboxyfluorescein, 6-carboxyfluorescein, 5-carboxyfluorescein, succinylanimomethyl-fluorescein, thiourea-aminofluorescein, methoxytrianolyl-aminofluorescein, aminofluorescein, and the like.

In another embodiment, the FPIA format utilizes a unique, round, plastic, reaction cuvette suitable for fluorescence polarization and absorbance assay technologies which require no orientation other than top-to-bottom. This plastic reaction cuvette has physical characteristics of low birefringence throughout the optical read region as well as stringent dimensional tolerances which allow reproducible absorbance readings. Birefringence is defined as the degree of retardation of the extra-ordinary ray as it passes through a material. The greater the degree of retardation, the greater will be the level of birefringence. Retardation of the extra-ordinary ray is dependent on the magnitude and direction of the induced stress. Therefore, passing a ray of linearly polarized light through a material with induced stress will result in depolarization of the ray. In order for a cuvette to be utilized for fluorescence polarization measurements, it is important that the cuvette be prepared under conditions which yield minimum stress. The geometry of the cuvette has been designed to utilize the inherent fluidics of automated medical diagnostic instrumentation to minimize the hydrophobic effect of plastic.

MEIA results can be determined by quantifying the rate of fluorescence developed when fluorogenic substrate is converted by the action of an enzyme-labeled conjugate. For example, when performing either a competitive MEIA or sandwich MEIA, the specifically bound alkaline phosphatase on the microparticles is detected by addition of the fluorogenic substrate MUP to the matrix. The alkaline phosphatase catalyzes hydrolysis of the MUP to inorganic phosphate and fluorescent 4-methylumbelliferone (4-MU). The liberated 4-MU is detected by the MEIA optics assembly front surface fluorometer which is designed to detect fluorescence of low concentrations of 4-MU without interference by fluorescence of 4-MUP at 367 nm. A system of lenses and optical filters focus filtered light (365 nm wavelength) from a mercury arc lamp on to the surface of the matrix and focus emitted fluorescence from 4-MU (448 nm wavelength) on to a photo multiplier tube. Like the FPIA optics assembly, the MEIA optics system is compact and has no moving parts. About five percent of the excitation light is detected by a photodiode, allowing normalization of the fluorescence data and generation of a control signal used by the lamp power supply to maintain the intensity of the excitation light within five percent over the useful life of the lamp. The MEIA post-processor uses linear regression analysis to convert the data from multiple successive determinations of 4-MU fluorescence to a rate which is proportional to the concentration of alkaline phosphatase conjugate specifically bound to the microparticles.

MEIAs can be run with a multi-position MEIA auxiliary carousel and process carousel as well as a MEIA reagent pack containing microparticle reagent, an alkaline phosphatase conjugate and, in some cases, a dilute buffer specific for the assay being performed. Because the microparticles tend not to settle out of suspension during the course of the assay, they can readily be pipetted. The effective surface area of polystyrene latex microparticles is severalfold greater than that of a large diameter polystyrene bead (e.g., one quarter inch beads) commonly used in commercial immunoassays. Because of this large surface area and the very small diffusion distance between analyte and the capture molecules on the surface of the microparticles, the capture phase employed in many of the MEIA methods being performed reaches equilibrium within several minutes, allowing for a full carousel of test samples to be completed in a very short time frame.

Unlike an FPIA, the heterogeneous immunoassays, such as a MEIA, require a separation step as described above. In particular, after incubation of the microparticles with a test sample, the microparticles are separated from the reaction mixture by transfer to the matrix contained in the MEIA cartridge as described above. The matrix provides a precisely located mechanical support for the microparticles during the subsequent optical read phase of the assay. This precisely located mechanical support, i.e. the cartridge, is fit into the auxiliary carousel at a predetermined spacing from the reader apparatus by camming means.

BRIEF DESCRIPTION OF THE DRAWINGS

This inventive automated analytical system, discussed in terms of an immunoassay system, may be more fully understood by reference to the accompanying drawings wherein:

FIGS. 4A and 4B represent a perspective side elevational view and partial end view of a reagent pack and reagent pack cover means;

FIG. 5 is a top view in isolation and partial section of drive and guide elements of the front end carousel being removed;

FIG. 6 is a cross-sectional side view of a process carousel in isolation with two reaction vessels in place, one of which is in position for FPIA read;

FIG. 7 is an isometric view of the probe, probe arm and pipettor in isolation;

FIG. 9 is a cross-sectional side elevational view of an automatic bubble flushing syringe apparatus;

FIG. 9A is a sectional side view in isolation of the syringe bore end portion with the reciprocating piston near the end of travel toward the bore end portion;

FIG. 9B is a sectional end view in isolation of the piston and bore taken along line 9B–9D;

FIG. 12 is a perspective side elevational view of the transfer station;

FIG. 17 is a side elevational view in section of a MEIA cartridge feeder;

FIG. 26 is a schematic reaction sequence of a FPIA, T4 assay;

FIG. 27 is a schematic reaction sequence of a MEIA, one-step sandwich; and

FIG. 28 is a schematic reaction sequence of a MEIA, two-step sandwich.

DETAILED DESCRIPTION OF THE DRAWINGS

Preferred embodiments of the automated immunoassay analytical system according to the invention are presented only with those components of primary interest with respect to the inventive apparatus and processes. The drawings do not illustrate all the mechanical and electrical elements for driving and controlling the various components of the apparatus. These omitted elements may have various known forms which can be readily realized by one of normal skill in the art having knowledge of the information provided herein with regard to the mode of operation of the system and the various components and related processes utilized for treating samples and determining analytical results.

Figure 1:
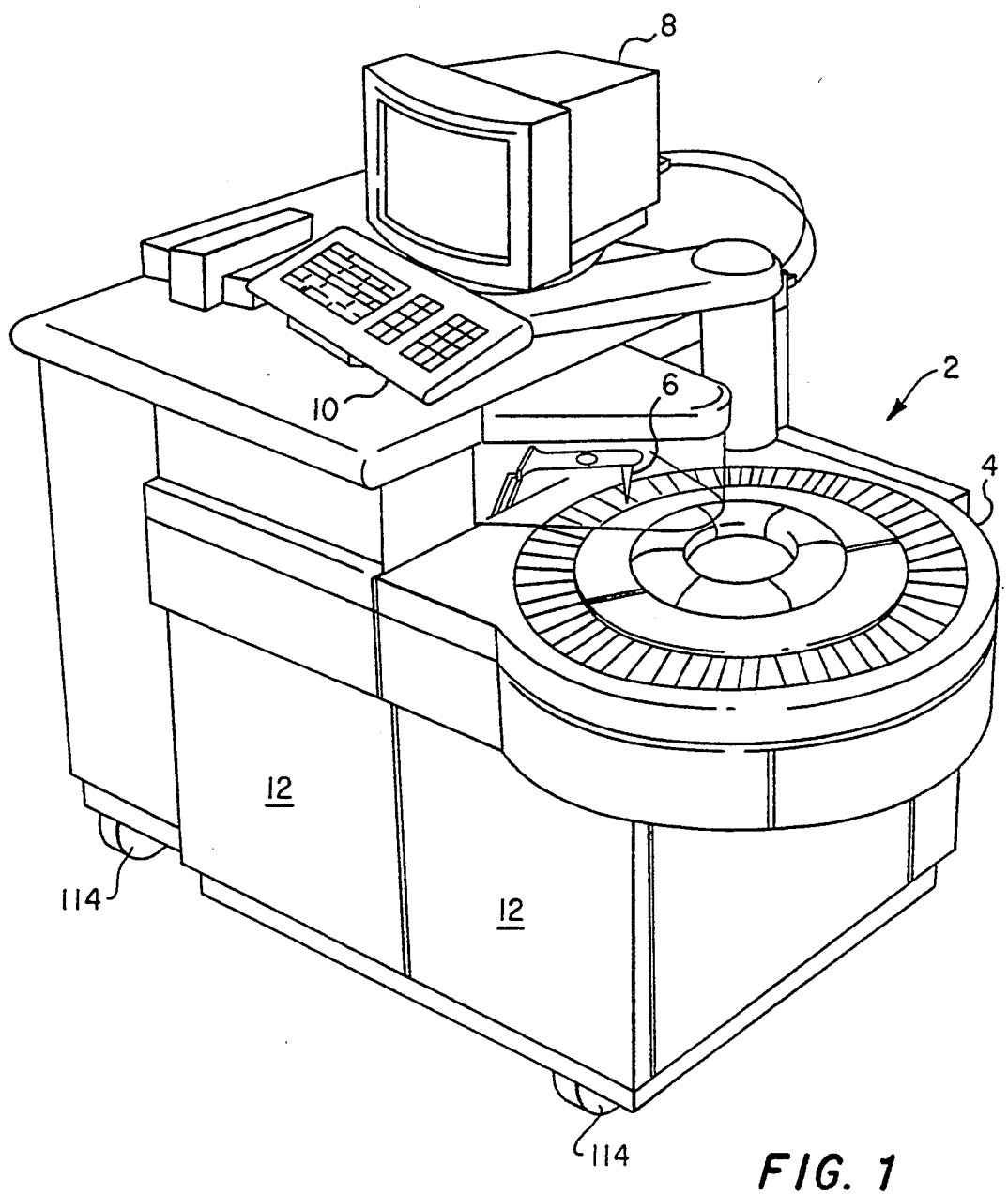
FIG. 1 is an isometric view of the automated immunoassay analytical system according to the invention illustrating the system cabinetry, exposed front end carousel, computer screen and keyboard.
Figure 2:
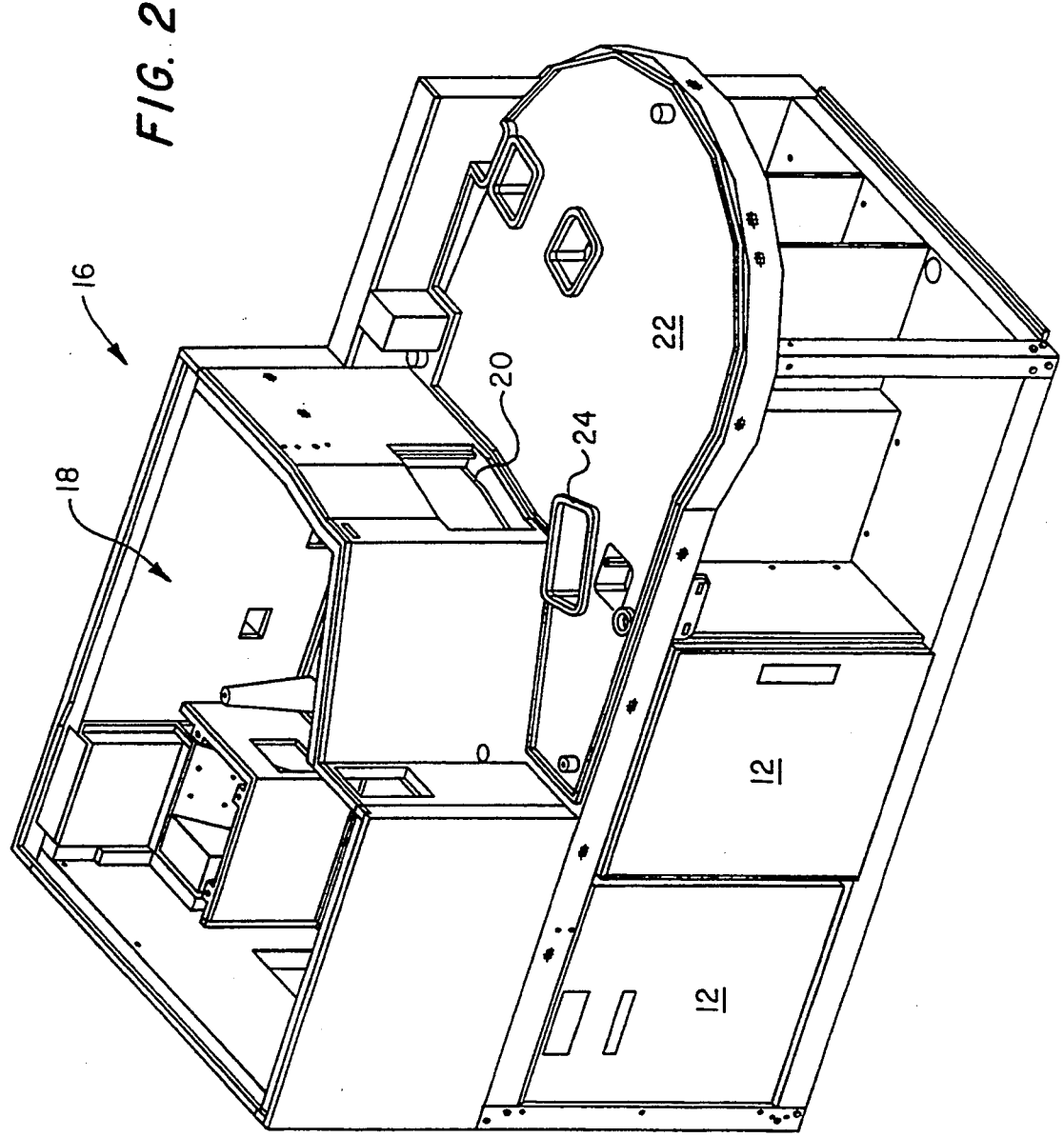
FIG. 2 is an isometric view of the automated immunoassay analytical system apparatus frame and cabinet.

Referring to the drawings, FIGS. 1 and 2 present isometric views of the automatic immunoassay analytical system apparatus. The system as it appears in FIG. 1 presents the apparatus as used by the technician, with FIG. 2 illustrating an isometric view of the frame and cabinetry with component parts removed. The system apparatus of the present invention is identified generally by the reference numeral 2 in FIG. 1. The system apparatus 2 has an exposed front end carousel 4 which is serviced by a first transfer pipette mechanism 6 for kitting scheduled tests along with samples into a reaction vessel. The system provides a computer screen 8 and computer keyboard 10 along with access panels 12 for accessing storage and waste compartments. The system apparatus 2 is provided with rollers 14 for movement of the apparatus within a laboratory complex as required. The freedom of movement of the apparatus through rollers 14 is allowed since the system is fully self-contained but for power requirements.

In FIG. 2 the system apparatus 2 cabinet frame 16 is illustrated with substantially all functioning components of the system removed. A controlled environment zone 18 is a closed unit during operation with light shielding and rigid control of airflow as well as temperature as opposed to the open front end carousel 4. The front end carousel 4 communicates with the controlled environment zone 18 through a transfer port 20. The front end carousel 4 is mounted to an aluminum base plate which rests on a support platform 22 and the first transfer pipette mechanism is mounted on means 24.

Figure 3:
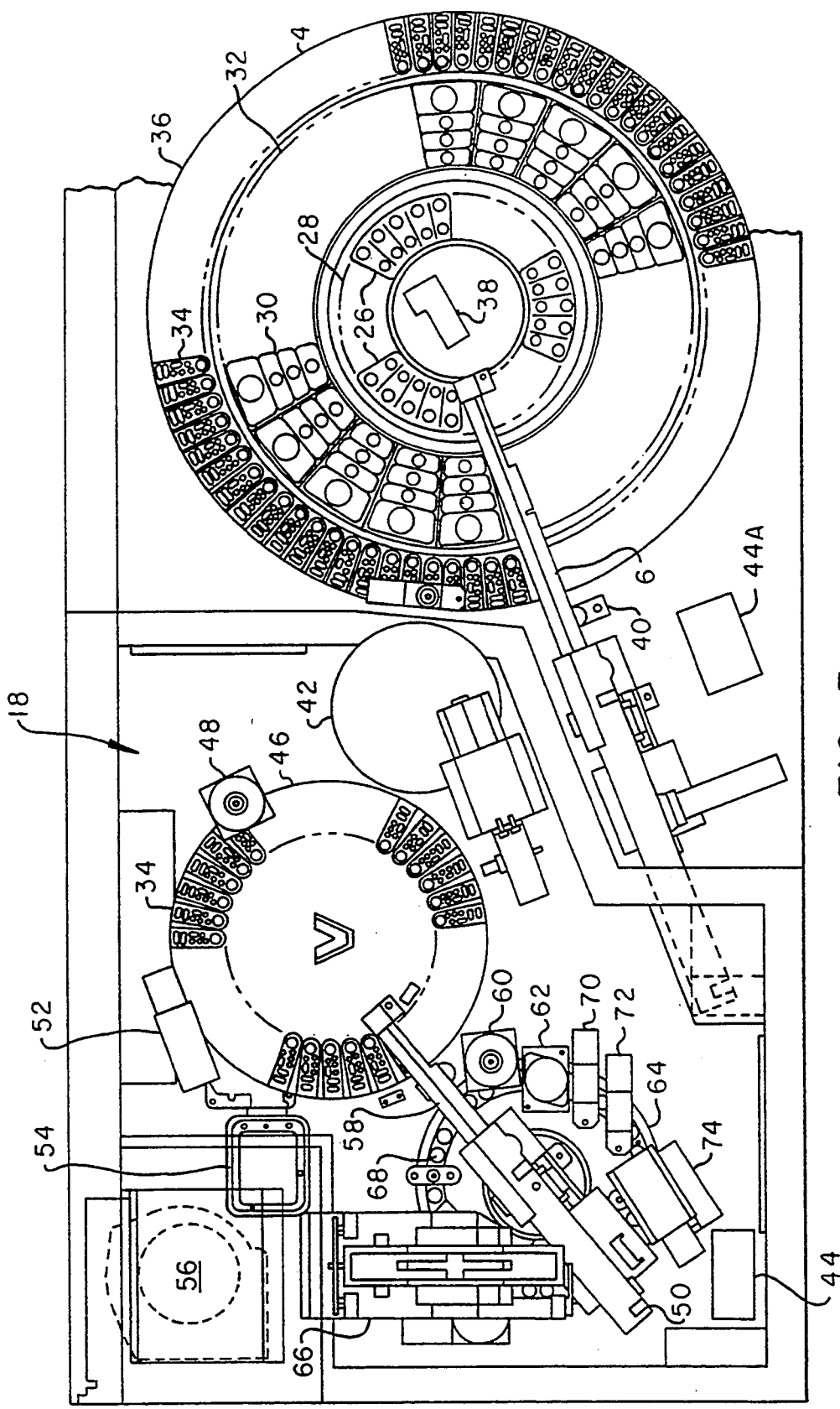
FIG. 3 is a top plan view in section with component covers removed to show the system apparatus in detail and relative position.

The top plan view in section of FIG. 3 presents the functioning component apparatus in some detail with relative positioning of the apparatus to further illustrate the process flow of the system. For example, sample cups 26 are mounted on a sample cup carousel 28 which is concentrically fitted within the front end carousel 4 along with reagent pack carousel 32 and reaction vessel carousel 36. The reagent pack carousel 32 is concentrically fitted between the sample cup carousel 28 and the reaction vessel carousel 36. The reagent pack carousel carries reagent packs 30 and the reaction vessel carousel 36 carries reaction vessels 34. The front end carousel 4 has an operable bar code reader 38 for automatically identifying reagent pack carousel 32 and sample carousel 28. A wash cup 40 is provided for the first transfer pipette mechanism 6 for washing as required between transfer of various sample and reagents. The first transfer pipette mechanism 6 is utilized in kitting the various reagent pack liquid materials and sample into a reaction vessel 34. The reagents and the sample are properly kitted through means of the first transfer pipette mechanism 6 inclusive of pump means. The various carousels are rotated and aligned for kitting at the pipetting station. The kitted reaction vessel 34 is positioned by reaction vessel carousel 36 into the proper position for transfer to the transfer station 42. The reaction vessel 34 is transferred to the transfer station 42 through transfer means wherein the transfer station 42 is then rotated to move the reaction vessel onto process carousel 46. As shown, the process carousel is driven by a stepper motor 48 and is serviced by a second transfer pipette mechanism 50. Both the FPIA and MEIA procedures utilize the system's apparatus commonly up through and including the process carousel 46. The process carousel 46 includes FPIA processing 52 and FPIA processing lamp 54 for direct reading of FPIA analysis of kitted, pipetted and properly reacted reagents sample from the reaction vessel 34. The controlled environmental zone 18, which includes the transfer station 42 and process carousel 46, provides FPIA processing with air circulation under temperature control by cabinet air circulation fan 56. A wash cup 58 for the second transfer pipette mechanism 50 is provided. The second transfer pipette 50 is utilized for adding reagents (pipetting) under conditions of incubation and timing to the sample in the FPIA test schedule reaction vessel 34 for FPIA processing. MEIA processing can also utilize the second transfer pipette 50 for adding reagents to the sample before the reaction mix is added to MEIA cartridges 68 which are mounted on the cartridge wheel carousel 64. The transfer of the MEIA reagent mixed sample to the MEIA cartridge 68 is by the function of the second transfer pipette 50. A motor 60 drives the cartridge wheel 64. The cartridge wheel 64 is provided with MEIA cartridges 68 through the operation of a cartridge hopper 66 which automatically feeds and positions the MEIA cartridges 68 onto the cartridge wheel 64. The process area includes the second transfer pipette mechanism 50 and heater/pump 44. The cartridge wheel carousel 64 is further serviced by a MEIA buffer heater and dispenser 70, 4-methylumbelliferyl phosphate (MUP) heater and dispenser probe 72, and MEIA reader 74. The MEIA cartridges 68 are removed from the cartridge wheel 64 by a cartridge ejector 62 after the MEIA read has been completed.

It is to be understood that the utilization of the first transfer pipette mechanism 6 and the second transfer pipette mechanism 50 as described herein provide a safety mechanism to ensure that test samples and reagents are pipetted to thereby prevent false negative results in the event there are incorrect amounts of the respective sample and reagents for a particular assay.

Figure 4:
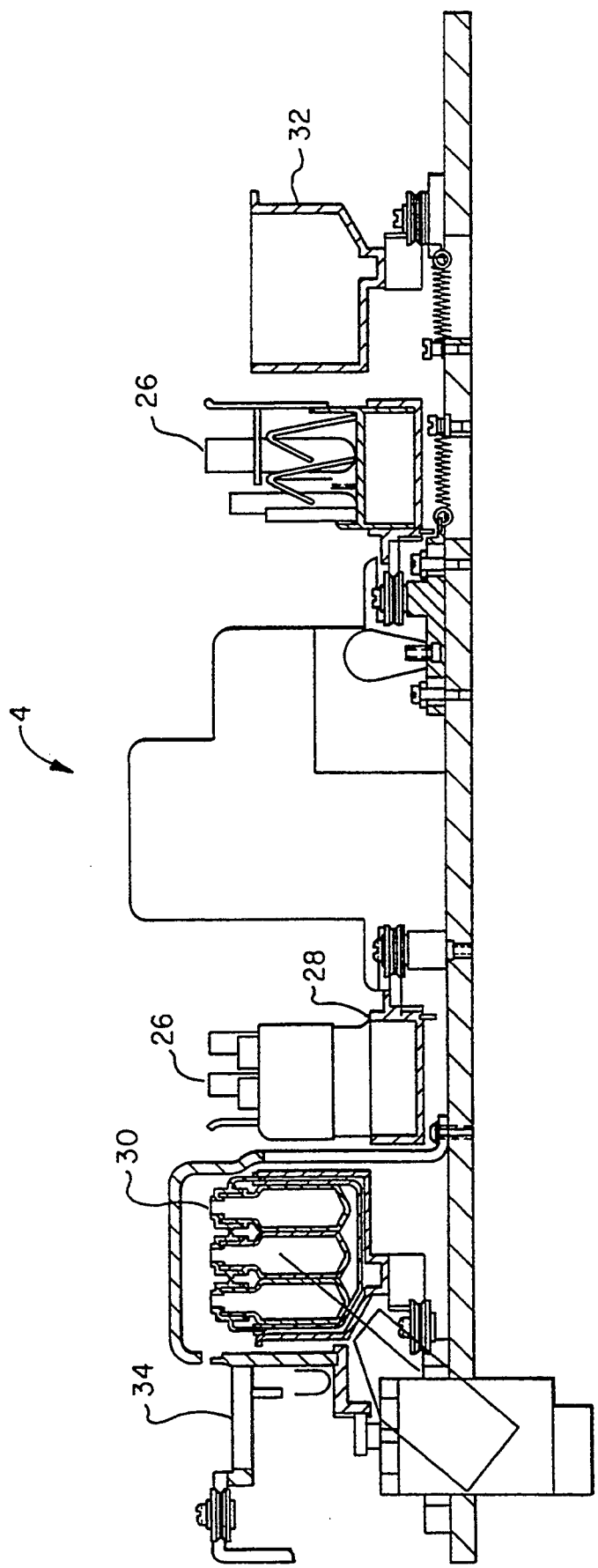
FIG. 4 is a front elevational view in isolation and partial section of elements of the front end carousel.

Approaching the operable elements of the system in greater detail, FIG. 4 provides a front elevational view in isolation and partial section of elements of the front end carousel 4. FIGS. 4A and 4B illustrate a reagent pack with a cover means 31 which is opened and closed pivoting along axis 37. A return notched drive arm 35 is utilized to open and close the cover means 31 by contact with the cover contact surface 33.

FIG. 5 provides a top view in isolation and partial section of elements of the drive and guide systems of the main carousel 4 with the various carousels removed. In FIG. 5 a sample cup carousel stepper motor 76 is shown mounted with mounting spring 78. The reagent pack carousel motor 80 is also shown with a mounting spring 82. The reaction vessel carousel motor 84 and mounting spring 86 are positioned to the exterior of the two inner carousels, i.e. the sample cups carousel 28 and the reagent pack carousel 32. Roller guides 88 are provided for the sample cup carousel 28 and a tensioning spring 90. The reagent pack carousel is provided with roller guides 92 and tensioning means 94. The reaction vessel roller guides 96 are also provided with spring elements 98, the purposes of the guide and these various spring elements being to maintain very finite tracking of the concentric carousels when motivated by the individual stepper motors.

The front end carousel 4 inclusive of the three front end carousels, the sample cup carousel 28, reagent pack carousel 32 and reaction vessel carousel 36 can by example contain the following capacities. The sample cup carousel 28 can hold 60 blood collection tubes, such as Vacutainer ® blood collection tubes, or 90 sample cups which are injection molded as one piece and can be provided with standalone base mounts. Standalone base mounts are suitable for technician handling and pipertering of samples into the sample cups. The reagent pack carousel 32 provides for 20 different reagent packs 30. The reaction vessel carousel 36 provides 90 reaction vessels 34.

The process carousel 46 as shown in FIG. 6 is an isolational cross-sectional side view. One reaction vessel 34 is at rest or nonoperative position and a second reaction vessel 34 is in position for FPIA read. The process carousel 46 is capable of bidirectional motion for timely movement of the various reaction vessels 34 to pipettor action, read, or transfer to and from the carousel. Up to about 36 or more reaction vessels 34 can be processed at one time on the process carousel 46 depending on diameter and sizing of the reaction vessels 34.

The first transfer pipette mechanism 6 of FIG. 7 includes a transfer pipette Z axis motor 102 which moves the probe arm 104, probe 106 and probe tip 108 in a vertical direction while transfer pipette R axis motor 100 drives the probe arm 104, probe adjustment means 106 and probe tip 108 in a horizontal motion. The first transfer pipette mechanism 6, sometimes labeled "Sample Probe Arm Mechanism", moves the probe between the sample cup 26, the reagent pack 30, the reaction vessel 34 and the wash cup 40. The wash cup 40 is used to wash the interior and exterior surfaces of the first transfer pipettor mechanism 6 probe. The drive of the first transfer pipette mechanism is a rack-and-pinion drive means along the Z and R axis by two stepper motor drivers. A brake is provided to hold the Z axis position when power is lost, thus avoiding damage to the apparatus. For example, the first transfer pipette mechanism can be designed to have a Z axis travel of about 3 inches and an R axis travel of 11-½ inches.

Figure 8:
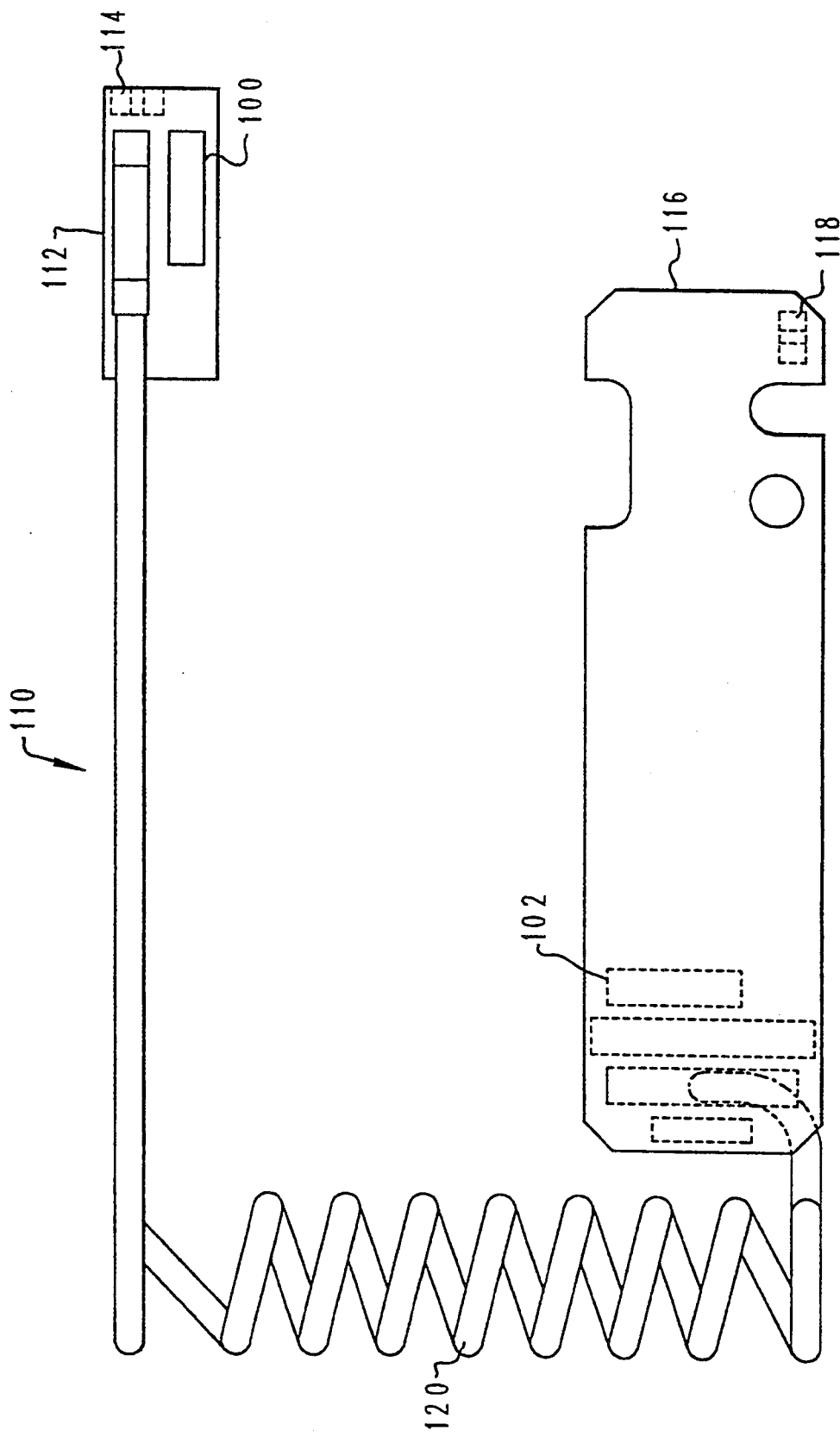
FIG. 8 is a schematic side view of the probe arm wiring and sensor means.

The first transfer pipette mechanism 6 and the second transfer pipette mechanism 50 are closely related in general apparatus function and design, with variation on travel and size being the only substantial differences. Both units have a probe arm circuit 110 as illustrated by the schematic side view of FIG. 8. The schematic illustrates the R axis motor 100 and the Z axis motor 102 in relationship to an upper PCB 112 and a R axis home sensor 114. A lower PCB 116 is illustrated in relationship to the Z axis home sensor 118 with a coil cable 120 connecting the various elements.

Various elements of syringe 122 which provides automatic bubble flushing and fluids to the various piperting mechanisms is provided in various views in FIGS. 9, 9A and 9B. The ability of diagnostic instrumentation to accurately perform an assay is critically dependent on the precision and accuracy with which syringes, i.e. pipetting, can aspirate and dispense reagents and samples. The precision and accuracy of a syringe is severely degraded by the presence of small air bubbles inside a syringe. Bubbles, unfortunately, are all too common and are difficult to remove or avoid. Syringe 122 avoids these problems by automatically flushing bubbles completely out of the fluidics system. The syringe 122 is configured such that a piston 124 reciprocates through a seal 126 and into a close-fitting bore 128. The end of the bore 130 is closed. The piston 124 has a piston end 132 which approximates the geometry of the closed bore end 130. Two ports to the bore are 180° apart and are located near the seal and are comprised of a fluid entry port 134 and a fluid exit port 136. An annulus 138 exists between the piston 124 and bore 128. Pressurized line diluent is introduced to the fluid entry port 134. The fluid flows out into the annulus 138 around both sides of the piston 124 and then into the fluid exit port 136. This crossflow flushes bubbles from the area near the seal. While the crossflow is occurring, the piston 124 is reciprocated inside the bore 128. This reciprocation causes high fluid flow velocities in the annulus 138 between the piston 124 and the bore 128. The high flow velocity dislodges any bubbles that may be adhering to the piston 124 or bore wall. The inward stroke of the piston 124 pushes these dislodged bubbles across the crossflow area where they are swept out of the syringe. The piston end 132 and the bore end 130 have similar spherical shapes. When the piston 124 strokes to its full inward extension, it comes very close to the bore end 130. Any bubble that may be stuck on the bore end 130 is disrupted and dislodged. Likewise, when the piston strokes to its full outward extension, its end is flush with the seal 126. The sequence of reciprocating the piston while crossflowing can be automatically executed any time by the system.

Once the fluid leaves the fluid exit port 136 of the syringe 122, it must travel through a tube fitting, through a length of tubing, through another tube fitting, into a probe 106 and out the probe tip 108. It is at the probe tip 108 that the aspirating and dispensing of reagents actually occurs. Any bubbles trapped between the syringe and the probe tip will also degrade performance, so there must be no place for the bubbles flushed out of the syringe to lodge. It is therefore necessary to use zero dead volume tubing fittings on the tubing between the syringe and the probe.

Figure 10:
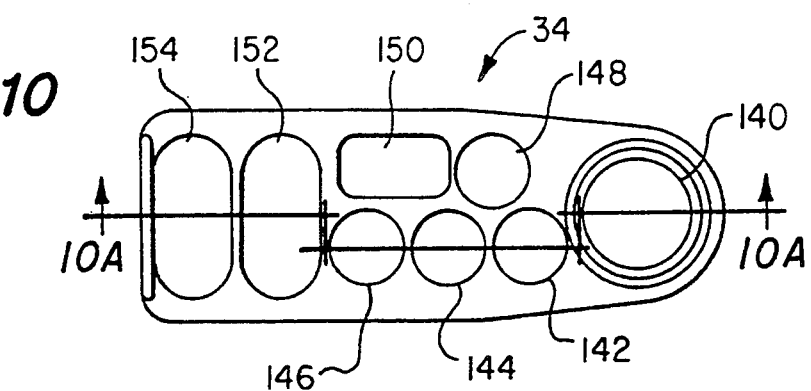
FIGS. 10 and 10A represent respectively a top plan view of a reaction vessel and a side view of the reaction vessel with reaction vessel compartments labeled where appropriate for FPIA processing.
Figure 10A:
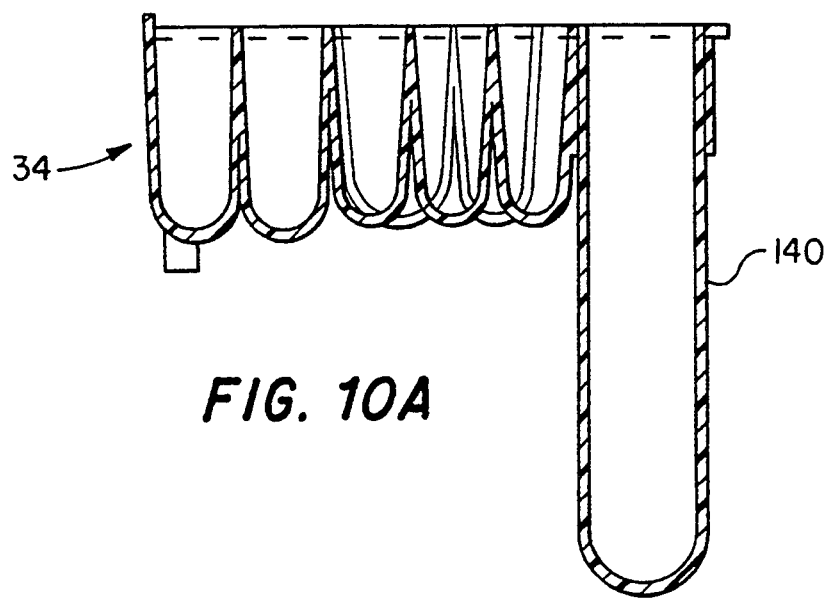

The reaction vessel 34 is discussed in detail relative to either the MEIA scheduling or the FPIA scheduling in FIGS. 10, 10A, 10B and 10C. FIGS. 10 and 10A present the FPIA kitting utilization wherein cuvette 140 is illustrated in both the top plan view, FIG. 10, and the side view, FIG. 10A. S reagent antiserum is deposited in well 142 while T reagent tracer is deposited in well 144 with P reagent popper being deposited in well 146. Wells 150 and 152 can serve for providing a variety of reagents, buffers and/or dilution liquids to the system. The sample is deposited in well 148 and predilution liquid in well 154. The utilization of the transfer pipettor in depositing the required reagents into a reaction vessel along with the sample is called kitting. The depositing of the various required reagents and the like into a single reaction vessel along with a sample to be analyzed is called pipetting.

Figure 10B:
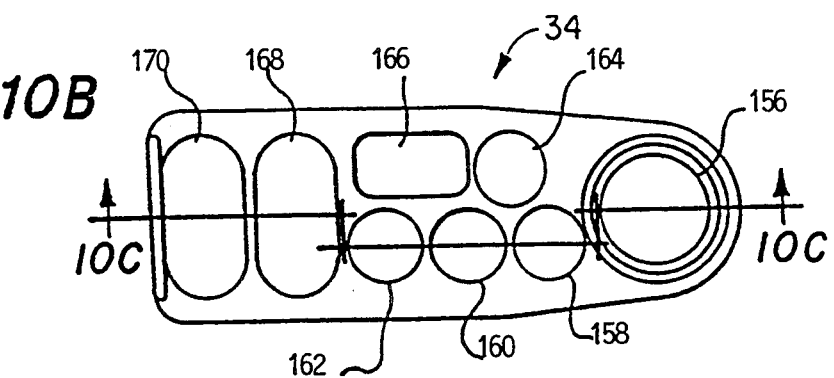
FIGS. 10B and 10C present a top plan view and a side view of the reaction vessel, respectively, labeled and presented for MEIA processing.
Figure 10C:
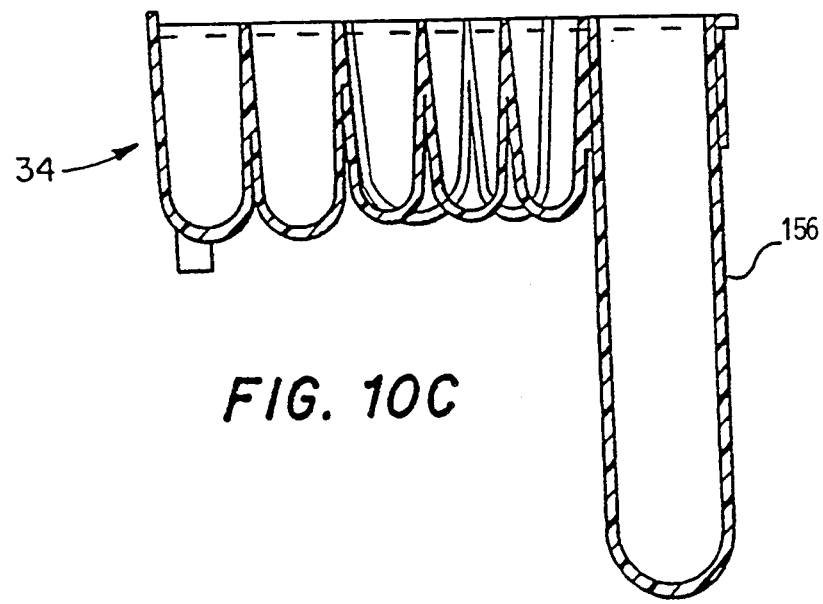

The MEIA reaction vessel as shown in top and side views of FIGS. 10B and 10C, respectively, contains prediluent in well 156; microparticle materials being deposited in well 158; conjugant directly in the reaction well 166; assay diluent in well 162; and the sample in well 164. The buffer well is 168 and predilution well is 170. Once kitting is complete, many of the subsequent FPIA and MEIA pipetting steps can be performed either in the main carousel or in the process carousel utilizing the pipetting mechanisms of both carousels. This is possible because the kitted reaction vessel, once kitted, is transferred immediately into the transfer station and thus into the process carousel which exists in a controlled temperature environment.

Figure 11:
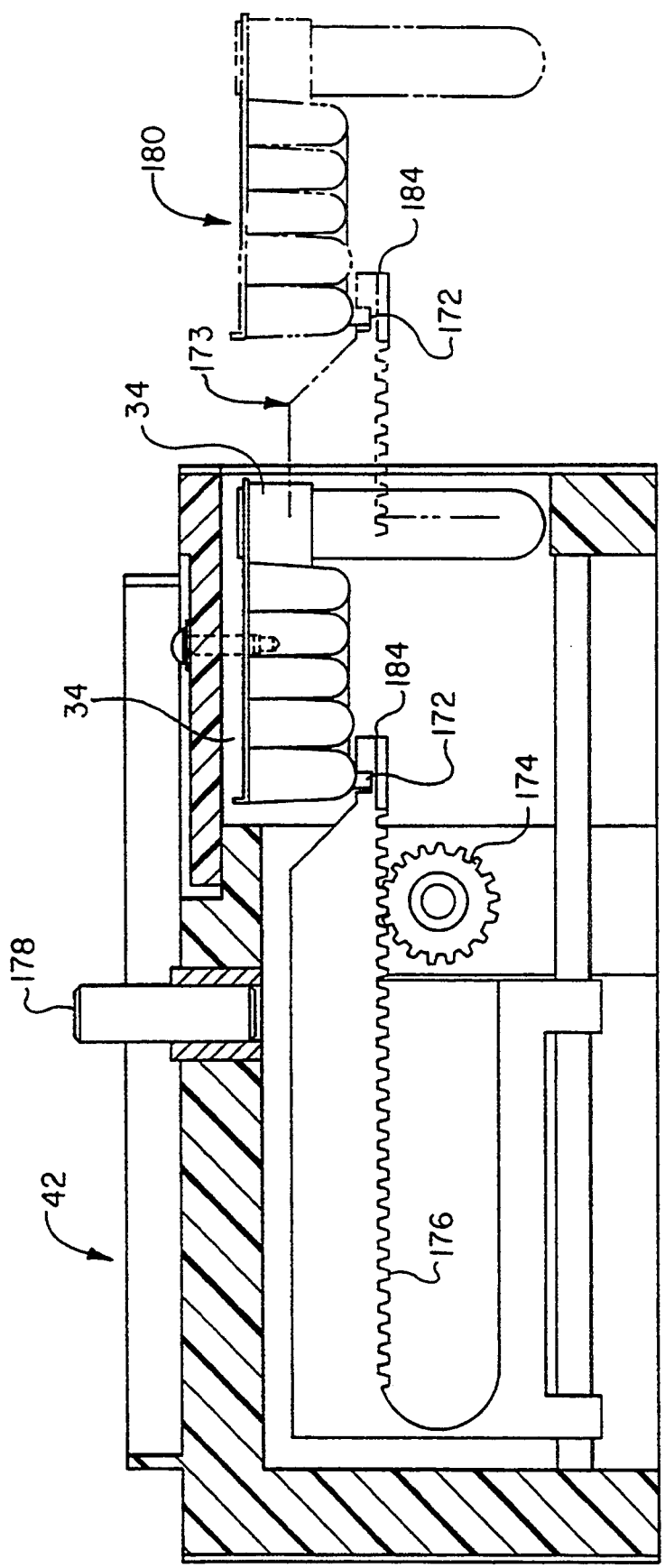
FIG. 11 is a sectional side view of the transfer element engaging a reaction vessel for transfer from the main carousel into the transfer station.

The transfer station 42 plays a key role in apparatus and process function. In FIG. 11, a sectional side view of the transfer element of the transfer station 42 is shown engaging reaction vessel 34 by means of a reaction vessel transfer projection 172. The transfer arm 173 is projected out between reaction vessel elements of the reaction vessel carousel 36 and, by rotation of the transfer station 42, engages the reaction vessel transfer projection 172. By means of a transfer arm drive gear 174, the transfer arm 173 rack gear 176 moves the transfer arm 173 out and in relationship to the transfer station 42. The transfer station 42 has a rotation axis 178. In FIG. 11, a reaction vessel is shown in phantom as would be mounted on the front end carousel 4, reaction vessel carousel 36 engaged by the transfer arm 173 by means of reaction vessel transfer projection 172. The reaction vessel 34 in FIG. 11 is illustrated onboard the transfer station by reaction vessel 34. Upon loading of the reaction vessel 34 into the transfer station 42, the transfer station is rotated about its rotational axis 178 for alignment of the transfer arm 173 for pushing the reaction vessel 34 into a receiving slot on the process carousel 46. By further rotation, the transfer arm 173 disengages from the transfer projection 172 and is withdrawn into the transfer station 42.

The transfer station 42 has a rotational axis 178 which allows for the rotational transfer from the front end carousel to the process carousel. The transfer station 42 has a transfer arm 173 which terminates in a pick 184 for positioning and hooking reaction vessel 34 by a reaction vessel transfer projection 172 as shown in FIG. 11. A motor 185 provides rotational and transverse motion of the reaction vessels into the transfer station 42 either from the front end carousel or upon return of the process carousel for disposal. The transfer station 42 has a guide 186 which in cooperation with wheel 188 provides rotational motion with precision for transfer of reaction vessels. A cover 190 is provided for avoiding contamination, i.e. dust and the like, exposure of the kitted reaction vessels when transferred from the front end carousel to the process carousel.

Figure 13:
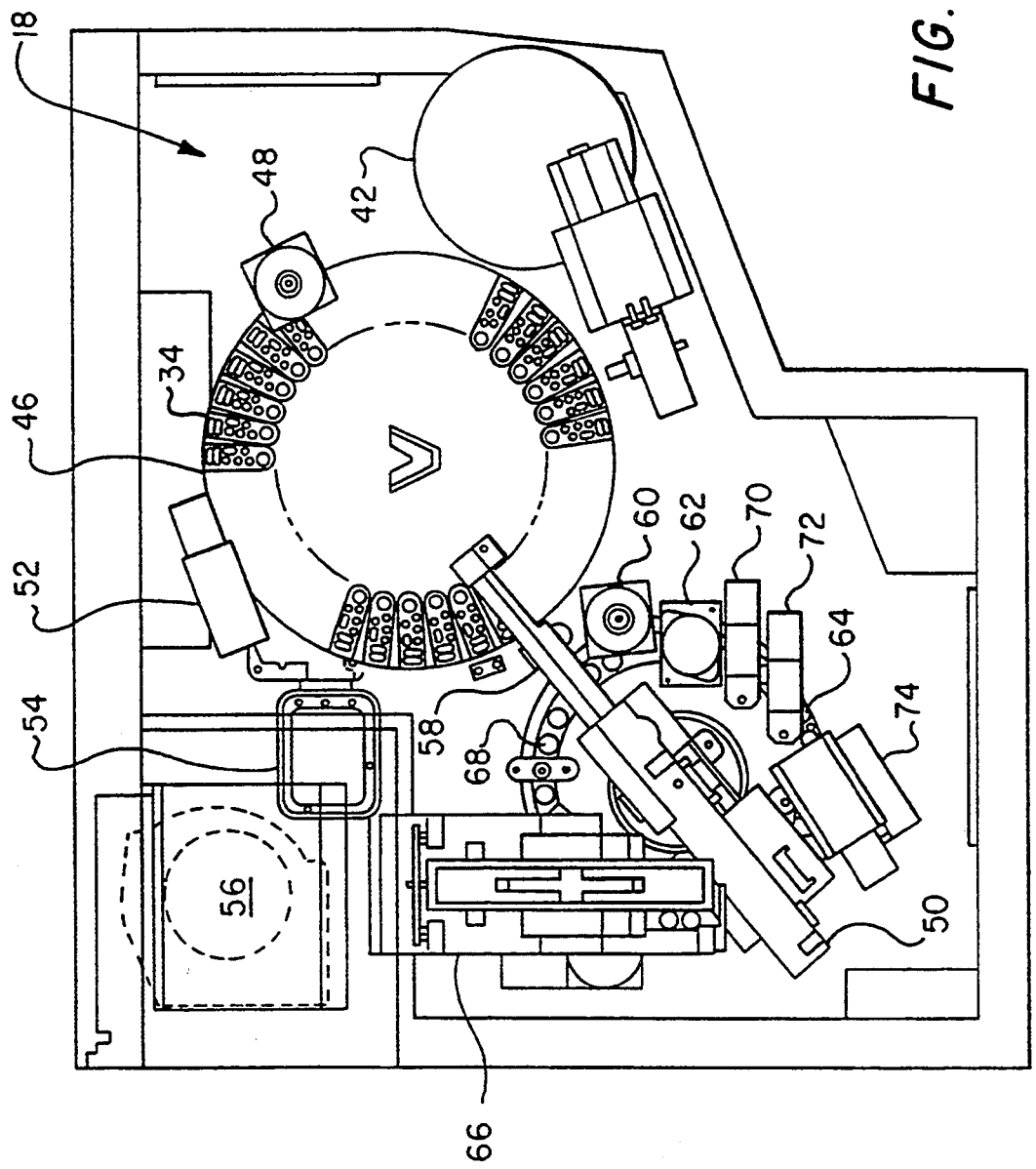
FIG. 13 is a top plan view in section illustrating in isolation the controlled environment portion of the automated immunoassay analytical system.

FIG. 13 is a top plan view in section illustrating in isolation the controlled environment portion of the system. FIG. 13 is similar to a portion of FIG. 3 illustrating the transfer station 42, the process carousel 46 and other features included in the controlled environment zone 18. The transfer station 42 moves the reaction vessel 34 between the front end carousel 4 and the process carousel 46. The transfer station 42 moves the discarded reaction vessel 34 from the process carousel 46 to the waste ejection station (not shown). The transfer station 42 is driven by a stepper motor drive and is supported by precision linear ball bearings and axis of rotation ball bearings.

The process carousel 46 holds, for example, 36 reaction vessels 34 and has a carousel diameter of about 12.5 inches. The process carousel 46 moves the reaction vessel 34 between the transfer station 42, the second transfer pipettor mechanism 50, the point of pipetting, and the FPIA reader processing 52. The process carousel 46 is driven by a stepper motor and supported by three wheels for height control and control of any radial movement caused by irregularly shaped carousel elements.

The second transfer pipette mechanism 50 moves the pipette probe between the wells in the reaction vessel 34 on the process carousel 46 to the MEIA cartridge 68 on the auxiliary carousel 64 and to the wash cup 58. A rack-and-pinion drive through two axis stepper motor drives achieves precision drive on both the R and Z axis. Travel, for example, on the Z axis can be about 3 inches and on the R axis about 4.5 to 5.0 inches.

The auxiliary carousel 64 holds, for example, 32 MEIA cartridges 68 and has a diameter of about 9.5 inches. The auxiliary carousel 64 moves the MEIA cartridges 68 between various stations including the second transfer pipettor mechanism pipette point, the MUP dispense station 72, the MEIA buffer heater and dispenses 70 and the MEIA reader 74 and the MEIA cartridge ejection point 62. The auxiliary carousel 64 is stepper motor driven and is carried by three wheels with one wheel located at the Z axis height control at the cartridge insertion point, the second wheel at the pipette point, and the third wheel at the MEIA reader in order to maintain the auxiliary carousel 64 within desired geometric relationships to these various functions.

MEIA cartridges 68 are loaded into a cartridge hopper 66 which feeds the MEIA cartridges 68 into the auxiliary carousel 64. The automatic feeding of the MEIA cartridges 68 is provided with a proper height adjustment of the cartridge 68 into the auxiliary carousel 64 as required by MEIA reading. The cartridge hopper 66 feeds individual cartridges 68 to the auxiliary carousel 64 and changes the axis of orientation of the cartridge 68 from horizontal to vertical by automatic means. Removal of the MEIA cartridges 68 is achieved through the use of an ejector 62 which operates through an ejection rod and forces the MEIA cartridge 68 from the auxiliary carousel 64 which is dropped into a solid waste container.

Figure 14:
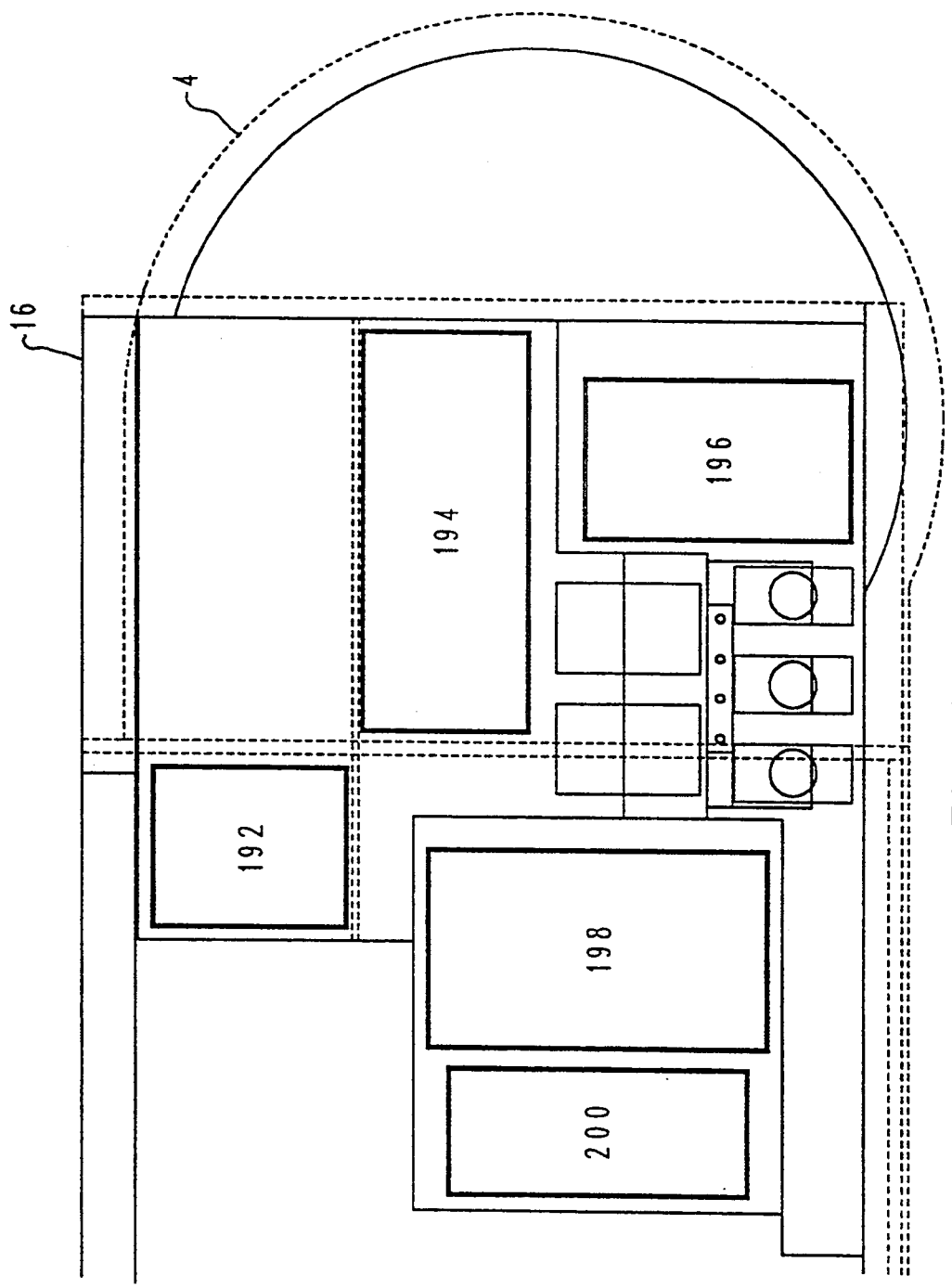
FIG. 14 is a top plan view in section of the lower cabinet of FIGS. 1 and 2 illustrating water and/or buffer supply station as well as liquid and solid waster containers.

Buffer supply stations are presented in FIG. 14 which is a top plan view in section of the system apparatus showing the cabinet frame 16, front end carousel 4 in partial phantom and a power supply element 192 along with diluent system or buffer pressurization means 194. A supply bottle 196 is also mounted in the lower cabinet of frame 16 as well as solid waste 198 and liquid waste 200 containers for receiving processed liquids and solid waste.

Figure 15:
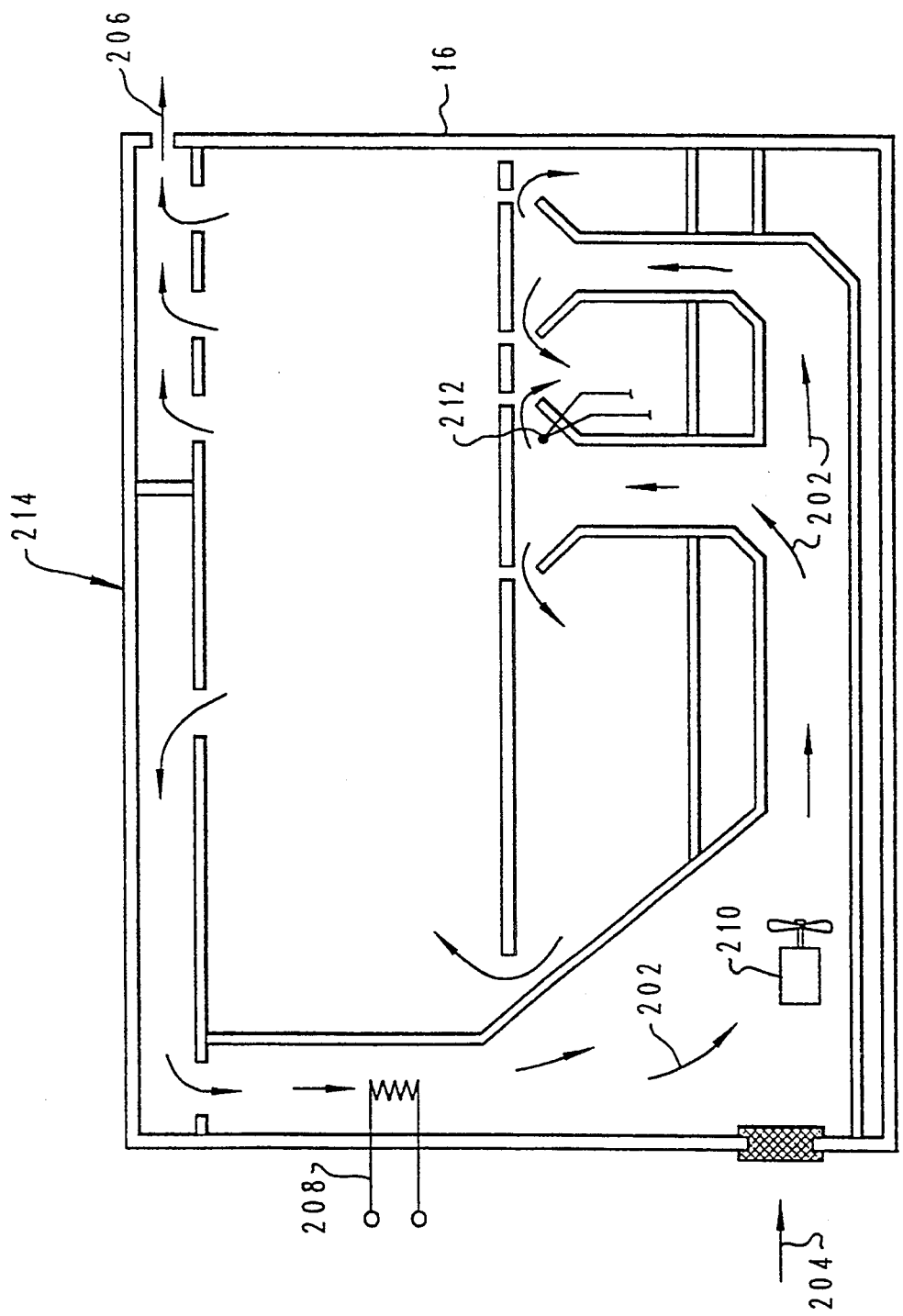
FIG. 15 is a schematic view illustrating the system control environment airflow and temperature control.

A schematic view illustrating the environmental airflow and temperature control system is shown in FIG. 15 wherein make up air 204 enters and hot air exits at exhaust 206. Airflow 202 is indicated by arrows and the controlled environmental airflow schematic 214 is provided with at least one heater element 208 and fan element 210. At least one temperature sensor 212 is provided for control of the air temperature and can be correlated with the airflow 202 control.

Figure 16:
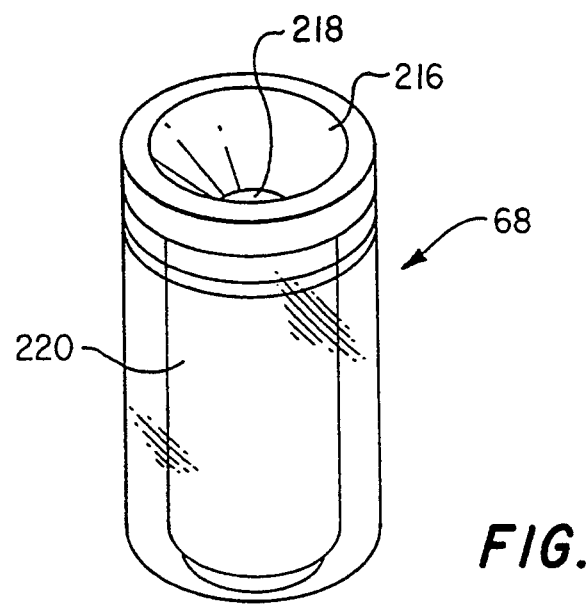
FIG. 16 is a side elevational view in partial section of a MEIA cartridge.

The MEIA cartridge 68 is shown in a side elevational view in FIG. 16. The MEIA cartridge 68 has a funnel throat 216 and a cartridge opening 218. The MEIA cartridge 68 contains support matrix material 222.

Figure 18:
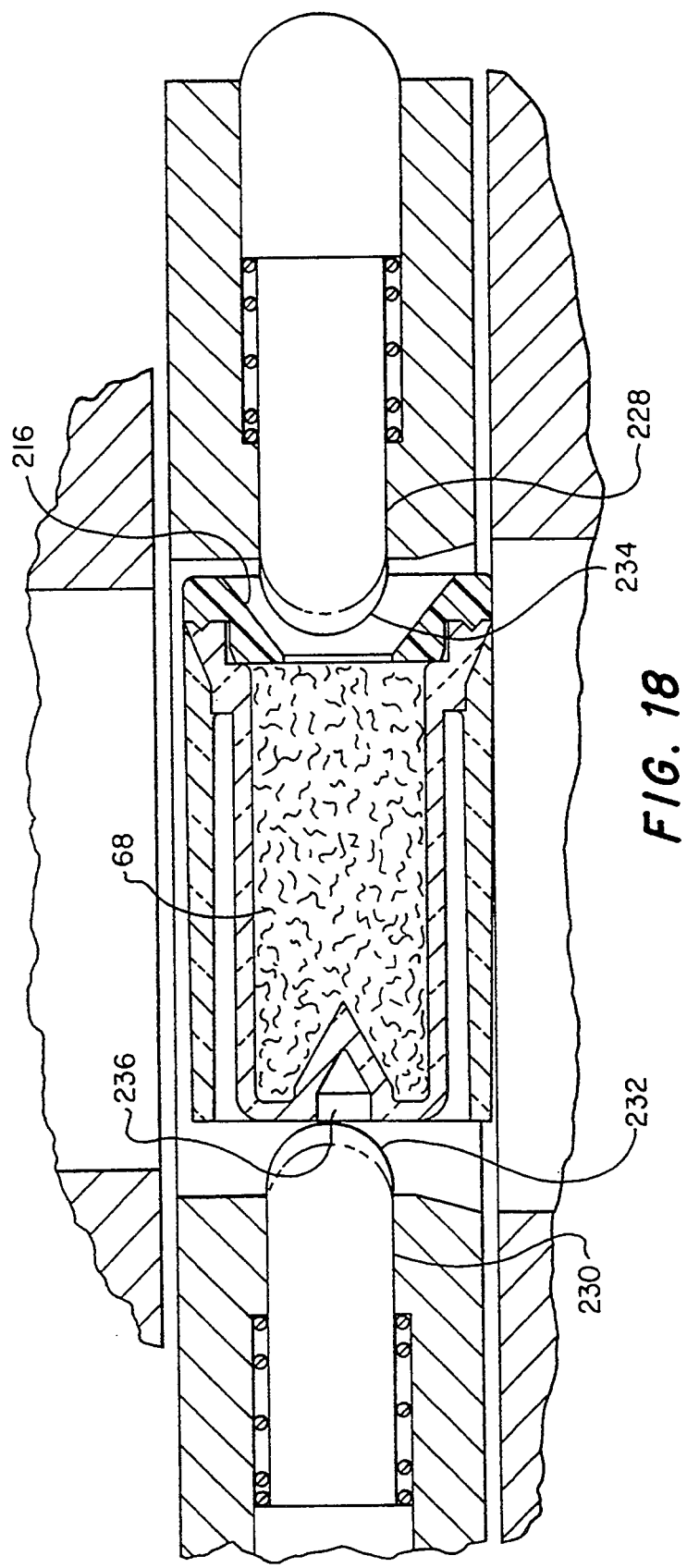
FIG. 18 is a side sectional view in isolation of the MEIA cartridge feeder, cartridge orientation pin mechanism.

A MEIA cartridge 68 and cartridge hopper 66 are shown in a side elevational view in FIG. 17. The MEIA cartridges are positioned horizontally in the cartridge hopper 66 and are manipulated from the bottom of the V-shaped cartridge hopper 66 one-by-one through a cartridge shuttle 222. The cartridge feeder has a cartridge cam block 224 and a cartridge orientation shoot 226 which functions through cartridge orientation pin 228 and cartridge orientation pin 230 for providing the MEIA cartridge 68 in vertical alignment for insertion into the auxiliary carousel 64. The orientation pins 228 and 230 are illustrated in FIG. 18 which is a side sectional view in isolation of the MEIA cartridge feeder cartridge orientation mechanism. The MEIA cartridge 68 is shown in an enlarged view in FIG. 18 as being engaged and disengaged by cartridge orientation pin 228 and cartridge orientation pin 230. The cartridge orientation pin 230 is shown in engagement position at position 232 against the base 236 of the MEIA cartridge 68 while cartridge orientation pin 228 is shown in engagement position 234 of the cartridge funnel throat portion 216. Upon withdrawal of these pins from the engaging positions, the MEIA cartridge 68 is released from the bottom portion first, i.e. the withdrawal of cartridge orientation pin 230, thus allowing the bottom of a cartridge 68 to drop by gravity before the top of the cartridge is released which is engaged by cartridge orientation pin 228 in the cartridge funnel throat 216. The rounded or semicircular holding surfaces of the orientation pin allow the release of the bottom of the MEIA cartridge and the rolloff of the funnel throat portion 216 from the cartridge orientation pin 228. The vertically aligned MEIA cartridge 68 is then inserted into the auxiliary carousel 64 to a controlled height by the action of an insertion cam means 227 as shown in FIG. 17.

Figure 19A:
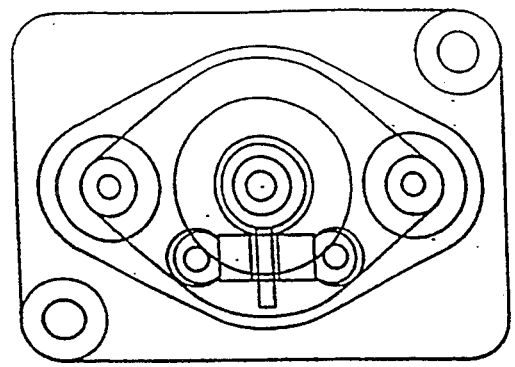
FIG. 19 is a side sectional view in isolation of the MEIA cartridge ejector.
Figure 19B:
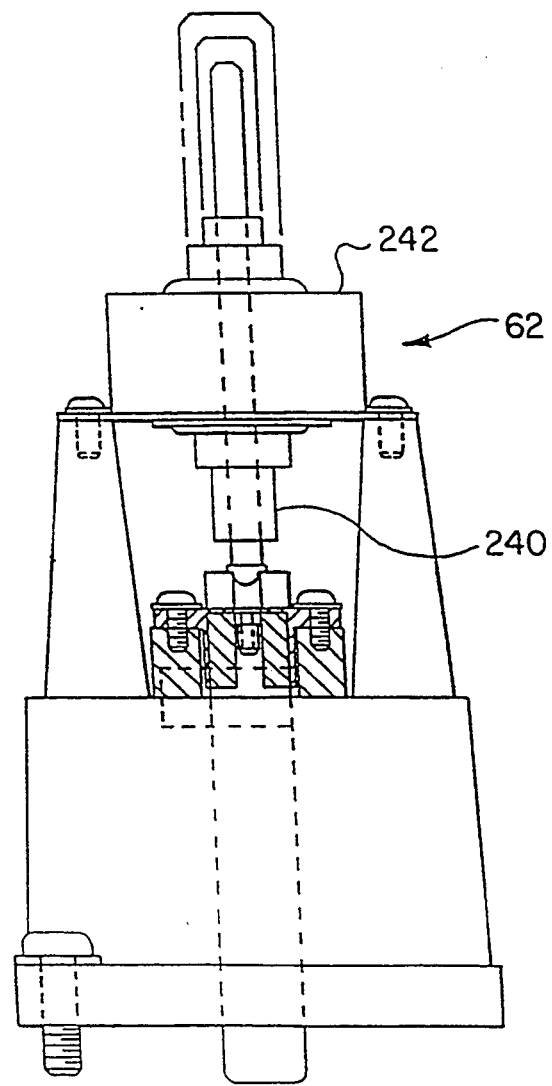

A side view of a MEIA cartridge ejector 62 is illustrated in FIG. 19. The cartridge ejector 62 functions through an ejector rod 240 and can be driven by manual or automatic drive means 242. The ejected MEIA cartridge is ejected through an ejection passage to the solid waste 198 container.

Figure 20:
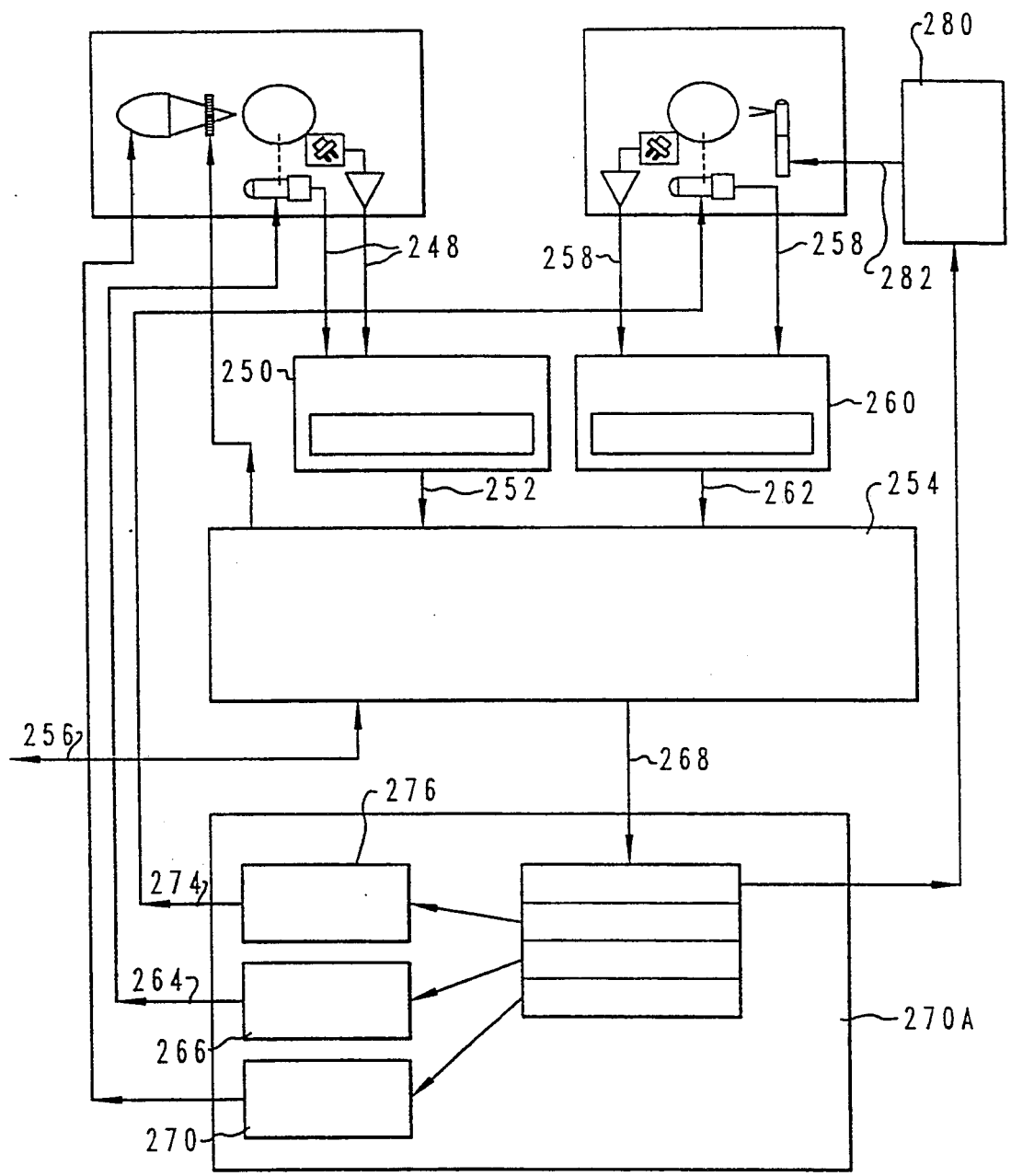
FIG. 20 is a box diagram of the system's optics signal processor.

A box diagram of the optics signal processor of the automated immunoassay analytical system is provided in FIG. 20 wherein the signal from the FPIA optics 248 is fed to a DSP A/D 250 which also sends serial bus signal 252 from an optic signal processor 8-bit microcontroller 254. The controller 254 is connected to computer elements through 256. Signal from the MEIA optics 258 are fed into a DSP A/D element 260 which also sends serial bus 262 from the controller 254. Signal is fed to the FPIA optics through 264 from high voltage power supply 266 and serial bus 268 which is in communication between the microcontroller 254 and the optics power supply board 270A. The FPIA tungsten lamp power supply FPIA 270 is in electronic communication with the FPIA optics 248. Signal is sent to the MEIA optics through 274 from high voltage power supply 276 which is in communication through serial bus 268 to the microcontroller 254 and mercury lamp power supply MEIA 280. The MEIA mercury lamp power supply 280 is also in electronic communication with MEIA optics through 282.

Figure 21:
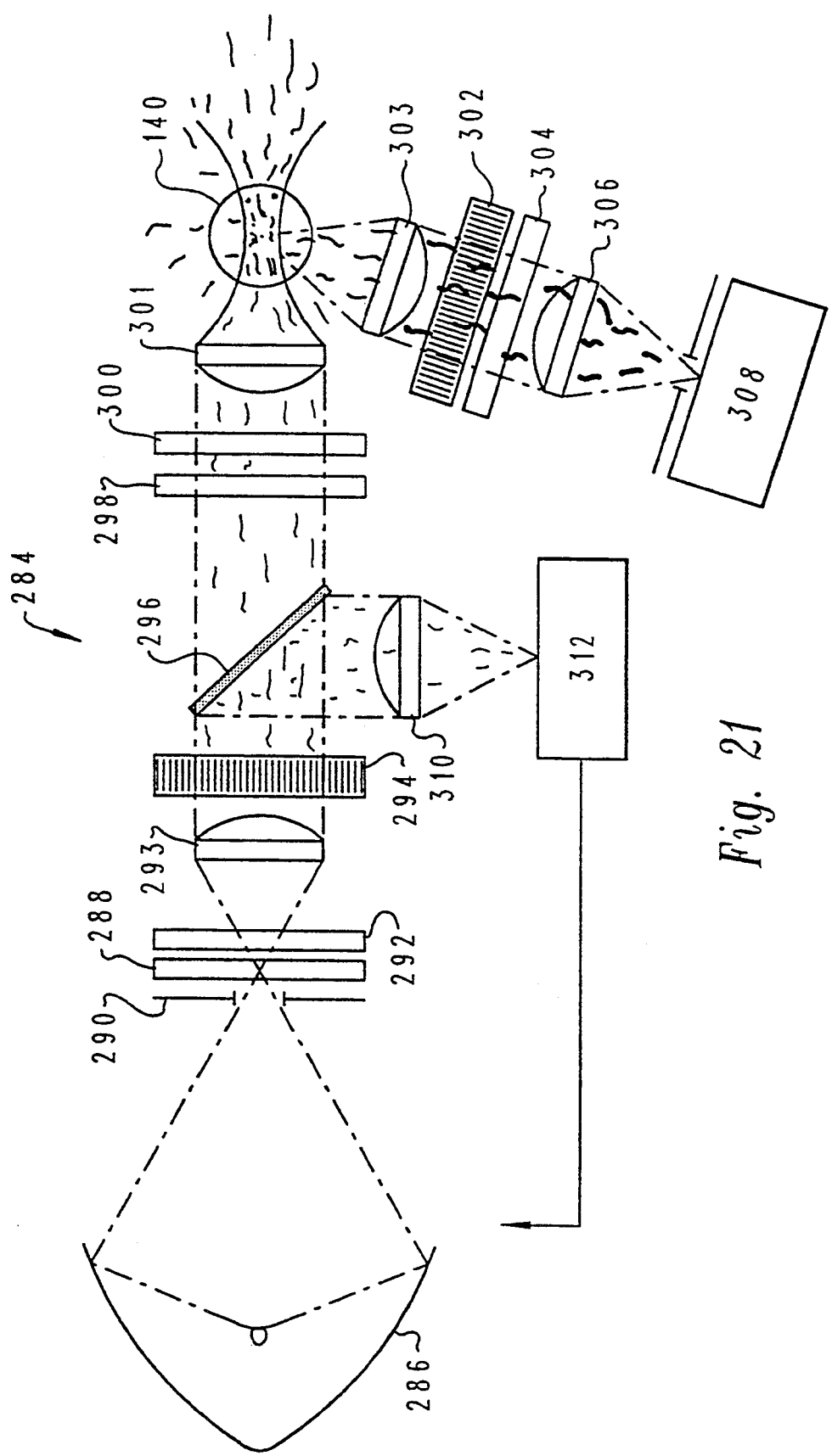
FIG. 21 is a schematic of the FPIA optical system.

A schematic view of the FPIA optical system 284 is shown in FIG. 21. The FPIA optical system 284 has a tungsten halogen source lamp 286 which focuses light through a heat reflector 288, an aperture 290 and heat absorber 292 to a lens 293 for introduction into an excitation filter 294. The light energy is then contacted with a beam splitter 296 which presents part of the beam to a polarizer 298 and liquid crystal 300. The light continues into another lens 301 before being focused on the cuvette 140 containing the FPIA reaction mixture. Light is emitted from the cuvette through lens means 303 before entering an emission filter 302. The reflected light from the emission filter 302 passes through a polarizer 304 before going to a focusing lens 306 and being focused for feed into photo multiplier tube 308. The beam splitter 296 splits out part of the light from the original source through lens 310 into a reference detector 312 which, in turn, controls the tungsten halogen source lamp.

Figure 22:
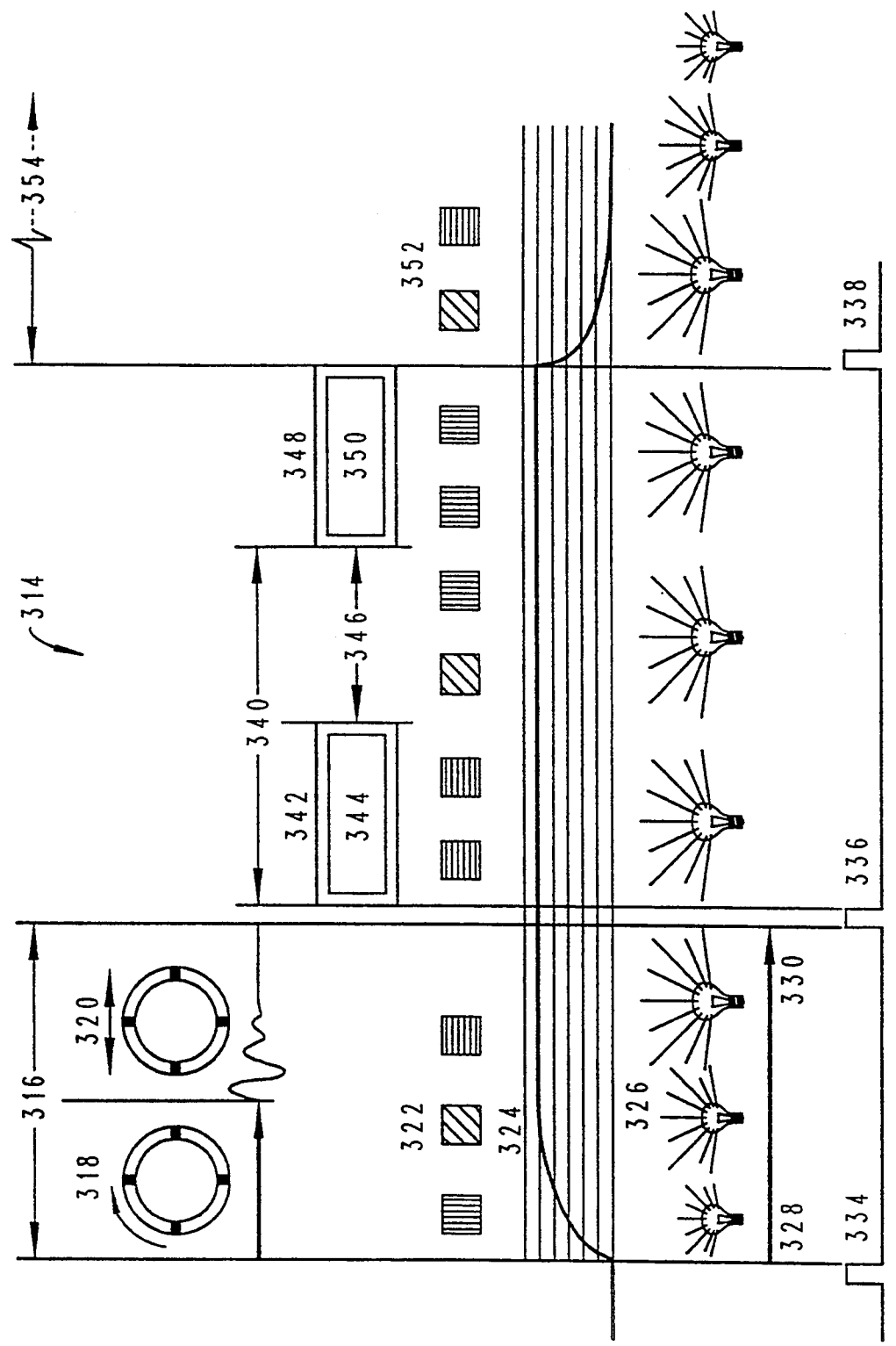
FIG. 22 is a schematic of the FPIA read[er] sequence.
Figure 23:
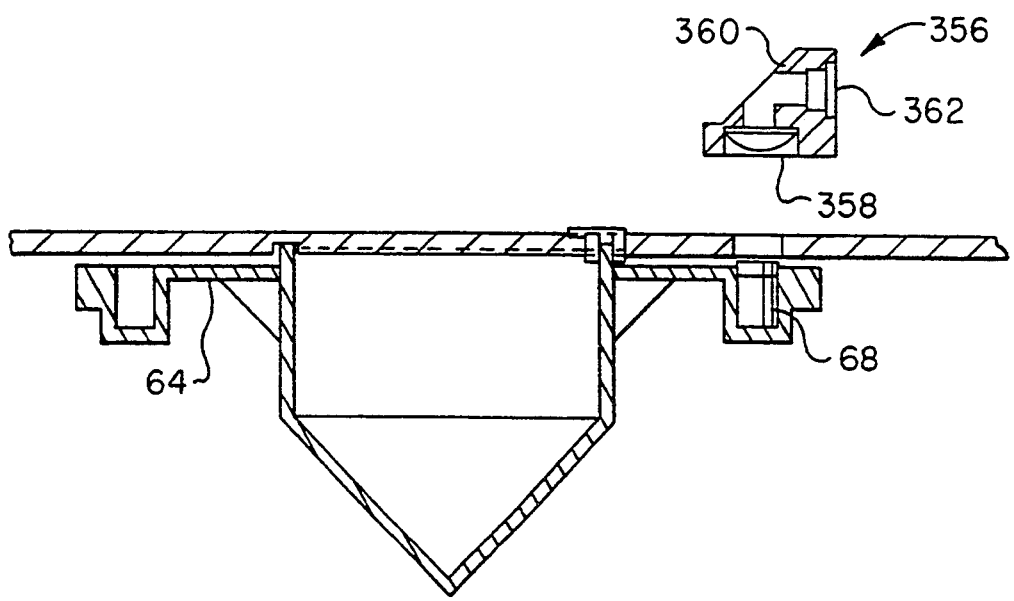
FIG. 23 is a side sectional view in isolation of a MEIA cartridge carousel, cartridge and MEIA reader.

A schematic view of the FPIA read sequence 314 is presented in FIG. 22. The FPIA read sequence 314 has a pre-read time 316 divided into carousel move time 318 and carousel settle time 320. Sub-read interval 340 is divided into a horizontal sub-read 342, A/D converter settle time 344, and a liquid crystal activation time 346. A vertical sub-read interval is identified by 348 which is inclusive of A/D converter settle time 350. Liquid crystal relaxation time is indicated by 352. The liquid crystal relaxation time 352 is illustrated in a pre-read time sequence. High voltage settle time 324 is further illustrated by lamp settle time 326 that shows the lamps in a simmer 328 and full burn 330 activation. Activities of the FPIA read sequence 314 provide for activities where scheduling windows 332 as exemplified by read prep 334, read parameter 336 during which the lamps are at full burn, and collection results 338 during the lamp settlement time and liquid crystal relaxation time 352.

Figure 24:
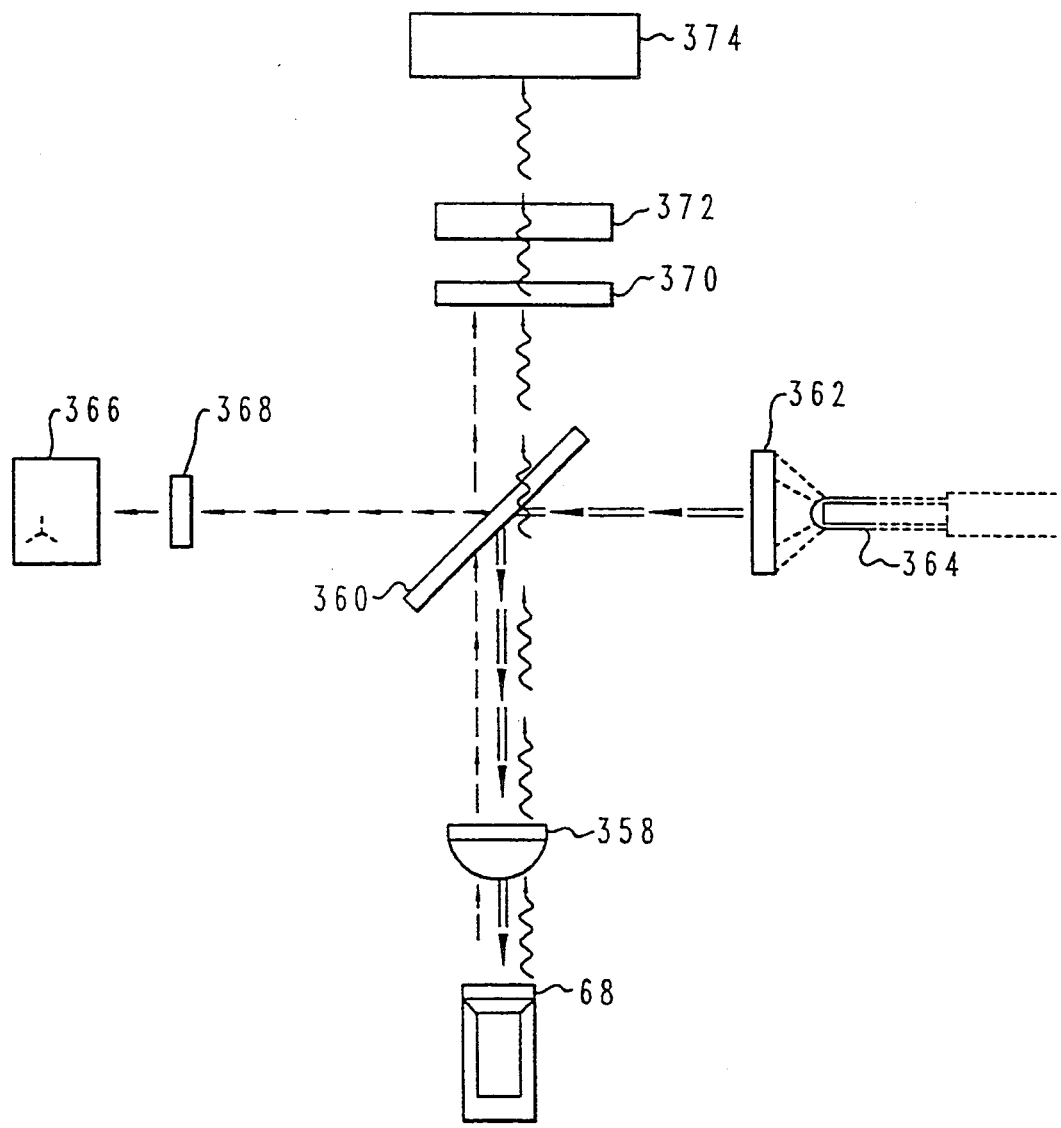
FIG. 24 is a schematic of the MEIA system optical assembly.

FIG. 24 is a schematic view of the MEIA system optical assembly 364. An MEIA light source is provided by mercury source lamp 364 which passes light through an excitation filter 362 to a filter reflector 360 before being fed through lens 358 into MEIA cartridge 68. Reflected fluorescent light is fed back through the filter 360 to a photomultiplier tube 374 after passing through a wide band-pass emission filter 370 and narrow band-pass emission filter 372. Part of the light energy from the mercury source lamp 364 passes directly through filter 360 to a bandpass filter 368 before influencing the photo diode 366.

Figure 25:
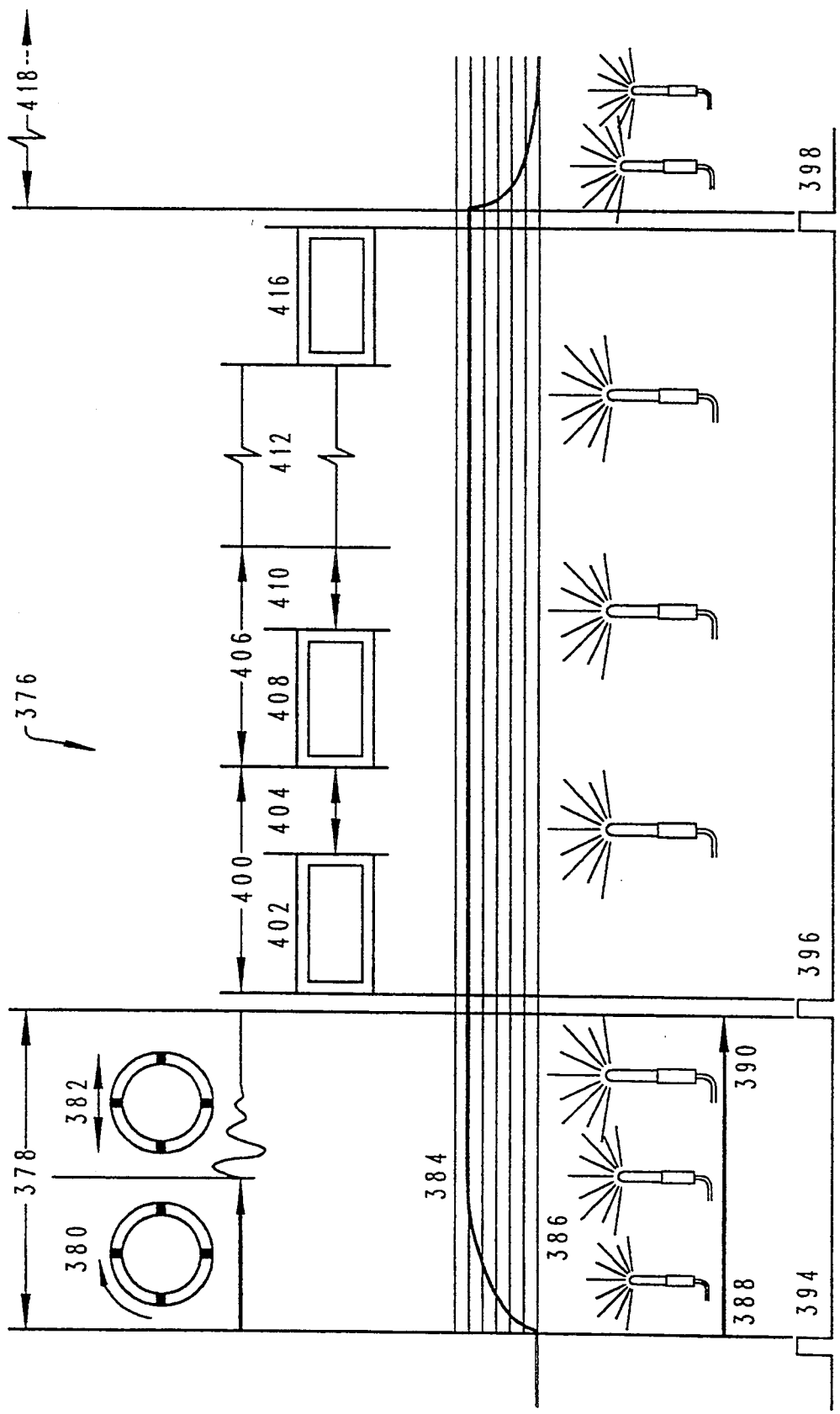
FIG. 25 is a schematic of the MEIA read sequence.

An MEIA read sequence schematic is presented in FIG. 25 wherein the MEIA read sequence 376 has a pre-read time 378 inclusive of carousel move time 380 and carousel settle time 382. High voltage settle time is indicated by graph 384 which is coincident with the lamp settlement time 386 showing lamp simmer 388 and lamp full burn 390. MEIA read sequence 376 has activities with scheduling windows 392 inclusive of read prep 394, read parameter 396 and collection results 398. The actual MEIA read sequence 376 is inclusive of sub-read interval 400 having a sub-read 402 and a dwell time 404. Another segment of the MEIA read sequence 376 is indicated by sub-read interval 406 inclusive of sub-read number to 408 and dwell time 410 with additional sub-read 412 and final sub-read 416. The next possible pre-read time is indicated by 418.

Multiple automated assay analytical systems are feasible through use of the apparatus, software, hardware and process technology of the present invention and include, but are not intended to be limited to, the following menus: ferritin, creatinine kirase MB (CK-MB), digoxin, phenytoin, phenobarbitol, carbamazepine, vancomycin, valproic acid, quinidine, leutinizing hormone (LH), follicle stimulating hormone (FSH), estradiol, progesterone, IgE, vitamin B2micro globulin, glycated hemoglobin (Gly. Hb), cortisol, digitoxin, N-acetylprocainamide (NAPA), procainamide, rubella-IgG, rubella-IgM, toxoplasmosis IgG (Toxo-IgG), toxoplasmosis IgM (Toxo-IgM), testosterone, saliaylates, acetaminophen, hepatitis B surface antigen (HBsAg), anti-hepatitis B core antigen IgG IgM (Anti-HBc), human immune deficiency virus 1 and 2 (HIV 1 and 2), human T-cell leukemia virus 1 and 2 (HTLV), hepatitis B envelope antigen (HBeAg), anti-hepatitis B envelope antigen (Anti-HBe), thyroid stimulating hormone (TSH), thyroxine (T4), total triiodothyronine (Total T3), free triiodothyronine (Free T3), carcinoembryoic antigen (CEA), and alpha feta protein (AFP).

In order to insure consistent, rapid resuspension and continued mixing of reagents with minimal operator involvement, the reagents are mixed automatically each time a new reagent pack is added to the reagent carousel, and periodically during instrument operation. This automated mixing can be accomplished by a back and forth motion of the reagent carousel with asymmetric pauses and is complete within approximately 1–2 minutes. The carousel acceleration, velocity, distance moved, and pause asymmetry are optimized to yield the most rapid reagent resuspension without foaming or bubble formation for the range of fill volumes used on the instrument.

Automated reagent mixing provides the following benefits. The operator need not manually mix (e.g. by inversion or shaking) reagents which have been stored prior to their placement on the instrument. This allows the reagents to be loaded onto the instrument in less time and with less involvement of the operator. There is less tendency for reagents to foam or form bubbles with automatic mixing than with manual mixing such as inversion. Foam and bubble formations are detrimental to instrument function and can negatively impact assay performance. Automated mixing insures that reagents are always mixed sufficiently and that they are mixed consistently. Occasional automatic mixing during instrument operation keeps reagents in a consistent suspension, and makes it unnecessary for the operator to periodically remove reagent packs in order to mix the reagents. In some circumstances, automated mixing can dissipate bubbles present at the start of mixing. A detailed description of kitting and process activities according to the invention are presented in the following for FPIA procedures; system description of process activities for a phenobarbital assay; and MEIA procedures for a CEA assay.

It is to be appreciated that the following description comprises an outline of the various functions and steps involved in preferred methods of the automated analytical system of the invention, which functions and methods as also will be appreciated by those skilled in the art, are conducted under computer control using various types of mathmetical algorithms and associated com-

DESCRIPTION OF KITTING AND PROCESS AREA ACTIVITIES

FPIA

System Description of Kitting Area (Phenobarbital assay)

Assumptions

Analyzer is in Standby/Ready mode when sample is loaded. System has been previously initialized. (All motors are homed, syringe and pumps are purged, all electronics and sensors are checked.)

Waste has been emptied, Diluent, MEIA buffer, MUP, and Quat bulk liquid consumables have been checked for sufficient volume.

All Consumable inventory files have been updated.

Preparation Steps

1) User loads empty Reaction Vessel (RV) into RV carousel.

2) To load a reagent pack(s), the user must first pause the front end carousels. The system will complete kitting of the current test and transfer the test to the process area.

3) User opens the reagent carousel cover, loads reagent pack(s) into reagent carousel, closes the reagent carousel cover, then resumes the front-end.

4) Instrument automatically scans all reagent packs onboard to verify reagent status.

Each reagent pack is positioned in front of the reagent pack barcode reader by rotation of the reagent carousel.

Reagent pack barcode reader reads barcode to identify assay type and carousel location.

If the barcode is unreadable, the system will request a barcode override.

If the barcode is good or override complete, the system will check the system inventory. The user will be notified if the pack is found to be empty, invalid or outdated.

Once the reagent pack is found to be good, it is ready to use.

Requesting a Test

1) User has two options for requesting a test or group of tests on one or more patient samples.

a) User may download the test request loadlist from a host computer to create an order list.

b) User enters test request or creates an order list on the System directly.

2) If sample cups (no barcode) are used, the following scenario occurs:

User refers to order list for segment ID and position number to place sample.

User loads a sample cup into referenced position in segment.

User transfers patient sample from blood collection tube into sample cup.

Segment is placed into sample carousel.

Indication is made to instrument that samples have been loaded

Instrument checks consumable inventories, waste status, cal status, etc.

Sample carousel rotates segment to segment identification reader.

Instrument reads segment identification.

3) If primary tubes (with barcode) are used, the following scenario occurs:

User loads primary tube into next available segment location on sample carousel. (Two types of carriers are used for primary tubes: one for tubes with heights of 75 mm and a second for tubes with heights of 100 mm.)

Indication is made to instrument that samples are available to be run.

Instrument checks consumable inventories, waste status, cal status, etc.

Scheduling a Test

1) When the sample is presented to the pipettor, the System attempts to schedule the tests ordered on that sample for processing. Each test ordered for the sample will be scheduled separately.

The System checks for adequate inventory (reagent packs, cartridges, buffer, MUP), system resources, sample time to complete the test.

It checks for valid calibration or orders for them on the order list.

If all test requirements are met, the test is scheduled for processing.

If all test requirements are not met, the test request is moved to the exception list. Once the test requirements have been met, the test request is moved back to the order list by the user.

2) When a test has been scheduled, the System moves it to the processing list and attempts to schedule other tests ordered for that sample.

3) When all tests for the current sample have been kitted, the System advances to the next sample on the sample carousel.

Kitting a Test

1) Once a test is scheduled, it is immediately kitted. (No tests are kitted until the scheduler ensures that the test can be transferred onto the process carousel immediately and processed within the timing requirements of the assay.)

2) RV carousel is rotated clockwise until an RV is detected in pipette axis position.

3) Reagent pack carousel is rotated until reagent pack for test ordered is at the actuator position. The actuator opens the reagent cartridge caps and the reagent pack carousel is then rotated until reagent pack for test ordered is in the pipette axis position. After all pipetting steps have been completed, the reagent pack carousel is rotated back to the actuator position where the reagent cartridge caps are closed.

4) Sample carousel is rotated until sample cup (or primary tube) is in pipette axis position.

5) Pipette is always at "HOME" position (Pipette R-axis is parked over wash station and Pipette Z-axis is at the Z-clear position) when not in use.

6) Sample kitting

Sample aspirate

Syringe aspirates "X" uL of air at a rate of "X" uL/sec.

Pipette R-axis is moved over sample cup.

Pipette Z-axis is moved down to the Z-above position.

LLS is enabled to ensure that no liquid is currently detected.

Pipette Z-axis is moved down at constant speed until fluid is detected OR until Z-Asp limit has been reached. *IT WILL BE ASSUMED THAT FLUID IS DETECTED*

Based on the Z-height position at which fluid is detected and the Z-height/volume table, the System calculates the volume of fluid in the well and compares it to the volume specified in the pipetting description. If sufficient volume is present in the well, the aspiration sequence is initiated. (If insufficient volume is present, the test is aborted and the test request moved to the exception list. The exception list provides notice to an operator of tests which cannot be completed.)

The following occur simultaneously until the total volume of sample required is aspirated:

Pipette Z-axis motor is moved down at a rate of "X" steps/sec.
Syringe motor aspirates "X" uL at a rate of "X" uL/sec.
LLS is checked to ensure probe still in liquid
Liquid Level Sense (LLS) is disabled.
Pipette Z-axis is moved up to Z-clear position.
Pipette R-axis is moved over the RV sample well.
Pipette Z-axis is moved down to the dispense position within the RV sample well.
Syringe dispenses "X" uL of sample at a rate of "X" uL/sec.
Pipette Z-axis is moved up to Z-clear position.
Probe Post-wash
The probe is washed to ensure that it is free from contamination.
NOTE: All pipette activities (in both kitting and process areas) are followed with a probe post-wash to minimize carryover from one fluid aspirate to another. In some cases, pipette activities may be preceded with a probe pre-wash if necessary to guarantee the validity of the next fluid aspirate. For this assay description, it will be assumed that only a post-wash is used.
The inside of the probe is cleaned first.
Pipette R-axis is moved over waste area.
Pipette Z-axis is moved down to appropriate position within the waste area.
The wash valve is opened for the amount of time specified in the assay protocol.
Wash valve is closed.
Pipette Z-axis is moved up to the Z-clear position.
The outside of the probe is cleaned next.
Pipette R-axis is moved over wash cup.
Pipette Z-axis is moved down to wash position within the wash cup.
The wash valve is opened for the amount of time specified in the assay protocol.
Wash valve is closed.
Pipette is returned to "HOME" position.

7) Popper kitting (Popper is defined as a substance which eliminates in general interfering substances in assays such as, for example, those discussed and claimed in U.S. Pat. No. 4,492,762 issued Jan. 8, 1985 and hereby incorporated by reference.)

Popper aspirate
Syringe aspirates "X" uL of air at a rate of "X" uL/sec.
Pipette R-Axis is moved over the popper reagent bottle in the Reagent Pack.
Pipette Z-axis is moved down to the Z-above position.
LLS is enabled to ensure no liquid currently detected.
Pipette Z-axis is moved down at constant speed until fluid is detected OR until the Z-aspriation-lower (Z-Asp) limit is reached. *IT WILL BE ASSUMED THAT FLUID IS DETECTED*
Based on the Z-height position at which fluid is detected and the Z-height/volume table, the System calculates the volume of fluid in the well and compares it to the volume specified in the pipetting description. If sufficient volume is present in the well, the aspiration sequence is initiated. (If sufficient volume is not present, the test is aborted and the test request moved to the exception list.)

The following occur simultaneously until the total volume of popper required is aspirated:

Pipette Z-axis motor is moved down at a rate of "X" steps/sec.
Syringe aspirates "X" uL at a rate of "X" uL/sec.
LLS is checked to ensure probe still in liquid.
LLS is disabled.
Pipette Z-axis is moved up to Z-clear position.
Pipette R-axis is moved over the RV reagent 1 well.
Pipette Z-axis is moved down to the dispense position within the RV reagent 1 well.
Syringe dispenses "X" uL of popper at a rate of "X" uL/sec.
Pipette Z-axis is moved up to Z-clear position.
Probe Post-wash
The probe is again washed to ensure that it is free from contamination as described in #6 - SAMPLE KITTING.

8) Antiserum kitting

Antiserum aspirate
Syringe aspirates "X" uL of air at a rate of "X" uL/sec.
Pipette R-Axis is moved over the antiserum reagent bottle in the Reagent Pack.
Pipette Z-axis is moved down to the Z-above position.
LLS is enabled to ensure no liquid currently detected.
Pipette Z-axis is moved down at constant speed until fluid is detected OR until the Z-Asp limit is reached. *IT WILL BE ASSUMED THAT FLUID IS DETECTED*
Based on the Z-height position at which fluid is detected and the Z-height/volume table, the System calculates the volume of fluid in the well and compares it to the volume specified in the pipetting description. If sufficient volume is present in the well, the aspiration sequence is initiated. (If sufficient volume is not present, the test is aborted and the test request moved to the exception list.)

The following occur simultaneously until the total volume of antiserum required is aspirated:

Pipette Z-axis motor is moved down at a rate of "X" steps/sec.
Syringe aspirates "X" micro liter (uL) at a rate of "X" uL/sec.
LLS is checked to ensure probe still in liquid.
LLS is disabled.
Pipette Z-axis is moved up to Z-clear position.
Pipette R-axis is moved over the RV reagent 2 well.
Pipette Z-axis is moved down to the dispense position within the RV reagent 2 well.
Syringe dispenses "X" uL of antiserum at a rate of "X" uL/sec.
Pipette Z-axis is moved up to Z-clear position.
Probe Post-wash
The probe is again washed to ensure that it is free from contamination as described in #6 - SAMPLE KITTING.

9) Tracer kitting

Tracer aspirate
Syringe aspirates "X" uL of air at a rate of "X" uL/sec.

Pipette R-Axis is moved over the tracer reagent bottle in the Reagent Pack.
Pipette Z-axis is moved down to the Z-above position.
LLS is enabled to ensure no liquid currently detected.
Pipette Z-axis is moved down at constant speed until fluid is detected OR until the Z-Asp limit is reached. *IT WILL BE ASSUMED THAT FLUID IS DETECTED*
Based on the Z-height position at which fluid is detected and the Z-height/volume table, the System calculates the volume of fluid in the well and compares it to the volume specified in the pipetting description. If sufficient volume is present in the well, the aspiration sequence is initiated. (If sufficient volume not is present, the test is aborted and the test request moved to the exception list.)
The following occur simultaneously until the total volume of tracer required is aspirated:
Pipette Z-axis motor is moved down at a rate of "X" steps/sec.
Syringe aspirates "X" uL at a rate of "X" uL/sec.
LLS is checked to ensure probe still in liquid.
LLS is disabled.
Pipette Z-axis is moved up to Z-clear position.
Pipette R-axis is moved over the RV reagent 3 well.
Pipette Z-axis is moved down to the dispense position within the RV reagent 2 well.
Syringe dispenses "X" uL of tracer at a rate of "X" uL/sec.
Pipette Z-axis is moved up to Z-clear position.
Probe Post-wash
The probe is again washed to ensure that it is free from contamination as described in #6 - SAMPLE KITTING.
Kitting Complete
Transfer of RV Into Process Area
1) RV carousel is rotated to transfer station.
2) Process carousel is rotated so that the empty position is aligned with the transfer station.
3) Transfer mechanism O-axis is rotated to sample entry area.
4) Transfer mechanism R-axis grabs the RV and pulls it into the transfer mechanism.
5) Transfer mechanism O-axis is rotated so that RV is aligned with the empty position on the process carousel.
6) RV is loaded onto process carousel.

SYSTEM DESCRIPTION OF PROCESS AREA (PHENOBARBITAL ASSAY)

Wait for temperature equilibration time and evaporation window to expire.

1ST PIPETTE ACTIVITY - BLANK (DILUTED SAMPLE AND POPPER)

Pipette
1) Incubation timer is set according to assay file specifications.
2) Precision diluent aspirate
The following activities are performed simultaneously:
Syringe aspirates "X" uL at a rate of "X" uL/sec.
Wash valve is opened.
Wait "n" seconds.
Wash valve is closed.
3) Sample aspirate
Pipette R-axis is moved over the RV sample well.
LLS is enabled to ensure no liquid currently detected.
Pipette Z-axis is moved down at constant speed until fluid is detected OR until the Z-Asp limit is reached. *IT WILL BE ASSUMED THAT FLUID IS DETECTED*
Based on the Z-height position at which fluid is detected and the Z-height/volume table, the System calculates the volume of fluid in the well and compares it to the volume specified in the pipetting description. If sufficient volume is present, the aspiration sequence is initiated. (If sufficient volume is not present, the test is aborted and the test request moved to the exception list.)
The following occur simultaneously until the total volume of sample required is aspirated:
Pipettor Z-axis motor is moved down at a rate of "X" steps/sec.
Syringe aspirates "X" uL of sample at a rate of "X" uL/sec.
LLS is checked to ensure probe still in liquid.
LLS is disabled.
Pipette Z-axis is moved up to Z-above position.
4) Diluent/sample dispensed to the RV predilute well
Pipette R-axis is moved over the RV predilute well.
Pipette Z-axis is moved down to the dispense position within the RV predilute well.
Syringe dispenses "X" uL of diluent/sample at a rate of "X" uL/sec.
Pipette Z-axis is moved up to Z-clear position.
5) Probe Post-wash
The probe is again washed to ensure that it is free from contamination as described in #6 - SAMPLE KITTING.
6) Precision diluent aspirate
The following activities are performed simultaneously:
Syringe aspirates "X" uL at a rate of "X" uL/sec.
Wash valve is opened.
Wait "n" seconds.
Wash valve is closed.
7) Popper aspirate
Pipette R-axis is moved over the RV Reagent (popper) well.
LLS is enabled to ensure no liquid currently detected.
Pipette Z-axis is moved down at constant speed until fluid is detected OR until the Z-Asp limit is reached. *IT WILL BE ASSUMED THAT FLUID IS DETECTED*
Based on the Z-height position at which fluid is detected and the Z-height/volume table, the System calculates the volume of fluid in the well and compares it to the volume specified in the pipetting description. If sufficient volume is present, the aspiration sequence is initiated. (If sufficient volume is not present, the test is aborted and the test request moved to the exception list.)
The following occur simultaneously until the total volume of popper required is aspirated:
Pipette Z-axis motor is moved down at a rate of "X" steps/sec.
SYRINGE aspirates "X" uL at a rate of "X" uL/sec.
LLS is checked to ensure probe still in liquid.
LLS is disabled.
Pipette Z-axis is moved up to the Z-above position.
8) Diluted sample aspirate
Pipette R-axis is moved over the RV predilute well.
LLS is enabled to ensure no liquid currently detected.
Pipette Z-axis is moved down at constant speed until fluid is detected OR until the Z-Asp limit is reached. *IT WILL BE ASSUMED THAT FLUID IS DETECTED*

Based on the Z-height position at which fluid is detected and the Z-height/volume table, the System calculates the volume of fluid in the well and compares it to the volume specified in the pipetting description. If sufficient volume is present, the aspiration sequence is initiated. (If sufficient volume is not present, the test is aborted and the test request moved to the exception list.)

The following occur simultaneously until the total volume of diluted sample required is aspirated:

Pipette Z-axis motor is moved down at a rate of "X" steps/sec.
SYRINGE aspirates "X" uL at a rate of "X" uL/sec.
LLS is checked to ensure probe still in liquid.
LLS is disabled.
Pipette Z-axis is moved up to the Z-above position.

11) Diluted sample/popper/diluent dispensed to RV cuvette

Pipette R-axis is moved over to the RV cuvette position.
Pipette Z-axis is moved down to the dispense position in the RV cuvette.
SYRINGE dispenses "X" uL of diluted sample/popper/diluent at a rate of "X" uL/sec.
Pipette Z-axis is moved up to the Z-above position.
Probe Post-wash
The probe is again washed to ensure that it is free from contamination as described in #6 - SAMPLE KITTING.

1ST PIPETTE ACTIVITY COMPLETE
Check incubation timer. When expires start next activity.

The FPIA reader is prepared to take a read:
Lamp intensity is brought from simmer state to burn state.
Photo Multiplier Tube (PMT) gain is set.

BLANK READ (BACKGROUND)

1) Incubation timer is set according to assay file specifications.
2) Process carousel is rotated so that the RV is at the read station.
3) Horizontal intensity is read for "X.XX" secs.
4) The crystal is flipped for the vertical read.
5) Wait "n" seconds until the crystal settles.
6) Vertical intensity is read for "X.XX" seconds.
7) The raw reads are converted to normalized reads (light intensity hitting detector/lamp intensity) by the optics microprocessor.
8) Background reads are stored.
9) System calculates BLANK I.
READ COMPLETE
Check incubation timer. When expires start next activity.

2ND PIPETTE ACTIVITY - REACTION (DILUTED SAMPLE/POPPER/TRACER/ANTISERUM)

Pipette
1) Incubation timer is set according to assay file specifications.
2) Precision diluent aspirate
The following activities are performed simultaneously:
Syringe aspirates "X" uL at a rate of "X" uL/sec.
Wash valve is opened.
Wait "n" seconds.
Wash valve is closed.
3) Antiserum aspirate
Pipette R-axis is moved over the RV Reagent 2 (antiserum) well.
LLS is enabled to ensure no liquid currently detected.
Pipette Z-axis is moved down at constant speed until fluid is detected OR until the Z-Asp limit is reached. *IT WILL BE ASSUMED THAT FLUID IS DETECTED*

Based on the Z-height position at which fluid is detected and the Z-height/volume table, the System calculates the volume of fluid in the well and compares it to the volume specified in the pipetting description. If sufficient volume is present, the aspiration sequence is initiated. (If sufficient volume is not present, the test is aborted and the test request moved to the exception list.)

The following occur simultaneously until the total volume of antiserum required is aspirated:

Pipette Z-axis motor is moved down at a rate of "X" steps/sec.
SYRINGE aspirates "X" uL at a rate of "X" uL/sec.
LLS is checked to ensure probe still in liquid.
LLS is disabled.
Pipette Z-axis is moved up to the Z-above position.

4) Tracer aspirate
SYRINGE aspirates "X" uL of air at a rate of "X" uL/sec.
Pipette R-axis is moved over the RV Reagent 3 (tracer) well.
LLS is enabled to ensure no liquid currently detected.
Pipette Z-axis is moved down at constant speed until fluid is detected OR until the Z-Asp limit is reached. *IT WILL BE ASSUMED THAT FLUID IS DETECTED*

Based on the Z-height position at which fluid is detected and the Z-height/volume table, the System calculates the volume of fluid in the well and compares it to the volume specified in the pipetting description. If sufficient volume is present, the aspiration sequence is initiated. (If sufficient volume is not present, the test is aborted and the test request moved to the exception list.)

The following occur simultaneously until the total volume of tracer required is aspirated:

Pipette Z-axis motor is moved down at a rate of "X" steps/sec.
Syringe aspirates "X" uL at a rate of "X" uL/sec.
LLS is checked to ensure probe still in liquid.
LLS is disabled.
Pipette Z-axis is moved up to the Z-above position.

5) Diluted sample aspirate
Pipette R-axis is moved over the RV predilute well.
LLS is enabled to ensure no liquid currently detected.
Pipette Z-axis is moved down at constant speed until fluid is detected OR until the Z-Asp limit is reached. *IT WILL BE ASSUMED THAT FLUID IS DETECTED*

Based on the Z-height position at which fluid is detected and the Z-height/volume table, the System calculates the volume of fluid in the well and compares it to the volume specified in the pipetting description. If sufficient volume is present, the aspiration sequence is initiated. (If sufficient volume is not present, the test is aborted and the test request moved to the exception list.)

The following occur simultaneously until the total volume of diluted sample required is aspirated:

Pipette Z-axis motor is moved down at a rate of "X" steps/sec.

Syringe aspirates "X" uL at a rate of "X" uL/sec.

LLS is checked to ensure probe still in liquid.

LLS is disabled.

Pipette Z-axis is moved up to the Z-above position.

6) Diluted sample/tracer/air/antiserum/diluent dispensed to RV cuvette

Pipette R-axis is moved over to the RV cuvette position.

Pipette Z-axis is moved down to the dispense position in the RV cuvette.

Syringe dispenses "X" uL of diluted sample/tracer/air/antiserum/diluent at a rate of "X" uL/sec.

Pipette Z-axis is moved up to the Z-above position.

Probe Post-wash

The probe is again washed to ensure that it is free from contamination as described in #6 - SAMPLE KITTING.

2ND PIPETTE COMPLETE

Check incubation timer. When expires start next activity.

The FPIA reader is prepared to take a read:

Lamp intensity is brought from simmer state to burn state.

PMT gain is set.

Final Read

1) Process carousel is rotated so that the RV is at the read station.

2) Horizontal intensity is read for "X.XX" secs.

3) The crystal is flipped for the vertical read.

4) The System delays "n" seconds until the crystal settles.

5) Vertical intensity is read for "X.XX" seconds.

6) The raw reads are converted to normalized reads (light intensity hitting detector/lamp intensity) by the optics microprocessor.

7) Reads are stored.

8) System calculates NET intensity (I) and milipolarization (mP).

9) mP value is fitted to calibration curve to yield a concentration result.

READ COMPLETE

RV UNLOAD (This activity occurs when resources are not in use.)

1) The following are performed simultaneously:

Process carousel is rotated so that the empty position is at the transfer station.

Transfer mechanism O-axis is moved to process carousel.

2) RV is grabbed with the transfer mechanism R-axis and pulled into the transfer mechanism.

3) Transfer mechanism O-axis is rotated so that RV is aligned with the waste container.

4) RV is pushed into the waste container.

KITTING AND PROCESS AREA ACTIVITIES

MEIA

System Description of Kitting Area (CEA Assay)

Assumptions

Analyzer is in Standby/Ready mode when sample is loaded. System has been previously initialized. (All motors are homed, syringe and pumps are purged, all electronics and sensors are checked.)

Waste has been emptied, dilution, MEIA buffer, MUP, and Quat bulk liquid consumables have been checked for sufficient volume.

Cartridges have been placed into hopper and are available for loading onto auxiliary carousel when needed (for MEIA assays only).

All Consumable inventory files have been updated.

Preparation Steps

1) User loads empty RVs into RV carousel.

2) To load a reagent pack(s), the user must first pause the front end carousels. The system will complete kitting of the current test and transfer the test to the process area.

3) User opens the reagent carousel, loads reagent pack(s) into reagent carousel, closes the reagent carousel cover, then resumes the front-end.

4) Instrument automatically scans all reagent packs onboard to verify reagent status.

Each reagent pack is positioned in front of the reagent pack barcode reader by rotation of the reagent carousel.

Reagent pack barcode reader reads barcode to identify assay type and carousel location.

If the barcode is unreadable, the system will request a barcode override.

If the barcode is good or override complete, the system will check the system inventory. The user will be notified if the pack is found to be empty, invalid or outdated.

Once the reagent pack is found to be good, it is ready to use.

Requesting a Test

1) User has two options for requesting a test or group of tests on one or more patient samples.

a) User may download the test request loadlist from a host computer to create an orderlist.

b) User enters test request or creates an order list on the System directly.

2) If sample cups (no barcode) are used, the following scenario occurs:

User refers to order list for segment ID and position number to place sample.

User loads a sample cup into referenced position in segment.

User transfers patient sample from blood collection tube into sample cup.

Segment is placed into sample carousel.

Indication is made to instrument that samples have been loaded.

Instrument checks consumable inventories, waste status, assay calibration, etc.

Sample carousel rotates segment to segment identification reader.

Instrument reads segment identification.

3) If primary tubes (with barcode) are used, the following scenario occurs:

User loads primary tube into next available segment location on sample carousel. (Two types of carriers are used for primary tubes: one for tubes with heights of 75 mm and a second for tubes with heights of 100 mm.)

Indication is made to instrument that samples are available to be run.

Sample carousel rotates segment to segment identification reader.

Scheduling a Test

1) When the sample is presented to the pipettor, the System attempts to schedule the tests ordered on that sample for processing. Each test ordered for the sample will be scheduled separately.

The System checks for adequate inventory (reagent packs, cartridges, buffer, MUP), system resources, sample time to complete the test.

It checks for valid calibration or orders for them on the order list.

If all test requirements are met, the test is scheduled for processing.

If all test requirements are not met, the test request is moved to the exception list. Once the test requirements have been met, the test request is moved back to the order list by the user.

2) When a test has been scheduled, the system moves it to the processing list and attempts to schedule other tests ordered for that sample.

3) When all tests for the current sample have been kitted, the System advances to the next sample on the sample carousel.

Kitting a Test

1) Once a test is scheduled, it is immediately kitted. (No tests are kitted until the scheduler ensures that the test can be transferred onto the process carousel immediately and processed within the timing requirements of the assay.)

2) RV carousel is rotated clockwise until an RV is detected in pipette axis position.

3) Reagent pack carousel is rotated until reagent pack for test ordered is at the actuator position. The actuator opens the reagent cartridge caps and the reagent pack carousel is then rotated until reagent pack for test ordered is in the pipette axis position. After all pipetting steps have been completed, the reagent pack carousel is rotated back to the actuator position where the reagent cartridge caps are closed.

4) Sample carousel is rotated until sample cup (or primary tube) is in pipette axis position.

5) Pipette is always at HOME position (Pipette R-axis is parked over wash station and Pipette Z-axis is at the Z-clear position) when not in use.

6) Sample kitting
Sample aspirate
Syringe aspirates "X" uL of air at a rate of "X" uL/sec.
Pipette R-axis is moved over sample cup.
Pipette Z-axis is moved down to the Z-above position.
Pipette Z-axis is moved down to the Z-LLS position.
LLS is enabled to ensure that no liquid is currently detected.
Pipette Z-axis is moved down at constant speed until fluid is detected OR until Z-Asp limit has been reached. *IT WILL BE ASSUMED THAT FLUID IS DETECTED*
Based on the Z-height position at which fluid is detected and the Z-height/volume table, the System calculates the volume of fluid in the well and compares it to the volume specified in the pipetting description. If sufficient volume is present in the well, the aspiration sequence is initiated. (If sufficient volume is not present, the test is aborted and the test request moved to the exception list.)
The following occur simultaneously until the total volume of sample required is aspirated:
Pipette Z-axis motor is moved down at a rate of "X" steps/sec.
Syringe aspirates "X" uL at a rate of "X" uL/sec.
LLS is checked to ensure probe still in liquid.
LLS is disabled.
Pipette Z-axis is moved up to Z-clear position.
Pipette R-axis is moved over the RV sample well.
Pipette Z-axis is moved down to the dispense position within the RV sample well.
Syringe dispenses "X" uL of sample at a rate of "X" uL/sec.
- Pipette Z-axis is moved up to Z-clear position.
Probe Post-wash
The probe is washed to ensure that it is free from contamination.
NOTE: Pipette activities (in both kitting and process areas) are generally followed with a probe post-wash to minimize carryover from one fluid aspirate to another. In some cases, pipette activities may be preceded with a probe pre-wash if necessary to guarantee the validity of the next fluid aspirate. For this assay description, it will be assumed that only a post-wash is used.
The inside of the probe is cleaned first.
Pipette R-axis is moved over waste area.
Pipette Z-axis is moved down to appropriate position within the waste area.
The wash valve is opened for the amount of time specified in the assay protocol.
Wash valve is closed.
Pipette Z-axis is moved up to the Z-clear position.
The outside of the probe is cleaned next.
Pipette R-axis is moved over wash cup.
Pipette Z-axis is moved down to wash position within the wash cup.
The wash valve is opened for the amount of time specified in the assay protocol.
Wash valve is closed.
Pipette is returned to "HOME" position.

7) Microparticle kitting
Microparticle aspirate
(Microparticles are pipetted directly into the RV incubation well to save on volume, as this is the most costly MEIA reagent.)
Syringe aspirates "X" uL of air at a rate of "X" uL/sec.
Pipette R-Axis is moved over the microparticle reagent bottle in the Reagent Pack.
Pipette Z-axis is moved down to the Z-above position.
Pipette Z-axis is moved down to the Z-LLS position.
LLS is enabled to ensure no liquid currently detected.
Pipette Z-axis is moved down at constant speed until fluid is detected OR until the Z-Asp limit is reached. *IT WILL BE ASSUMED THAT FLUID IS DETECTED*
Based on the Z-height position at which fluid is detected and the Z-height/volume table, the System calculates the volume of fluid in the well and compares it to the volume specified in the pipetting description. If sufficient volume is present in the well, the aspiration sequence is initiated. (If sufficient volume is not present, the test is aborted and the test request moved to the exception list.)
The following occur simultaneously until the total volume of microparticles required is aspirated:
Pipette Z-axis motor is moved down at a rate of "X" steps/sec.
Syringe aspirates "X" uL at a rate of "X" uL/sec.
LLS is checked to ensure probe still in liquid.
LLS is disabled.
Pipette Z-axis is moved up to Z-clear position.
Pipette R-axis is moved over the RV incubation well.

Pipette Z-axis is moved down to the dispense position within the RV incubation well.
Syringe dispenses "X" uL of microparticles at a rate of "X" uL/sec.
Pipette Z-axis is moved up to Z-clear position.
Probe Post-Wash
The probe is again washed to ensure that it is free from contamination as described in #6 - SAMPLE KITTING.

8) Conjugate kitting
Conjugate aspirate
(Conjugate, special wash fluid, and/or specimen diluent are pipetted into either RV reagent wells or RV predilution well, depending on volume requirements.)
Syringe aspirates "X" uL of air at a rate of "X" uL/sec.
Pipette R-Axis is moved over the conjugate reagent bottle in the Reagent Pack.
Pipette Z-axis is moved down to the Z-above position.
Pipette Z-axis is moved down to the Z-LLS position.
LLS is enabled to ensure no liquid currently detected.
Pipette Z-axis is moved down at constant speed until fluid is detected OR until the Z-Asp limit is reached. *IT WILL BE ASSUMED THAT FLUID IS DETECTED*
Based on the Z-height position at which fluid is detected and the Z-height/volume table, the System calculates the volume of fluid in the well and compares it to the volume specified in the pipetting description. If sufficient volume is present in the well, the aspiration sequence is initiated. (If sufficient volume is not present, the test is aborted and the test request moved to the exception list.)
The following occur simultaneously until the total volume of conjugate required is aspirated:
Pipette Z-axis motor is moved down at a rate of x steps/sec.
Syringe aspirates "X" uL at a rate of "X" uL/sec.
LLS is checked to ensure probe still in liquid.
LLS is disabled.
Pipette Z-axis is moved up to Z-clear position.
Pipette R-axis is moved over the RV reagent well.
Pipette Z-axis is moved down to the dispense position within the RV reagent well.
Syringe dispenses "X" uL of conjugate at a rate of "X" uL/sec.
Pipette Z-axis is moved up to Z-clear position.
Probe Post-Wash
The probe is again washed to ensure that it is free from contamination as described in #6 - SAMPLE KITTING.

9) MEIA buffer kitting
RV Carousel is rotated until RV buffer well is under the MEIA buffer dispenser at buffer kitting station.
"X" uL of MEIA buffer is dispensed into the buffer well at a rate of "X" uL/sec.
KITTING COMPLETE
Transferring RV Into Process Area
1) RV carousel is rotated to transfer station.
2) Process carousel is rotated so that the empty position is aligned with the transfer station.
3) Transfer mechanism O-axis is rotated to sample entry area.
4) Transfer mechanism R-axis grabs the RV and pulls it into the transfer mechanism.
5) Transfer mechanism O-axis is rotated so that RV is aligned with the empty position on the process carousel.
6) RV is loaded onto process carousel.

SYSTEM DESCRIPTION OF PROCESS AREA (CEA ASSAY)

System waits for temperature equilibration time and evaporation window to expire.

1ST PIPETTE ACTIVITY (MICROPARTICLE/SAMPLE REACTION)

Pipette
1) Incubation timer is set according to assay file specifications.
2) MEIA buffer aspirate
The process carousel is moved so that the RV is at the pipetting station.
Syringe aspirates "X" uL of air at a rate of "X" uL/sec.
Pipette R-axis is moved over the RV buffer well.
Pipette Z-axis is moved down to the Z-above position over the RV buffer well.
Pipette Z-axis is moved down to the Z-LLS position.
LLS is enabled to ensure no liquid currently detected.
Pipette Z-axis is moved down at constant speed until fluid is detected OR until the Z-Asp limit is reached. *IT WILL BE ASSUMED THAT FLUID IS DETECTED*
Based on the Z-height position at which fluid is detected and the Z-height/volume table, the System calculates the volume of fluid in the well and compares it to the volume specified in the pipetting description. If sufficient volume is present, the aspiration sequence is initiated. (If sufficient volume is not present, the test is aborted and the test request moved to the exception list.)
The following occur simultaneously until the total volume of MEIA buffer required is aspirated:
Pipette Z-axis motor is moved down at a rate of "X" steps/sec.
Syringe aspirates "X" uL at a rate of "X" uL/sec.
LLS is checked to ensure probe still in liquid.
LLS is disabled.
Pipette Z-axis is moved up to Z-above position.
3) Sample aspirate
Pipette R-axis is moved over the RV sample well.
Pipette Z-axis is moved down to the Z-LLS position.
LLS is enabled to ensure no liquid currently detected.
Pipette Z-axis is moved down at constant speed until fluid is detected OR until the Z-Asp limit is reached. *IT WILL BE ASSUMED THAT FLUID IS DETECTED*
Based on the Z-height position at which fluid is detected and the Z-height/volume table, the System calculates the volume of fluid in the well and compares it to the volume specified in the pipetting description. If sufficient volume is present, the aspiration sequence is initiated. (If sufficient volume is not present, the test is aborted and the test request moved to the exception list.)
The following occur simultaneously until the total volume of sample required is aspirated:
Pipettor Z-axis motor is moved down at a rate of "X" steps/sec.
Syringe aspirates "X" uL at a rate of "X" uL/sec.
LLS is checked to ensure probe still in liquid.
LLS is disabled.
Pipette Z-axis is moved up to Z-above position.
4) MEIA buffer and sample are added to microparticles in incubation well Pipette Z-axis is moved down to the dispense position within the RV incubation well.
Syringe dispenses "X" uL of MEIA buffer and sample at a rate of "X" uL/sec.
Pipette Z-axis is moved up to Z-clear position.
Probe Post-wash
The probe is again washed to ensure that it is free from contamination as described in #6 - SAMPLE KITTING.

1ST PIPETTE ACTIVITY COMPLETE

CARTRIDGE LOAD (This activity occurs when resources are not in use.)
1) Move the auxiliary carousel so that reserved position is under feeder.
2) Cycle trap-door mechanism to load flashlight into carousel.
3) Cycle shuttle mechanism to place another MEIA cartridge on trap door (for next tab load).
Check incubation timer. When expires start next pipetting.

2ND PIPETTE ACTIVITY (TRANSFER OF REACTION MIXTURE TO MATRIX)

Pipette
1) incubation timer is set according to assay file specifications.
2) Buffer aspirate
The process carousel is moved so that the RV is at the pipetting station.
Syringe aspirates "X" uL of air at a rate of "X" uL/sec.
Pipette R-axis is moved over the RV buffer well.
Pipette Z-axis is moved down to the Z-above position.
Pipette Z-axis is moved down to the Z-LLS position.
LLS is enabled to ensure no liquid currently detected.
Pipette Z-axis is moved down at constant speed until fluid is detected OR until the
Z-Asp limit is reached.
  *IT WILL BE ASSUMED THAT FLUID IS DETECTED*
Based on the Z-height position at which fluid is detected and the Z-height/volume table, the System calculates the volume of fluid in the well and compares it to the volume specified in the pipetting description. If sufficient volume is present, the aspiration sequence is initiated. (If sufficient volume is not present, the test is aborted and the test request moved to the exception list.)
The following occur simultaneously until the total volume of buffer required is aspirated:
Pipette Z-axis motor is moved down at a rate of "X" steps/sec.
Syringe aspirates "X" uL at a rate of "X" uL/sec.
LLS is checked to ensure probe still in liquid.
LLS is disabled.
Pipette Z-axis is moved up to the Z-above position.
3) Reaction mixture aspirate
Pipette R-axis is moved over the RV incubation well.
Pipette Z-axis is moved down to the Z-LLS position.
LLS is enabled to ensure no liquid currently detected.
Pipette Z-axis is moved down at constant speed until fluid is detected OR until the Z-Asp limit is reached. *IT WILL BE ASSUMED THAT FLUID IS DETECTED*
Based on the Z-height position at which fluid is detected and the Z-height/volume table, the System calculates the volume of fluid in the well and compares it to the volume specified in the pipetting description. If sufficient volume is present, the aspiration sequence is initiated. (If sufficient volume is not present, the test is aborted and the test request moved to the exception list.)
The following occur simultaneously until the total volume of reaction mixture required is aspirated:
Pipette Z-axis motor is moved down at a rate of "X" steps/sec.
Syringe aspirates "X" uL at a rate of "X" uL/sec.
LLS is checked to ensure probe still in liquid.
LLS is disabled.
Pipette Z-axis is moved up to the Z-clear position.
4) Reaction mixture dispense onto matrix
The following are performed simultaneously and concurrently with the reaction mixture aspirate (above):
The auxiliary carousel is moved so that the cartridge is at the pipetting station.
Pipette R-axis is moved over the MEIA cartridge (matrix) surface.
Pipette Z-axis is moved down to the matrix dispense position.
Syringe dispenses "X" uL of reaction mixture at a rate of "X" uL/sec.
System delays "X" seconds until reaction mixture has been absorbed by matrix.
5) Buffer wash of matrix
Syringe dispenses "X" uL of buffer at a rate of "X" uL/sec.
Pipette Z-axis is moved up to the Z-clear position.
Probe Post-wash
The probe is again washed to ensure that it is free from contamination as described in #6 - SAMPLE KITTING.

2ND PIPETTE ACTIVITY COMPLETE

Check incubation timer. When expires start next pipetting.

3RD PIPETTE ACTIVITY (CONJUGATE ADDITION)

Pipette
1) incubation timer is set according to assay file specifications.
2) Conjugate aspirate
The process carousel is moved so that the RV is at the pipetting station.
Syringe aspirates "X" uL of air at a rate of "X" uL/sec.
Pipette R-axis is moved over the RV reagent 1 (conjugate) well.
Pipette Z-axis is moved down to the Z-above position.
LLS is enabled to ensure no liquid currently detected.
Pipette Z-axis is moved down at constant speed until fluid is detected OR until the Z-Asp limit is reached. *IT WILL BE ASSUMED THAT FLUID IS DETECTED*
Based on the Z-height position at which fluid is detected and the Z-height/volume table, the System calculates the volume of fluid in the well and compares it to the volume specified in the pipetting description. If sufficient volume is present, the aspiration sequence is initiated. (If sufficient volume is not present, the test is aborted and the test request moved to the exception list.)

The following occur simultaneously until the total volume of conjugate required is aspirated:
Pipette Z-axis motor is moved down at a rate of "X" steps/sec.
Syringe aspirates "X" uL at a rate of "X" uL/sec.
LLS is checked to ensure probe still in liquid.
LLS is disabled.
Pipette Z-axis is moved up to the Z-clear position.
3) Conjugate dispense
The following are performed simultaneously:
The auxiliary carousel is moved so that the cartridge is at the pipetting station.
Pipette R-axis is moved over the cartridge (matrix) surface.
Pipette Z-axis is moved down to the matrix dispense position.
Syringe dispenses "X" uL of conjugate at a rate of "X" uL/sec.
Pipette Z-axis is moved up to the Z-clear position.
Wait "X" seconds until reaction mixture has been absorbed by matrix.
Probe Post-wash
The probe is again washed to ensure that it is free from contamination as described in #6 - SAMPLE KITTING.

3RD PIPETTE ACTIVITY COMPLETE

RV UNLOAD (This activity occurs when resources are not in use.)
1) The following are performed simultaneously:
Process carousel is rotated so that the empty position is at the transfer station.
Transfer mechanism O-axis is moved to process carousel.
2) RV is grabbed with the transfer mechanism R-axis and pulled into the transfer mechanism.
3) Transfer mechanism O-axis is rotated so that RV is aligned with the waste container.
4) RV is pushed into the waste container.
Check incubation timer. When expires start next activity.
The MEIA reader is prepared to take a read:
Lamp intensity is brought from simmer state to burn state.
PMT gain is set.
Matrix Wash
1) Auxiliary carousel is rotated so that the cartridge is at the matrix wash station.
2) The following steps are repeated until all the buffer specified in the assay file for cartridge wash has been dispensed.
"X" uL of heated MEIA buffer are dispensed in 50 uL cycles at a rate of "X" uL/sec onto the matrix.
Wait "n" seconds.
TAB WASH COMPLETE
MUP Dispense
1) Auxiliary carousel is rotated so that the cartridge is at the MUP station.
2) 50 uL of heated MUP are dispensed at a rate of "X" uL/sec onto the matrix.
3) Wait "n" seconds.
MUP DISPENSE COMPLETE
Read
1) Auxiliary carousel is rotated so that the flashlight is at the read station.
2) The following steps are repeated until the number of micro-reads specified in the assay file have been taken. (This number is usually 8.)
Read for "X.XX" secs
Wait "X.XX" secs
3) The reader is returned to its idle state:
Lamp intensity is returned to simmer state.
PMT gain is set.
4) The raw reads are converted to normalized reads (light intensity hitting detector/lamp intensity) by the optics microprocessor.
5) A rate is calculated by the System from the normalized reads vs time.
6) For quantitative assays, the rate is fitted to a calibration curve to yield a concentration result.
7) For qualitative assays, the sample rate is compared to an index or cutoff rate to determine if the sample is positive or negative (or reactive or nonreactive).
READ COMPLETE
CARTRIDGE UNLOAD (This activity occurs when resources are not in use.)
1) Auxiliary carousel is rotated so that flashlight is at the ejector station.
2) Ejector is cycled to place flashlight into waste container.

Schematic reaction sequences are presented in FIGS. 26, 27 and 28 which are typical of assays that can be handled by the automated immunoassay analytical system of the invention. In FIG. 26, a T4 assay, FPIA sequence 420, is presented wherein Step 1, T4 bound by thyroxine binding protein (TBP) 424, is reacted with T4 displacing agent 426 to yield TBP 428 plus unbound T4 (430). In step 2, the T4 (430) is added to T4 antibody 432 which yields a reaction product 434 (T4 antibody-T4 complex). In Step 3, the T4 antibody-T4 complex 434 is treated with T4 tracer (fluorescent) 436 which yields a fluorescent polarization measurable reaction product 438.

In FIG. 27, a schematic reaction sequence 440 for a 1-step sandwich MEIA determination (ferritin) is presented. In Steps 1 and 2 an anti-ferritin alkaline phosphatase conjugate is mixed with ferritin sample 444 and anti-ferritin microparticles 446 to yield a ferritin antibody-antigen-antibody complex 448. In step 3, the antibody-antigen-antibody complex 448 is reacted with 4-methylumbelliferyl phosphate (MUP) 450 which yields methylumbelliferone (MU) which is fluorescent. The rate of MU production is measured.

In FIG. 28, the schematic reaction sequence 456 for a 2-step sandwich MEIA is provided for hTSH assay. Anti-hTSH specific microparticles 458 are added to the hTSH sample 460 which provides a reaction product hTSH antibody-antigen complex 462. In Steps 2 through 4, the complex 462 is combined with an anti-hTSH alkaline phosphatase 464 yielding hTSH antibody-antigen-antibody complex 466. In step 5, the complex 466 is reacted with MUP 450 to yield MU which is fluorescent. The rate of MU production is measured.

In accordance with the embodiments of the present invention, the automated immunoassay analytical system provides apparatus, software, hardware and process technology for performing a multitude of assays continuously and with random access being available to the operator. The utilization of carousel pipettor technology for kitting and pipetting operations at either the main carousel or the process carousel, depending on the scheduled test, provides scheduling flexibilities heretofore unachievable. The inventive system allows for a commonality of kitting and pipetting for either immuno precipitation or competitive immunoassay technologies utilizing a common main carousel, transfer station, first kitting and pipetting probe and process carousel as well as a second pipetting probe before separating into respective apparatus and process requirements. Also shared is the commonality of cabinetry disposal and supply materials as well as a common computer network for scheduling, testing, kitting and pipetting.

It will be seen that multiple assays can be performed with a minimum of operator input or handling on the system and the system can be utilized for other processes and assays which have not been directly discussed but will be readily apparent to one practiced in the art in view of the above invention disclosure and the claims. It will also be appreciated that although particular embodiments of the present invention have been disclosed, various changes and adaptations to the apparatus and methods can be made without departing from the teachings of the specification and scope of the invention as set out in the following claims.

We claim:

1. An automated, continuous and random access analytical system apparatus capable of simultaneously performing multiple assays of a plurality of liquid samples, said apparatus comprising:
   a. a front end carousel assembly inclusive of a sample cup carousel, a reagent pack carousel and a reaction vessel carousel mounted concentrically;
   b. kitting means for kitting a reaction vessel positioned in said reaction vessel carousel, said kitting means further including a transfer pipetting means positioned adjacent said front end carousel assembly for transferring a liquid sample from said sample cup carousel and reagents from said reagent pack carousel to said reaction vessel without initiation of an assay reaction sequence;
   c. a process carousel positioned within a controlled environment having environment means for maintaining said controlled environment within a predetermined temperature;
   d. a transfer station having means for transferring said kitted reaction vessel from said reaction vessel carousel to said process carousel;
   e. a process carousel transfer means for transferring and mixing reagents with said liquid sample in said kitted reaction vessel to form a reaction mixture;
   f. at least two different assay reader means, at least one of said assay reader positioned adjacent said process carousel for detecting said reaction mixture;
   g. means for transferring said reaction mixture from said process carousel to a reaction cartridge contained in a cartridge wheel carousel, another one of said assay reader means positioned adjacent said cartridge wheel carousel for detecting said reaction mixture in said cartridge;
   h. means for transferring said reaction vessel from said process carousel to said transfer station, said transfer station having removing means for removing said reaction vessel from said system; and
   i. means for removing said cartridge from said cartridge wheel carousel.

2. An apparatus according to claim 1 wherein said cartridge wheel carousel containing multiple disposable cartridges, said apparatus further including means for supplying said cartridges to said cartridge wheel carousel and disposing of said cartridges from said cartridge wheel carousel.

3. The apparatus according to claim 1 wherein said assay reader means include means for optically monitoring said reaction mixture.

4. The apparatus according to claim 1 wherein said assay reader means provides calibration and recording means for said reaction mixture.

5. The apparatus according to claim 1 wherein the transfer means of said transfer station is comprised of a carousel rotable about an axis, an arm with a pick for mating with a reaction vessel transfer projection means and means for pulling the reaction vessel from the front end carousel, rotating and placing the reaction vessel onto the process carousel through rotation and rack and pinion movement of the pick arm.

6. The apparatus according to claim 1 wherein sample cups in said sample cup carousel and reagent packs in said reagent pack carousel include coded information and wherein said front end carousel assembly includes means for identifying said liquid samples and liquid reagents from said coded information of said sample cups and said reagent packs.

7. The apparatus according to claim 1 which further includes means for storing the output readings of said assay reader means.

8. The apparatus according to claim 1 which further includes means for calculating concentration of an analyte from output readings of said assay reader means.

9. The apparatus according to claim 1 wherein the reaction vessel contains a reaction cuvette having a physical characteristic of low birefringence through an optical read region.

10. An automated, continuous and random access analytical system capable of simultaneously performing multiple assays of a plurality of liquid sample, said system comprising:
   a. a front end carousel assembly inclusive of a sample cup, a reagent pack carousel and a reaction vessel carousel, said reaction vessel carousel being concentrically mounted exterior of said reagent pack carousel and said reagent pack carousel being concentrically mounted exterior of said sample cup carousel;
   b. a process carousel, said process carousel having environmental means for maintaining said process carousel within a predetermined temperature and timing of reaction incubation;
   c. a cartridge wheel carousel, said cartridge wheel carousel offset from said process carousel;
   d. means for rotating the respective carousels to align with a kitting pipettor means for kitting a reaction vessel positioned in said reaction vessel carousel to form a kitted mixture therein without initiation of an assay reaction sequence;
   e. means for transferring said kitted reaction vessels from said reaction vessel carousel to a transfer station, said transfer station having means for transferring said kitted reaction vessel to said process carousel;
   f. transfer pipettor means for transferring and mixing reagents to said reaction vessel positioned in said process vessel to form a reaction mixture therein, and for transferring said reaction mixture from said reaction vessel in said process carousel to said cartridge wheel carousel;
   g. said cartridge wheel carousel further including means for receiving reaction mixture from said process carousel, and means for supplying cartridges to said cartridge wheel carousel;

h. said process carousel further having integrated therewith a fluorescent polarization immunoassay reader and a first processing station;

i. said cartridge wheel process carousel further having integrated therewith a microparticle enzyme immunoassay reader and a second processing station;

j. means for removing said reaction vessel from said process carousel by operation of said transfer station;

k. means for removing said cartridges from said cartridge wheel carousel; and l. means for analyzing said reaction mixture either by fluorescent polarization immunoassay reader or microparticle enzyme immunoassay reader.

11. The system according to claim 10 wherein said assay readers include means for optically monitoring said reaction mixture.

12. The system according to claim 10 wherein said assay readers including calibration means and recording means for said reaction mixture.

13. The system according to claim 10 wherein the transfer means of said transfer station is comprised of a carousel rotable about an axis, an arm with a pick for mating with a reaction vessel transfer projection means and means for pulling the reaction vessel from the front end carousel assembly, rotating and placing the reaction vessel onto the process carousel through rotation and rack and pinion movement of the pick arm.

14. The apparatus according to claim 10 wherein sample cups in said sample cup carousel and reagent packs in said reagent pack carousel include coded information and wherein said front end carousel assembly includes means for identifying said liquid samples and liquid reagents from said coded information of said sample cups and said reagent packs.

15. The system according to claim 10 which includes means for storing output readings of said assay readers.

16. The system according to claim 10 which includes means for calculating the concentration of an analyte from output readings of said assay readers.

17. The system according to claim 14 wherein the sample cup is free standing on a sample cup base when separated from the sample cup carousel.

* * * * *